US012570703B2

(12) United States Patent
Schuman et al.

(10) Patent No.: US 12,570,703 B2
(45) Date of Patent: Mar. 10, 2026

(54) GENETICALLY ENCODED PROTEIN SYNTHESIS INHIBITOR

(71) Applicant: Max-Planck-Gesellschaft zur Förderung der Wissenschaften e.V., Munich (DE)

(72) Inventors: Erin M. Schuman, Frankfurt am Main (DE); Maximilian Heumüller, Frankfurt am Main (DE); Caspar Glock, Frankfurt am Main (DE)

(73) Assignee: MAX-PLANCK-GESELLSCHAFT ZUR FÖRDERUNG WISSENSCHAFTEN E.V., Munich (DE)

( * ) Notice: Subject to any disclaimer, the term of this patent is extended or adjusted under 35 U.S.C. 154(b) by 291 days.

(21) Appl. No.: 17/614,999

(22) PCT Filed: May 28, 2020

(86) PCT No.: PCT/EP2020/064801
§ 371 (c)(1),
(2) Date: Nov. 29, 2021

(87) PCT Pub. No.: WO2020/239890
PCT Pub. Date: Dec. 3, 2020

(65) Prior Publication Data
US 2022/0220164 A1 Jul. 14, 2022

(30) Foreign Application Priority Data

May 31, 2019 (EP) ..................................... 19177622

(51) Int. Cl.
| | |
|---|---|
| *C12N 9/24* | (2006.01) |
| *C07K 14/415* | (2006.01) |
| *C12N 15/63* | (2006.01) |
| *C12N 15/82* | (2006.01) |

(52) U.S. Cl.
CPC .......... *C07K 14/415* (2013.01); *C12N 9/2497* (2013.01); *C12N 15/635* (2013.01); *C12N 15/8201* (2013.01); *C12N 2840/002* (2013.01); *C12Y 302/02022* (2013.01)

(58) Field of Classification Search
None
See application file for complete search history.

(56) References Cited

U.S. PATENT DOCUMENTS

| | | | |
|---|---|---|---|
| 5,635,384 A | 6/1997 | Walsh et al. | |
| 8,715,676 B2 * | 5/2014 | Chen ....................... | A61P 35/00 435/320.1 |

FOREIGN PATENT DOCUMENTS

| | | |
|---|---|---|
| EP | 0 652 231 A1 | 5/1995 |
| WO | 02/33106 A2 | 4/2002 |
| WO | 2012/038950 A1 | 3/2012 |

OTHER PUBLICATIONS

Bass et al. Plant Cell (1992), vol. 4, pp. 225-234.*
Tan, et al: "Cloning and Expression of Oil Palm (*Elaeis guineensis Jacq.*) Type 2 Ribosome Inactivating Protein in *Escherichia coli*", International Journal of Peptide Research and Therapeutics, vol. 22, No. 1, Aug. 13, 2016, pp. 37-44.
Schnuetgen et al: "A directional strategy for monitoring Cre-mediated recombination at the cellular level in the mouse", Nature Biotechnology, vol. 21, No. 5, Mar. 31, 2003, pp. 562-565.
Law et al: "A switch-on mechanism to activate maize ribosome-inactivating protein for targeting HIV-infected cells", Nucleic Acids Research, vol. 38, No. 19, Jun. 17, 2010, pp. 6803-6812.
Akkouh et al: "Biological activities of ribosome-inactivating proteins and their possible applications as antimicrobial, anticancer, and anti-pest agents and in neuroscience research", Applied Microbiology and Biotechnology, vol. 99, No. 23, Sep. 22, 2015, pp. 9847-9863.
Yang et al: "Solution Structure of an Active Mutant of Maize Ribosome-Inactivating Protein (MOD) and Its Interaction with the Ribosomal Stalk Protein P2", Journal of Molecular Biology, vol. 395, No. 5, Feb. 5, 2010, pp. 897-907.
International Search Report and the The Written Opinion issued in PCT/EP2020/064801, dated Jul. 22, 2020, 6 pages.
Altschul et al, Basic Local Alignmente Search Tool, J Mol Biol 2015, pp. 403-410 (1990).
Sutton & Schuman, E. M. Dendritic protein synthesis, synaptic plasticity, and memory. *Cell* 127, 49-58 (2006).
Walsh et al, Ribosome-inactivating proteins: potent poisons and molecular tools. *Virulence* 4, 774-784 (2013).
Puri et al, Ribosome-inactivating proteins: current status and biomedical applications. *Drug Discov. Today* 17, 774-783 (2012).
Endo et al, The RNA N-glycosidase activity of ricin A-chain. *Nucleic Acids Symp. Ser.* 139-142 (1988).
Hey et al, Maize ribosome-inactivating protein (b-32). Homologs in related species, effects on maize ribosomes, and modulation of activity by pro-peptide deletions. *Plant Physiol.* 107, 1323-1332 (1995).
Mak et al, Structure-function study of maize ribosome-inactivating protein: implications for the internal inactivation region and the sole glutamate in the active site. *Nucleic Acids Research* 35, 6259-6267 (2007).
Schmidt et al, SUnSET, a nonradioactive method to monitor protein synthesis. *Nat. Methods* 6, 275-277 (2009).
Dieterich et al, In situ visualization and dynamics of newly synthesized proteins in rat hippocampal neurons. *Nat. Neurosci.* 13, 897-905 (2010).
Dieck et al, Metabolic labeling with noncanonical amino acids and visualization by chemoselective fluorescent tagging. *Curr Protoc Cell Biol* Chapter 7, Unit 7.11 (2012).

(Continued)

*Primary Examiner* — Medina A Ibrahim
(74) *Attorney, Agent, or Firm* — Rothwell, Figg, Ernst & Manbeck, P.C.

(57) ABSTRACT

The present invention relates to an expression system for a genetically encoded protein synthesis inhibitor containing RNA N-glycosidase activity split into two components. The expression system can be combined with genetic targeting systems to achieve cell- and/or tissue-type-specific and/or temporally-specific control of protein synthesis in a host, particularly in a mammalian host.

17 Claims, 37 Drawing Sheets

Figure 10:
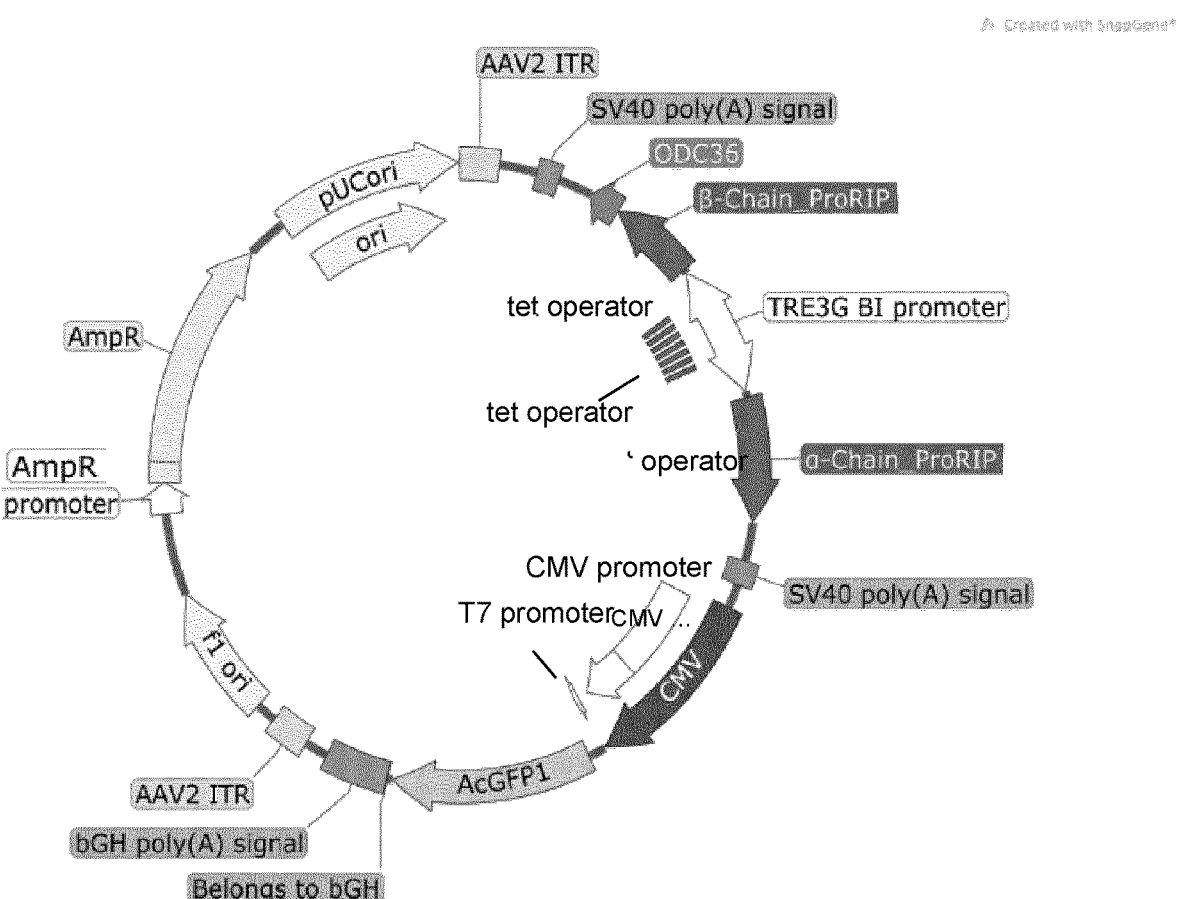

Specification includes a Sequence Listing.

(56) References Cited

OTHER PUBLICATIONS

Davis et al, Protein synthesis and memory: a review. *Psychol Bull* 96, 518-559 (1984).

Ho et al, The cell biology of synaptic plasticity. *Science* 334, 623-628 (2011).

Govindarajan et al, The dendritic branch is the preferred integrative unit for protein synthesis-dependent LTP. *Neuron* 69, 132-146 (2011).

Cajigas et al, Protein homeostasis and synaptic plasticity. *EMBO J.* 29, 2746-2752 (2010).

Aakalu et al, Dynamic visualization of local protein synthesis in hippocampal neurons. *Neuron* 30, 489-502 (2001).

Atasoy et al, A Flex switch targets Channelrhodopsin-2 to multiple cell types for imaging and long-range circuit mapping. *J Neurosci* 28, 7025-7030 (2008).

Woodhead et al, Cell-autonomous beta-catenin signaling regulates cortical precursor proliferation. *J Neurosci* 26, 12620-12630 (2006).

Link et al, Preparation of the functionalizable methionine surrogate azidohomoalanine via copper-catalyzed diazo transfer. *Nat Protoc* 2, 1879-1883 (2007).

Matsuzaki et al, Structural basis of long-term potentiation in single dendritic spines. *Nature* 429, 761-766 (2004).

Marchler-Bauer et al CDD/SPARCLE: functional classification of proteins via subfamily domain architectures. *Nucleic Acids Research* 45, D200-D203 (2017).

Whitfield et al, The estrogen receptor fusion system in mouse models: a reversible switch. Cold Spring Harb Protoc 2015, 227-234 (2015).

Shoji et al, Application of heat shock promoter in transgenic zebrafish. Dev. Growth Differ. 50, 401-406 (2008).

Yamada et al, Light Control of the Tet Gene Expression System in Mammalian Cells. Cell Rep 25, 487-500.e6 (2018).

Schnütgen et al, A directional strategy for monitoring Cre-mediated recombination at the cellular level in the mouse. Nat Biotechnol 21, 562-565 (2003).

Flexner et al, Studies on memory: inhibitors of protein synthesis also inhibit catecholamine synthesis. Proc Natl Acad Sci U S A 72, 4660-4663 (1975).

Zeisel et al, Brain structure. Cell types in the mouse cortex and hippocampus revealed by single-cell RNA-seq. Science 347, 1138-1142 (2015).

Lake et al, Neuronal subtypes and diversity revealed by single-nucleus RNA sequencing of the human brain. Science 352, 1586-1590 (2016).

Rosenberg et al, Single-cell profiling of the developing mouse brain and spinal cord with split-pool barcoding. Science 360, 176-182 (2018).

He et al, Single-cell RNA sequencing of mouse brain and lung vascular and vessel-associated cell types. Sci Data 5, 180160 (2018).

Lo et al, Cancer-specific gene therapy. Adv. Genet. 54, 235-255 (2005).

Axelsen et al, Genes overexpressed in different human solid cancers exhibit different tissue-specific expression profiles. Proc Natl Acad Sci U S A 104, 13122-13127 (2007).

Garg et al, . Survivin: a unique target for tumor therapy. Cancer Cell Int. 16, 49 (2016).

Kakinuma et al, Probasin promoter (ARR(2)PB)-driven, prostate-specific expression of the human sodium iodide symporter (h-NIS) for targeted radioiodine therapy of prostate cancer. Cancer Res. 63, 7840-7844 (2003).

Yu et al, Prostate-tumor targeting of gene expression by lentiviral vectors containing elements of the probasin promoter. Prostate 59, 370-382 (2004).

Liu et al, Cancer-Specific Telomerase Reverse Transcriptase (TERT) Promoter Mutations: Biological and Clinical Implications. Genes (Basel) 7, 38 (2016).

Goodarzi et al, Modulated Expression of Specific tRNAs Drives Gene Expression and Cancer Progression. Cell 165, 1416-1427 (2016).

Hagerman et al, Fragile X syndrome. Nat Rev Dis Primers 3, 17065 (2017).

Ciaccio et al, Fragile X syndrome: a review of clinical and molecular diagnoses. Ital J Pediatr 43, 39 (2017).

Banerjee et al, Aberrant RNA translation in fragile X syndrome: From FMRP mechanisms to emerging therapeutic strategies. Brain Res. 1693, 24-36 (2018).

Darnell et al, Cell 146, pp. 247-261 (2011) FMRP stalls ribosomal translocation on mRNAs linked to synaptic function and autism. Cell 146, 247-261 (2011).

Ascano et al, FMRP targets distinct mRNA sequence elements to regulate protein expression. Nature 492, 382-386 (2012).

Pasciuto et al, SnapShot: FMRP mRNA targets and diseases. Cell 158, 1446-1446.e1 (2014).

Laggerbauer et al, Evidence that fragile X mental retardation protein is a negative regulator of translation. Hum. Mol. Genet. 10, 329-338 (2001).

Eyre et al, Time now to TORC the TORC? New developments in mTOR pathway inhibition in lymphoid malignancies. Br. J. Haematol. 166, 336-351 (2014).

Lipton et al, The neurology of mTOR. Neuron 84, 275-291 (2014).

Bhattacharya et al, Targeting Translation Control with p70 S6 Kinase 1 Inhibitors to Reverse Phenotypes in Fragile X Syndrome Mice. Neuropsychopharmacology 41, 1991-2000 (2016).

Kelleher et al, Cell 135, pp. 401-406 (2008) The autistic neuron: troubled translation? Cell 135, 401-406 (2008).

Hoeffer et al, mTOR signaling: at the crossroads of plasticity, memory and disease. Trends in Neurosciences 33, 67-75 (2010).

Tan Yung-Chie et al., "Cloning and Expression of Oil Palm (*Elaeis guineensis Jacq.*) Type 2 Ribosome Inactivating Protein in *Escherichia coli*", Int J Pept Res Ther 22 No. 1 pp. 37-44 (2016).

Law et al., A switch-on mechanism to activate maize ribosome-inactivating protein for targeting HIV-infected cells, Nucl Acids Res 38, No. 19, pp. 6803-6812 (2010).

Akkouh et al,, "Biological activities of ribosome-inactivating proteins and their possible applications as antimicrobial, anticancer, and anti-pest agents and in neuroscience research", Appl Microb Biot 99, No. 23, pp. 9847-9863 (2015).

Yang et al, Solution Structure of an Active Mutant of Maize Ribosome-lactivating Protein (MOD) and Its Interaction with the Ribosomal Stalk Protein P2, J. Mol. Biol., vol. 395, pp. 897-907 (2010).

The Extended Search Report issued in EP19177622.8 dated Oct. 18, 2019, 11 pgs.

Notification of Transmittal of the International Search Report and Written Opinion issued in PCT/EP2020/064801 dated Jul. 20, 2022, 20 pgs.

Heumüller et al., "A genetically encodable cell-type-specific protein synthesis inhibitor", Nature Methods, vol. 16, Aug. 2019 (9 pages).

* cited by examiner

Figure 1 - Design and function of the gePSI
a
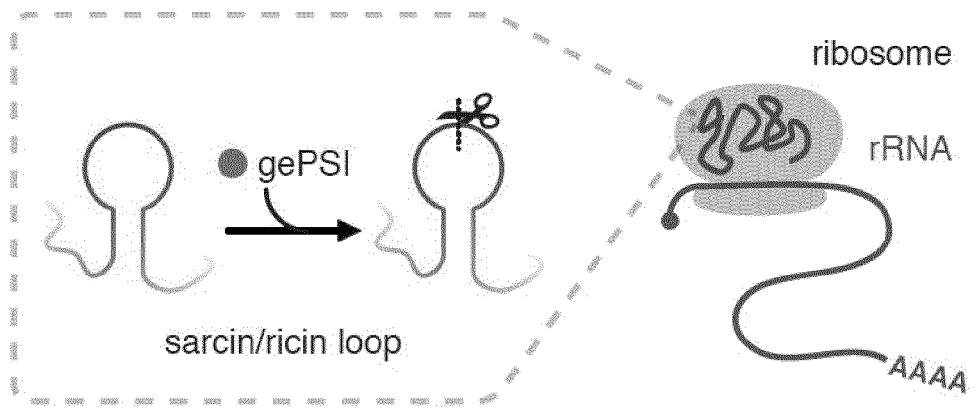
b
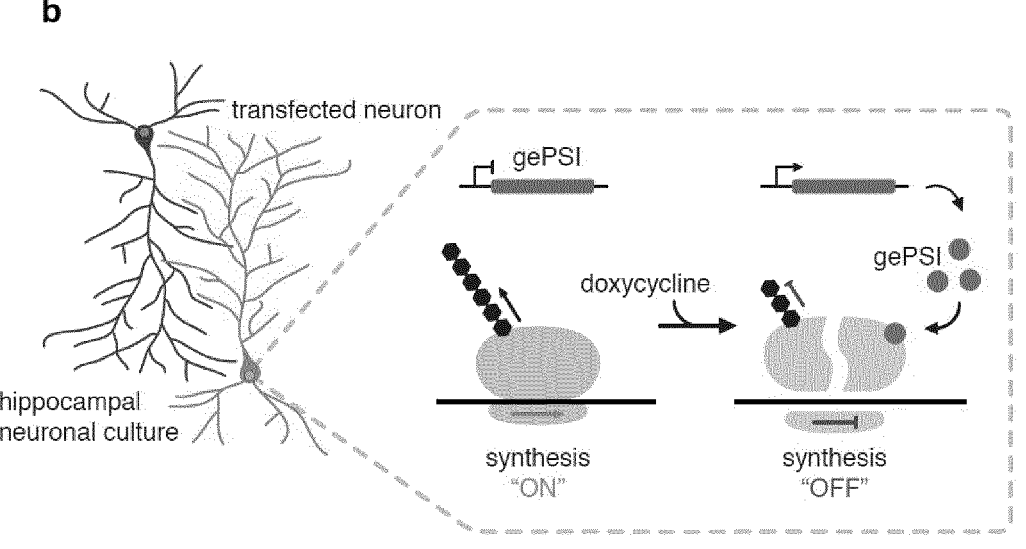

Figure 1 (continued) - Design and function of the gePSI
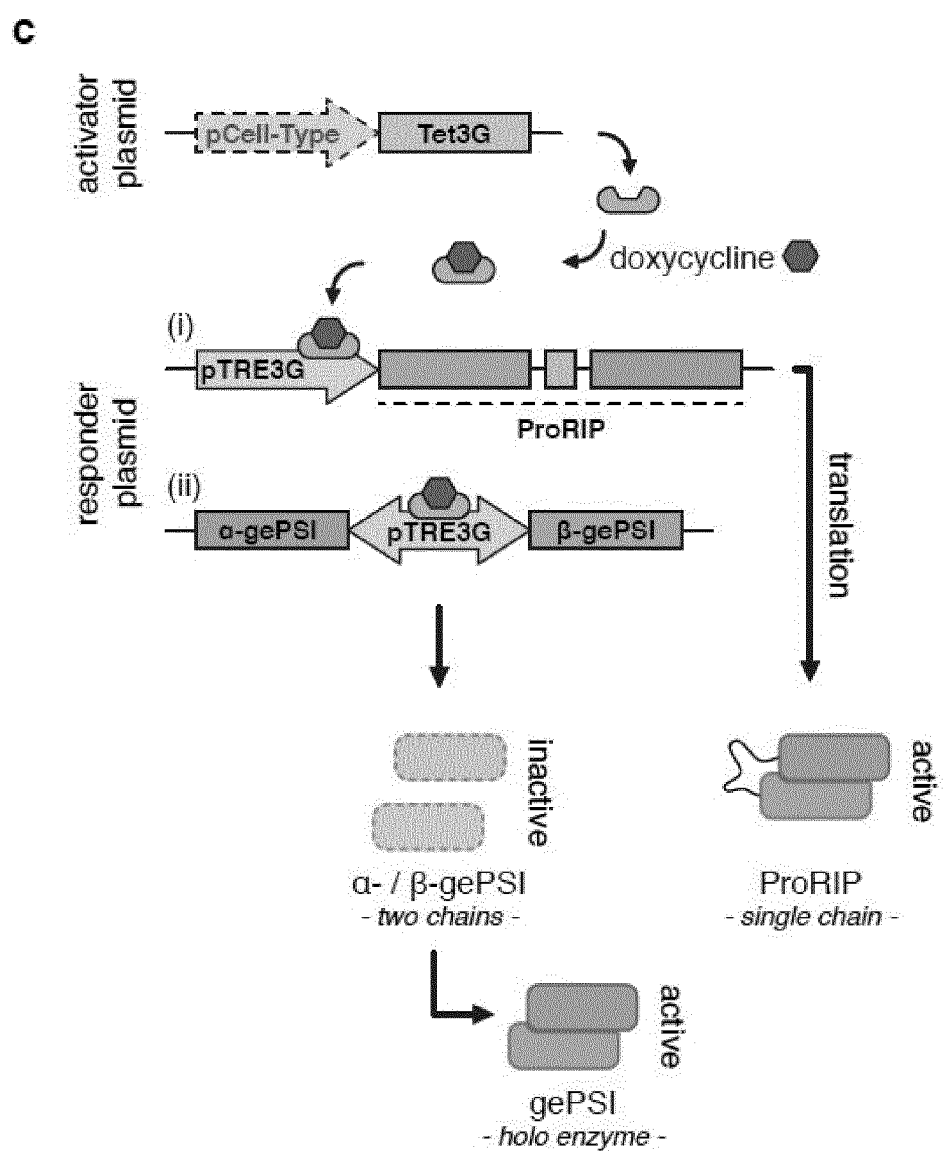

Figure 1 (continued) – Design and function of the gePSI
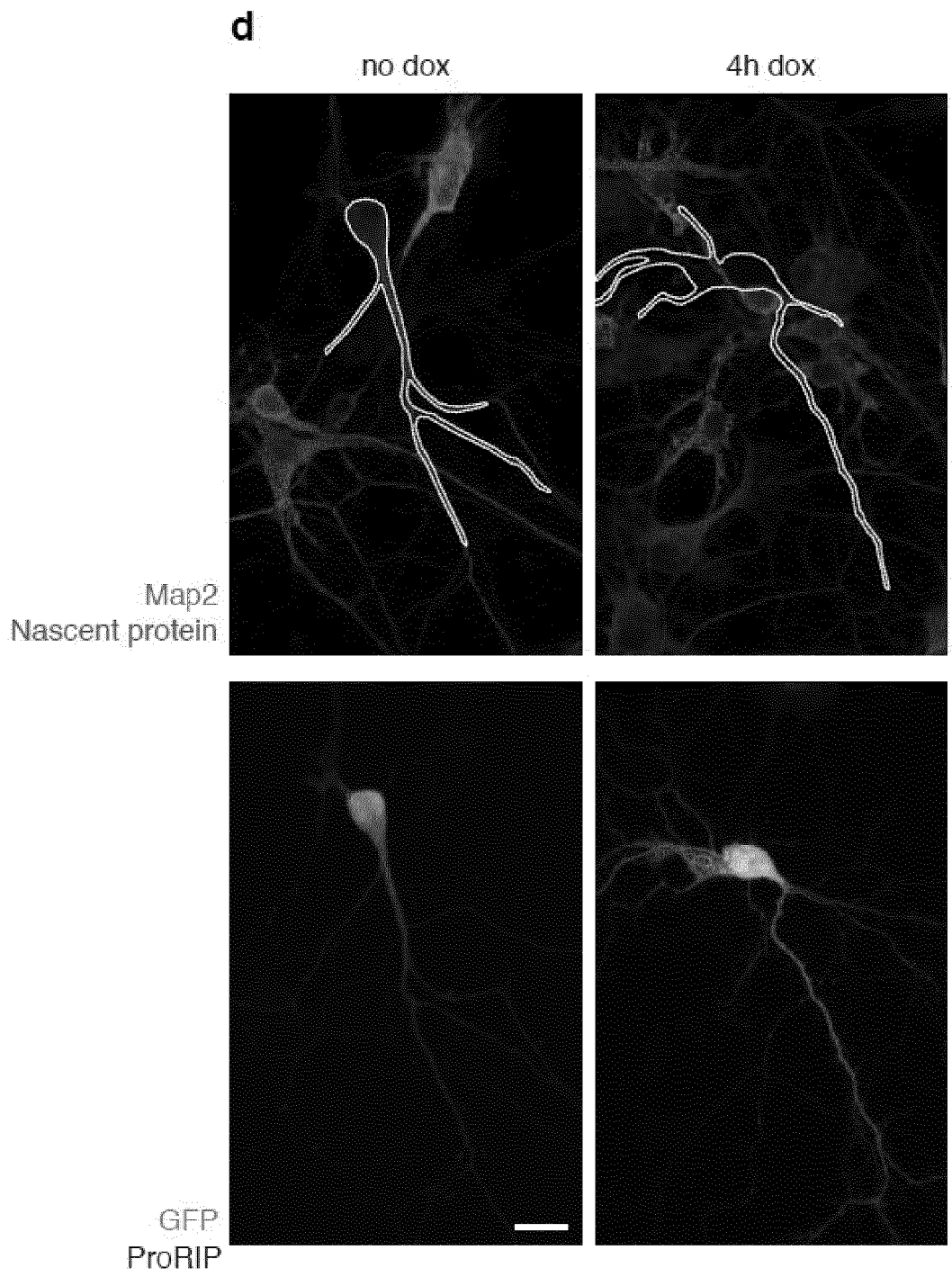

Figure 1 (continued) - Design and function of the gePSI
e
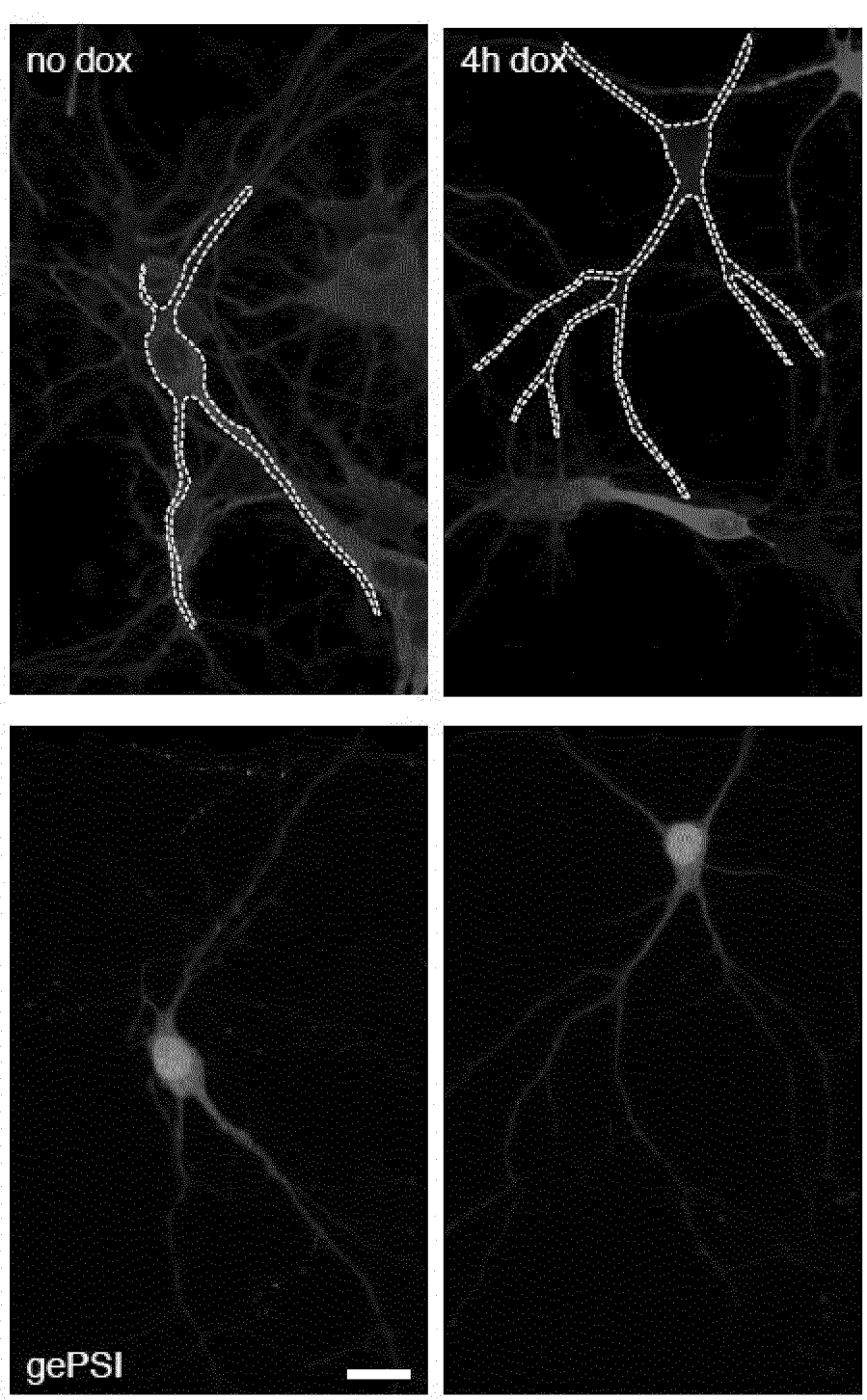

Figure 1 (continued) - Design and function of the gePSI
f
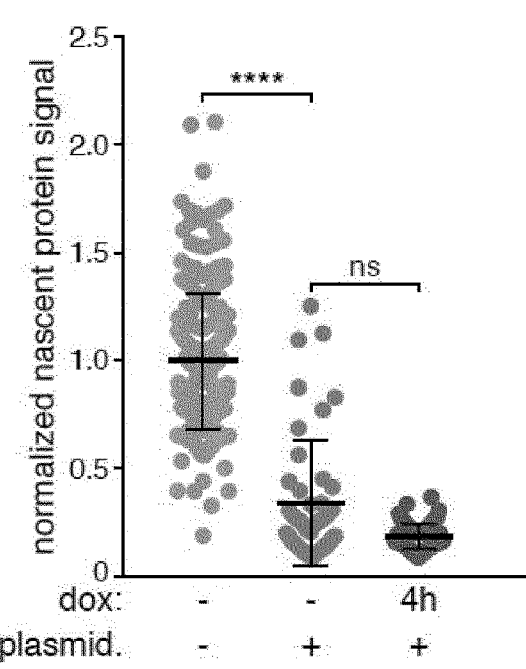
g
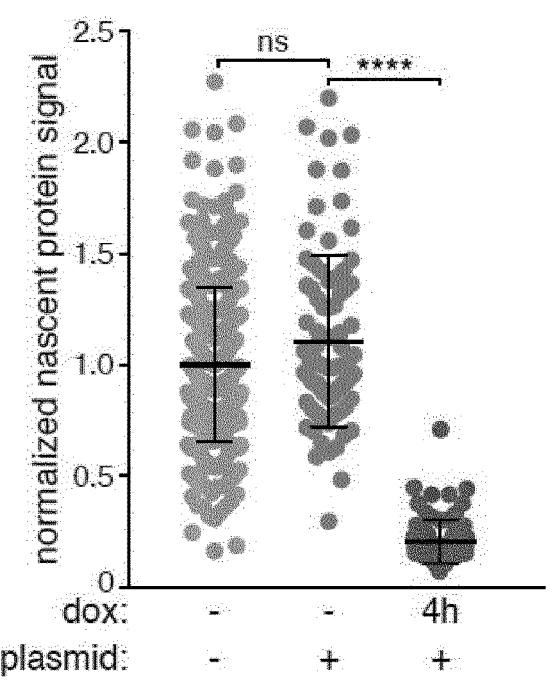

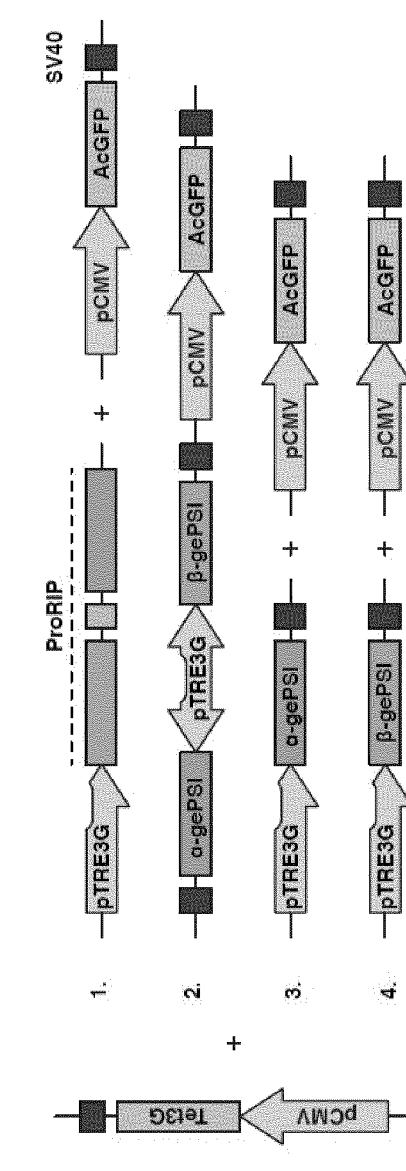
Figure 2 - gePSI expression element controls

Figure 2 (continued) – gePSI expression element controls
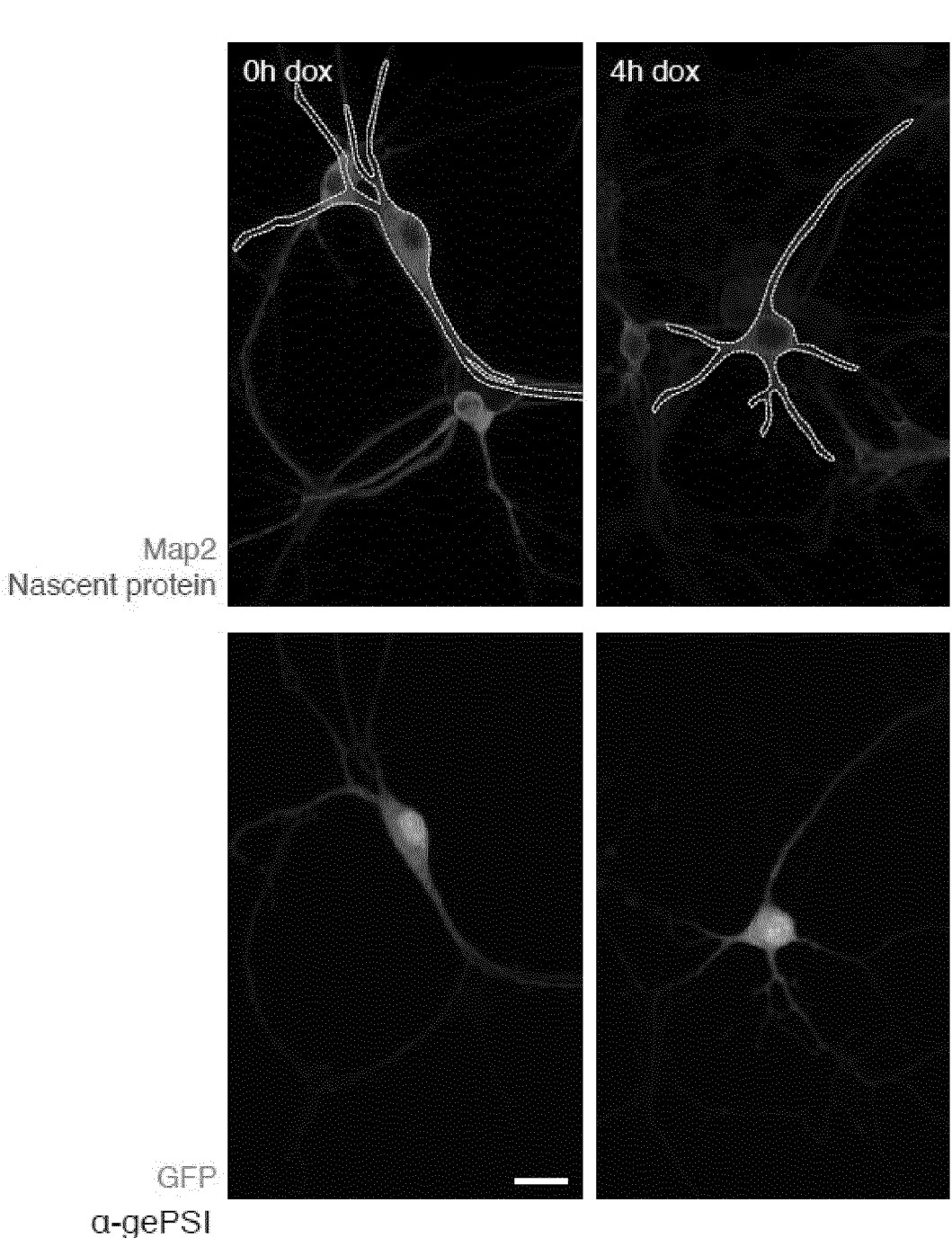

Figure 2 (continued) - gePSI expression element controls
c
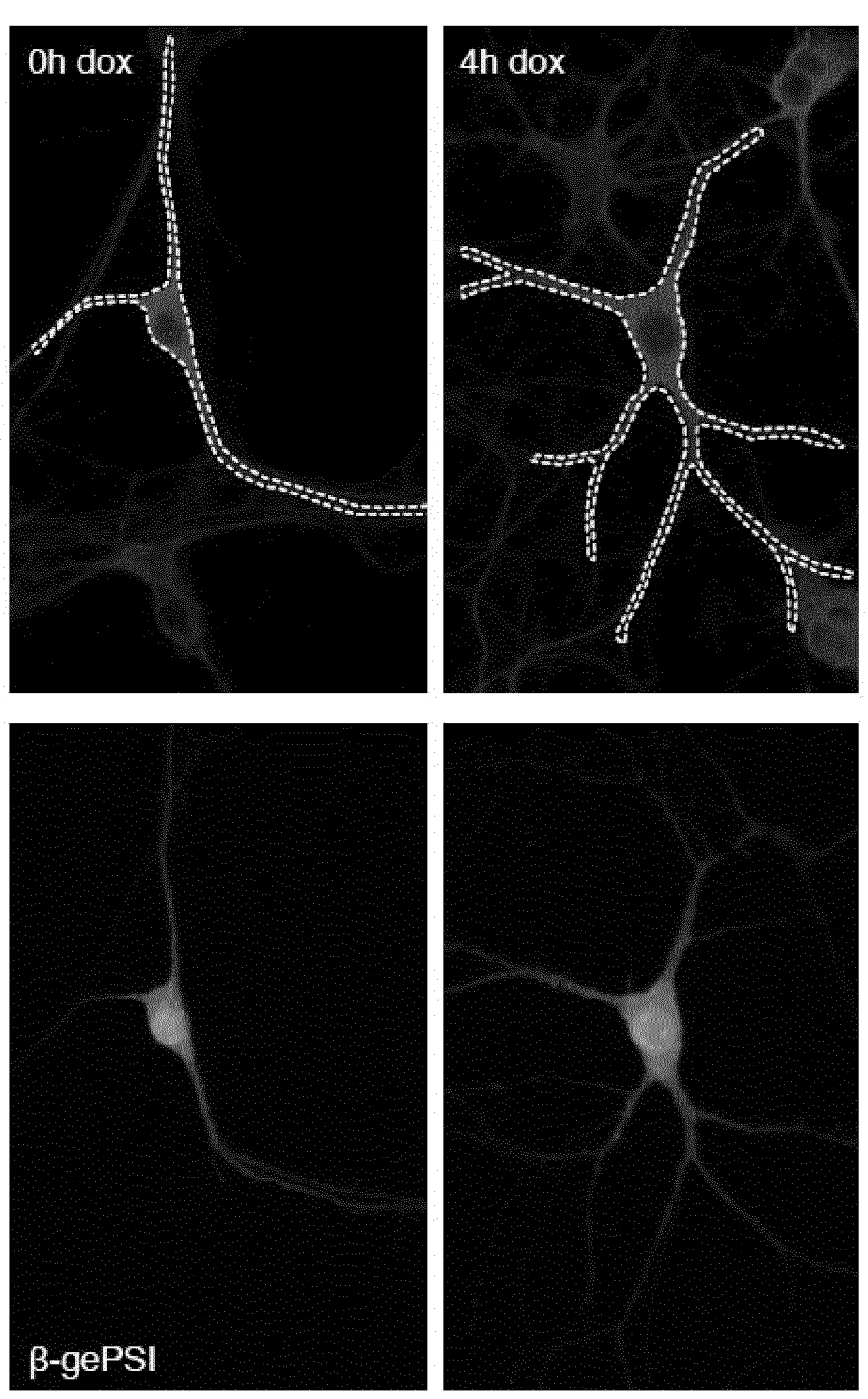

Figure 2 (continued) - gePSI expression element controls
d
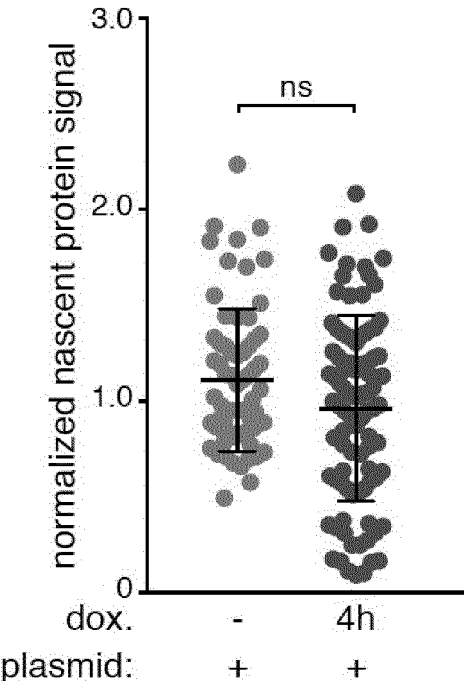
e
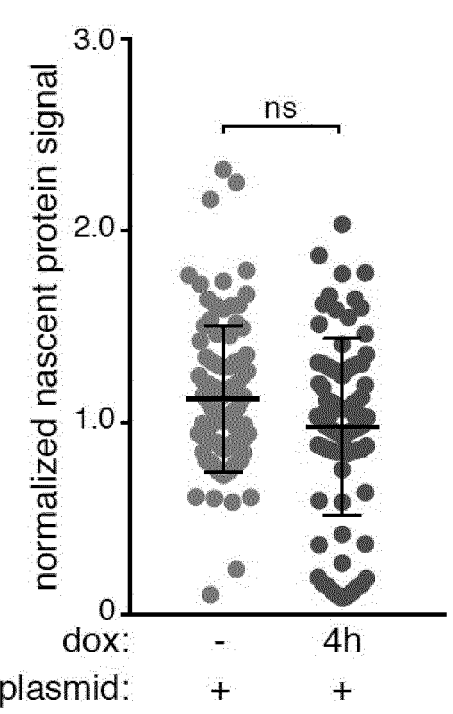

Figure 3 – Detection of gePSI action using FUNCAT and comparison
with pharmacological protein synthesis inhibition
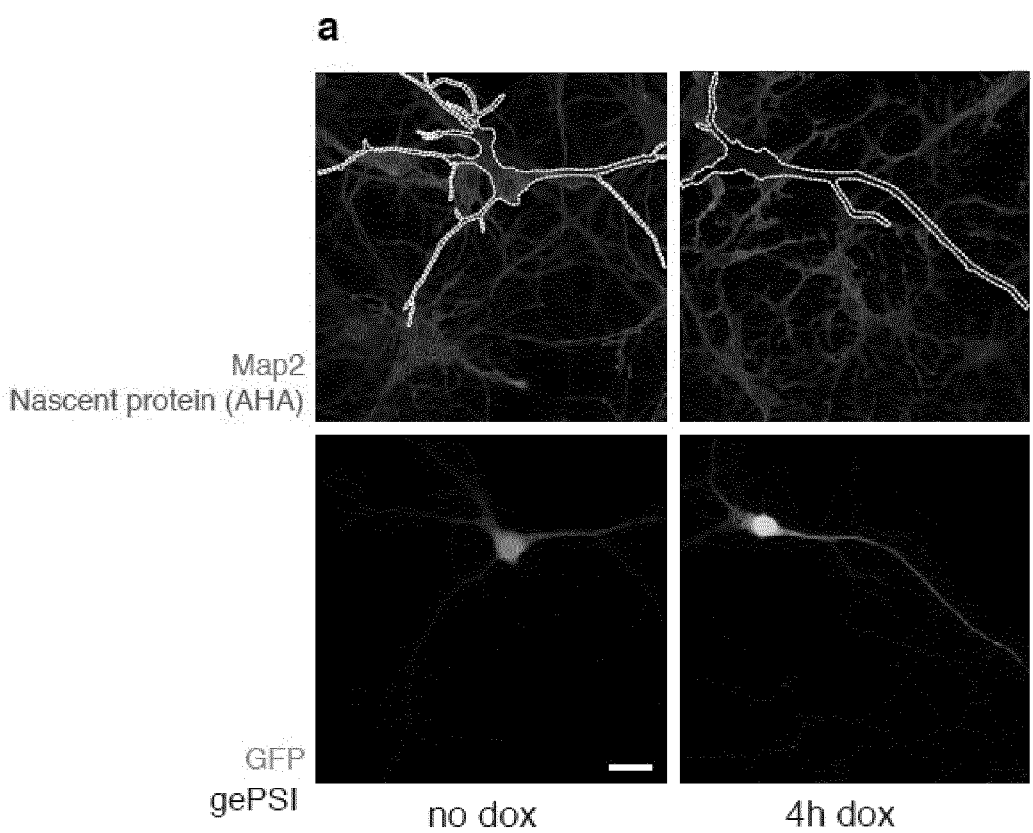

Figure 3 (continued) - Detection of gePSI action using FUNCAT and comparison with pharmacological protein synthesis inhibition
b
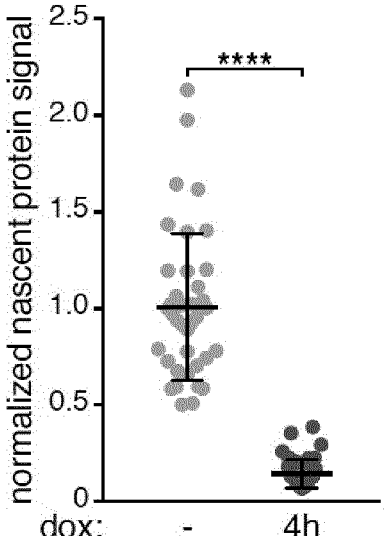
d
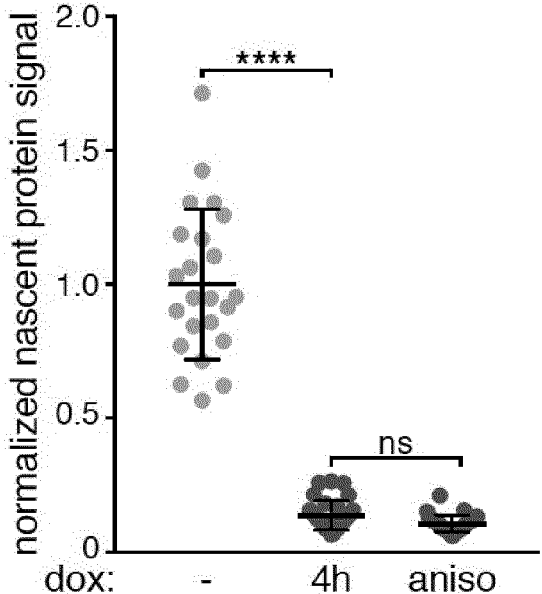

Figure 3 (continued) – Detection of gePSI action using FUNCAT and comparison with pharmacological protein synthesis inhibition
c
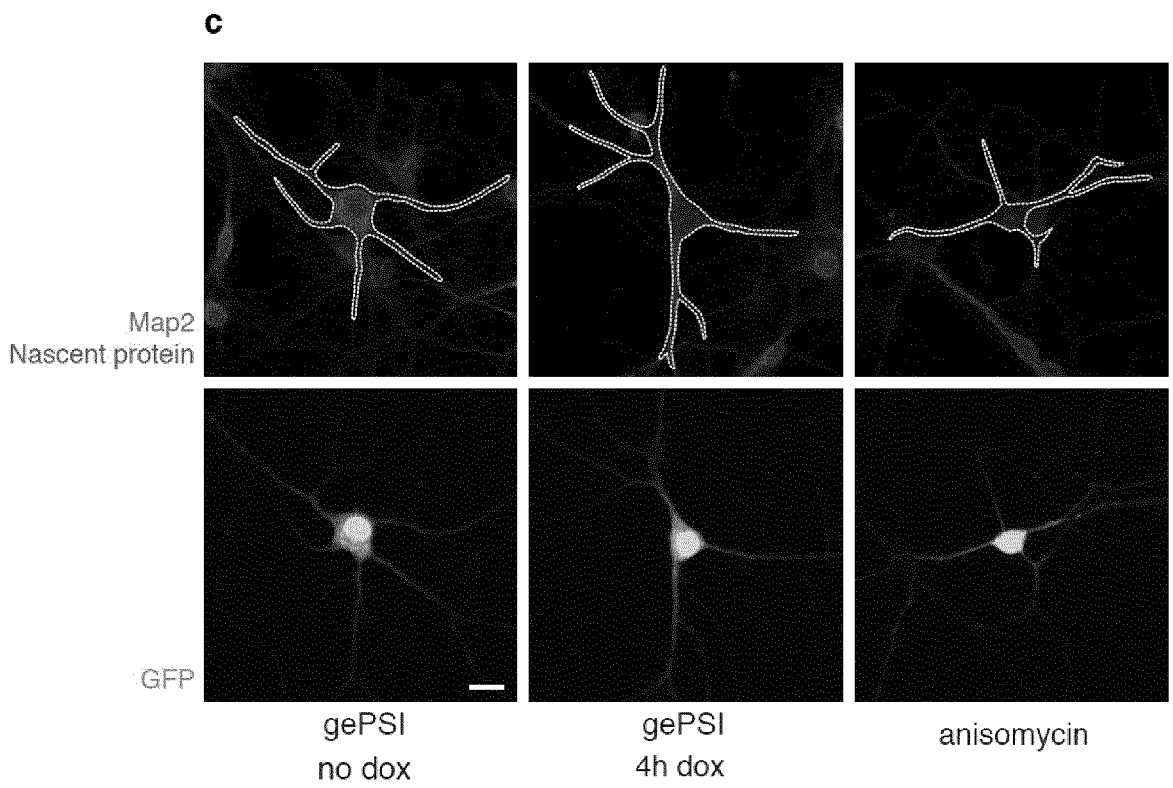
Map2
Nascent protein
GFP
gePSI          gePSI          anisomycin
no dox         4h dox Figure 4 - gePSI expressing cells do not exhibit compromised cell health relative to control cells
a
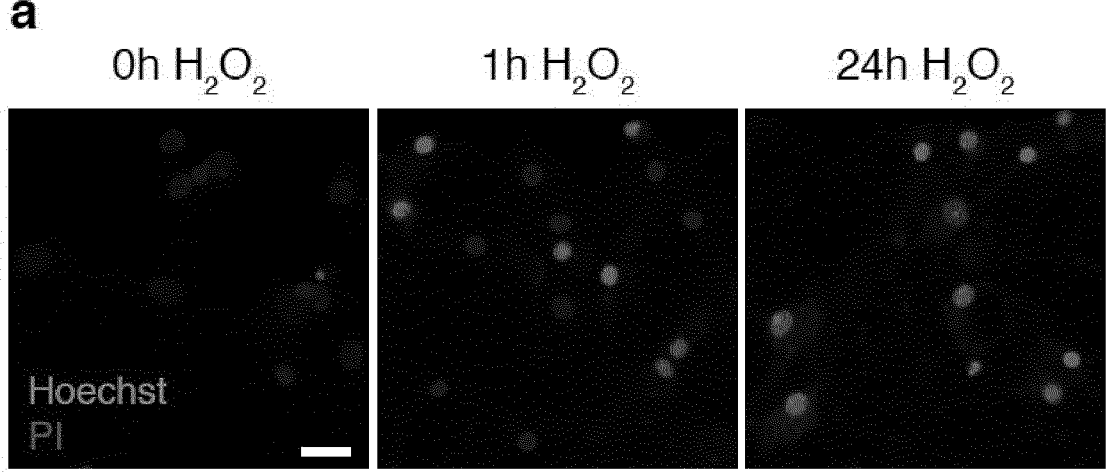
b
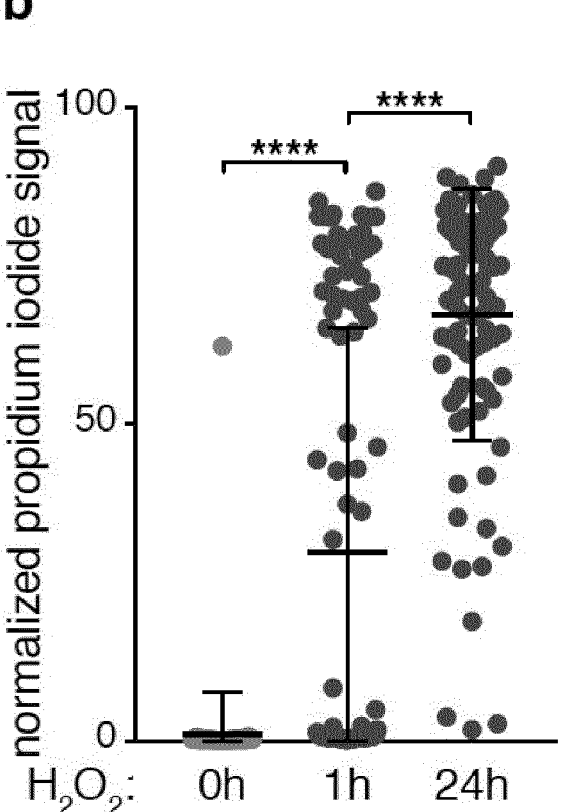

Figure 4 (continued) - gePSI expressing cells do not exhibit compromised cell health relative to control cells
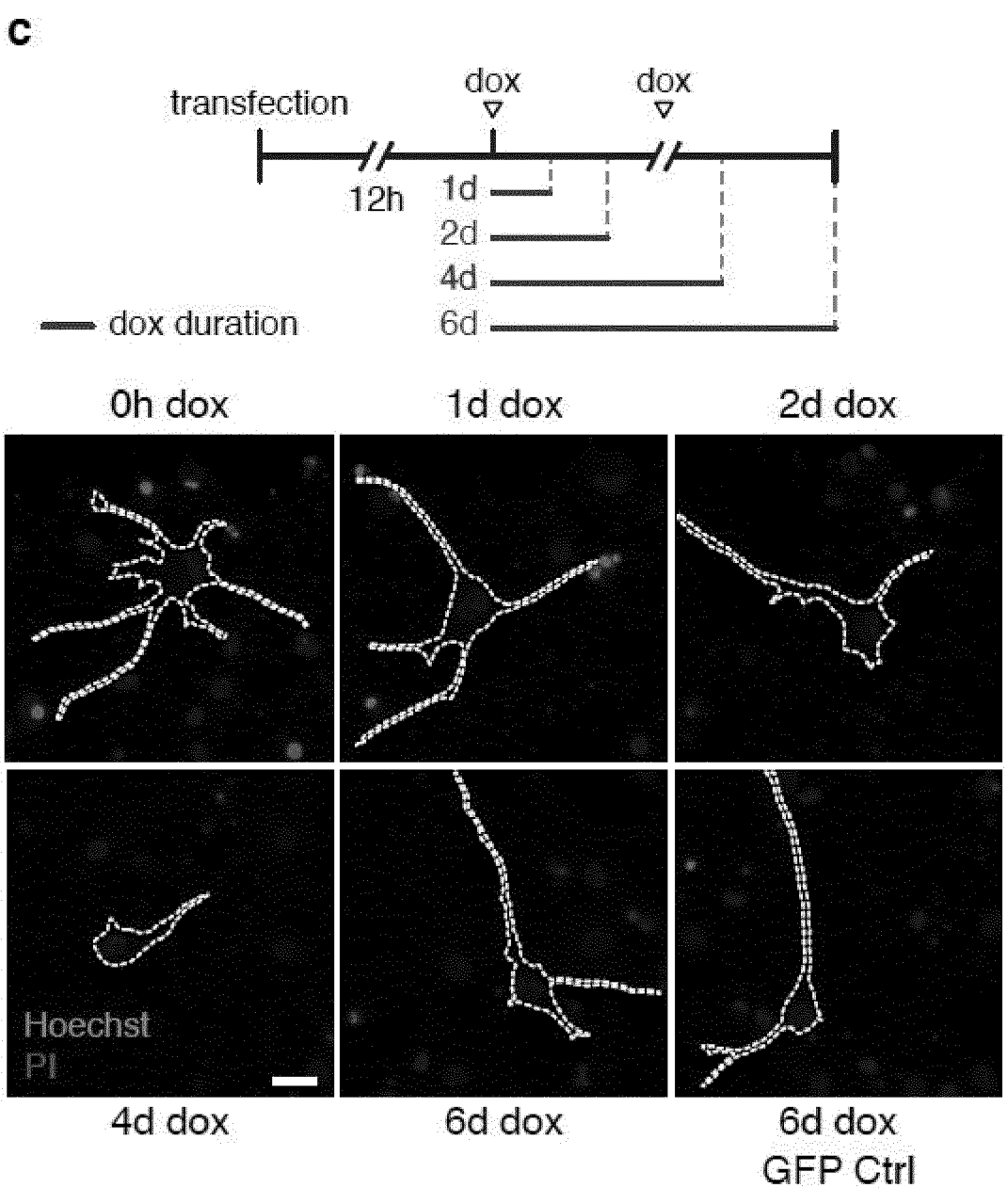

Figure 4 (continued) - gePSI expressing cells do not exhibit compromised cell health relative to control cells
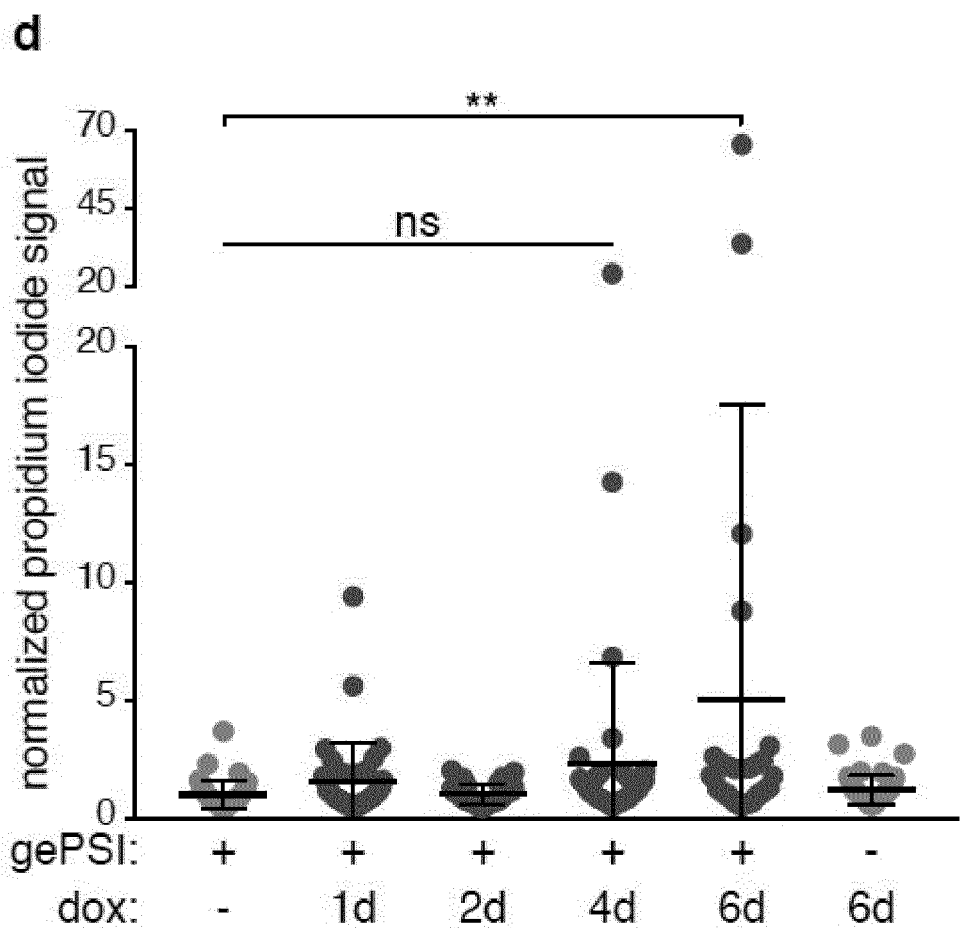

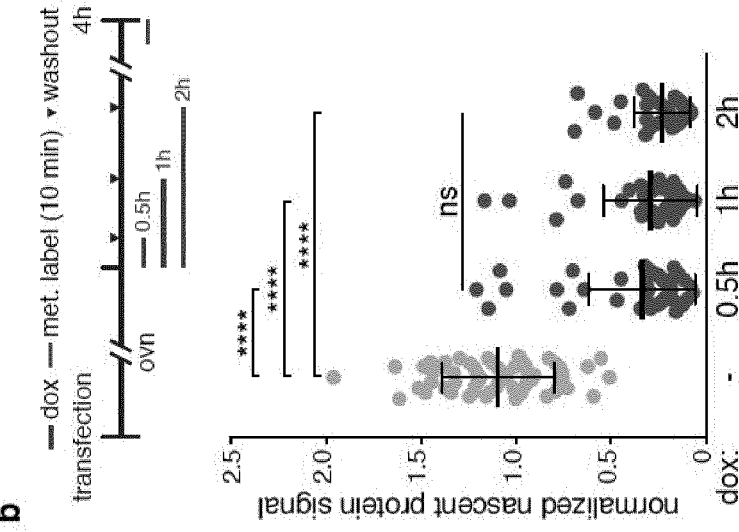
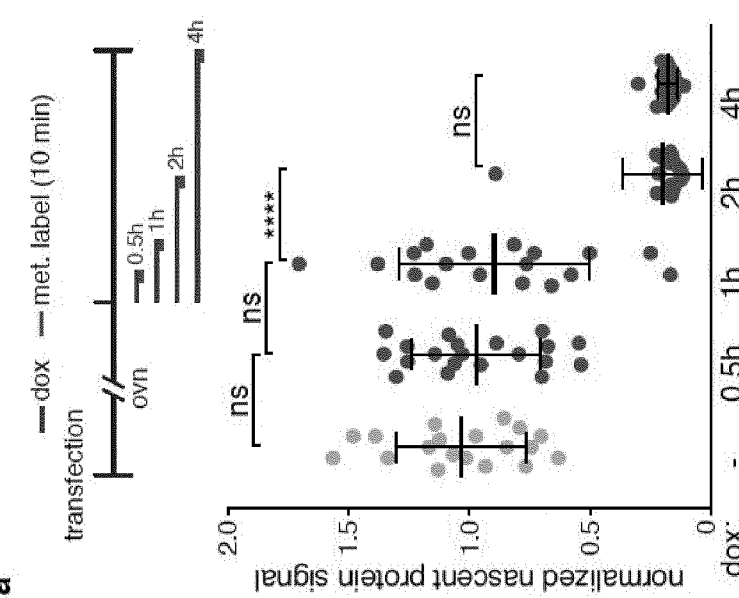
Figure 5 - Temporally-resolved protein synthesis inhibition Figure 5 (continued) – Temporally-resolved protein synthesis inhibition
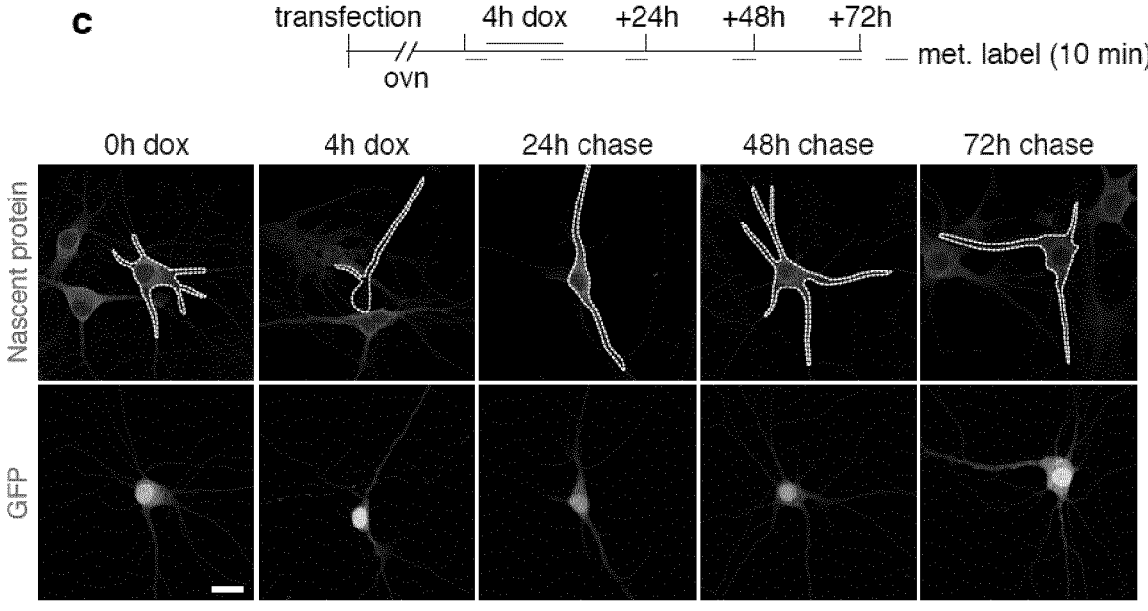
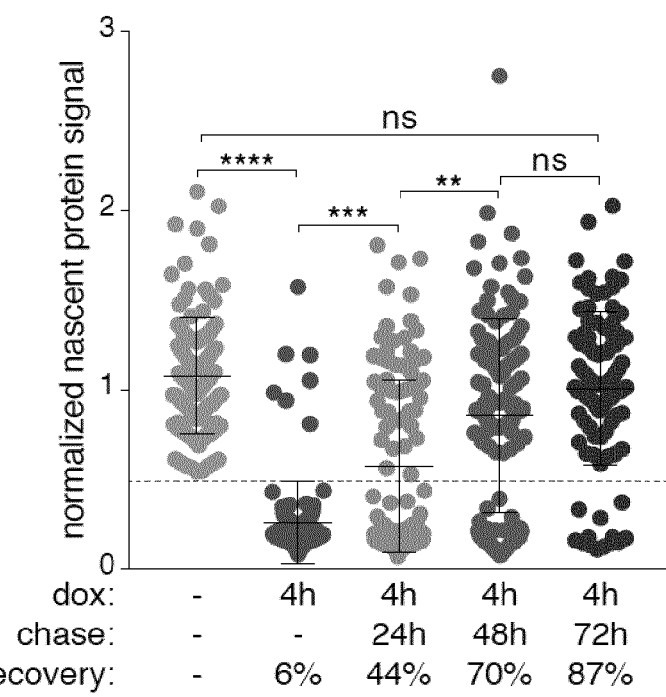

Figure 6 – Extended or enhanced gePSI expression in neurons that exhibit retarded protein synthesis recovery
a
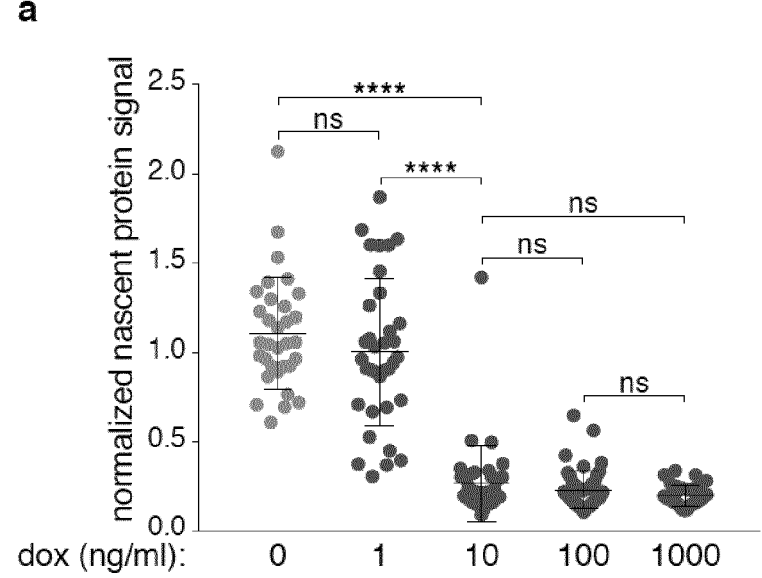
b
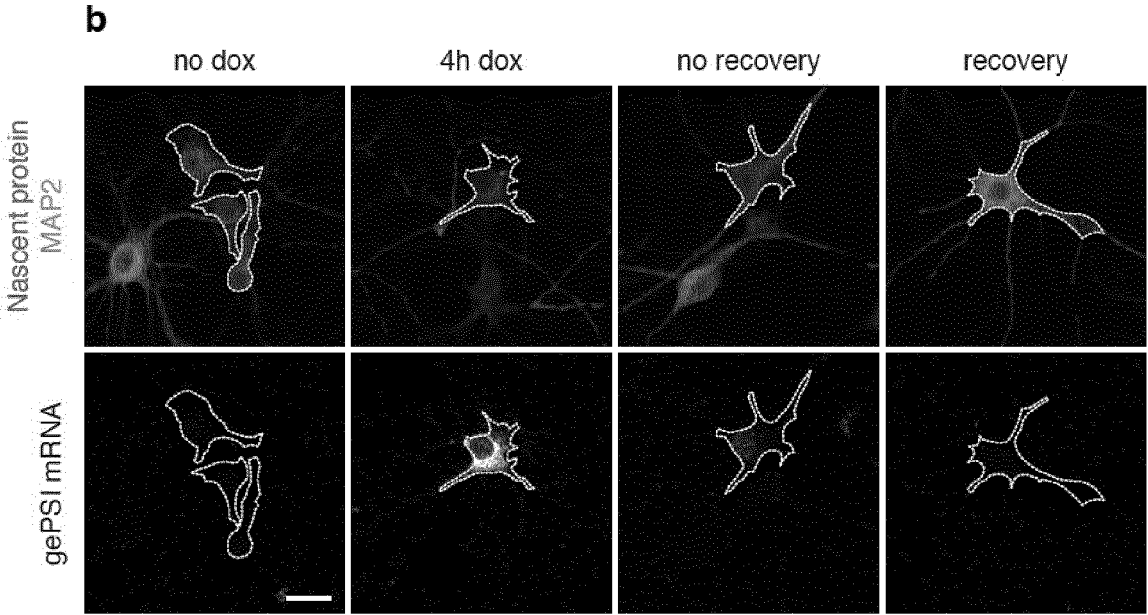

Figure 6 (continued) - Extended or enhanced gePSI expression in neurons that exhibit retarded protein synthesis recovery
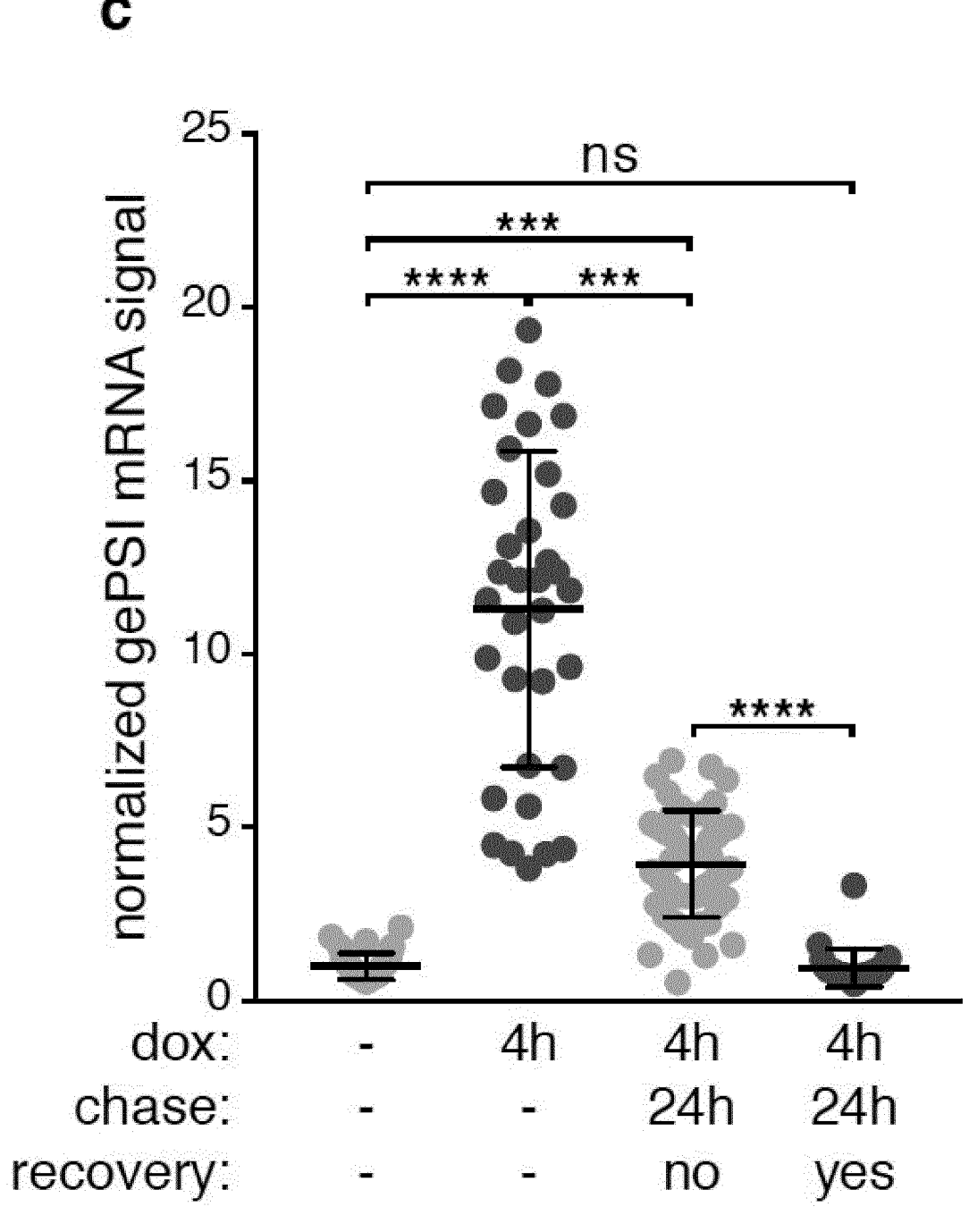

Figure 6 (continued) - Extended or enhanced gePSI expression in neurons that exhibit retarded protein synthesis recovery
d
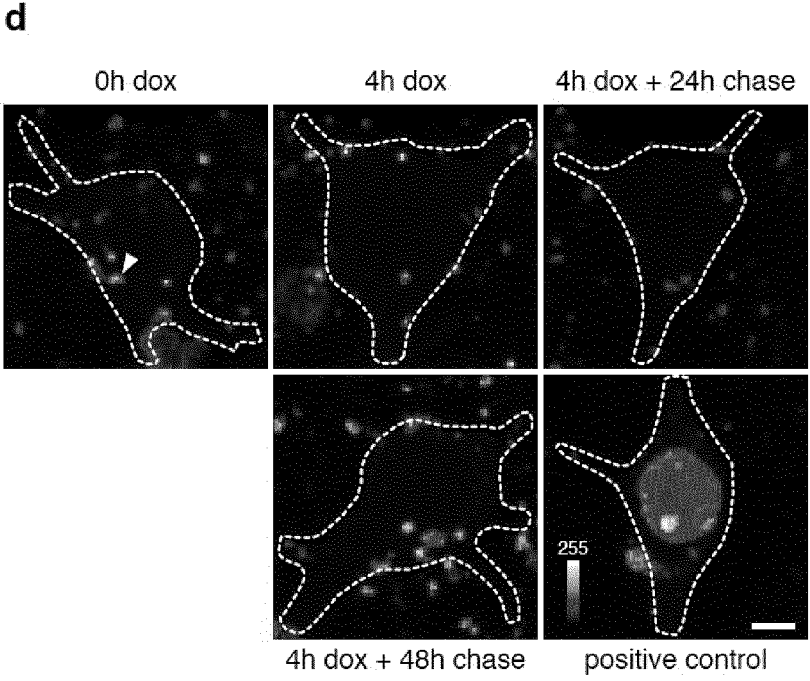
e
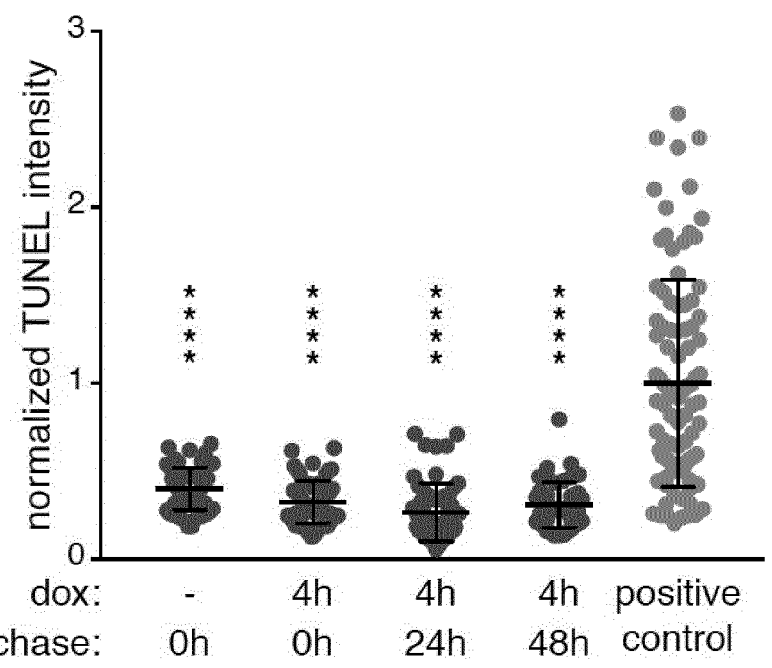

Figure 7 – Cell type-specific protein synthesis inhibition
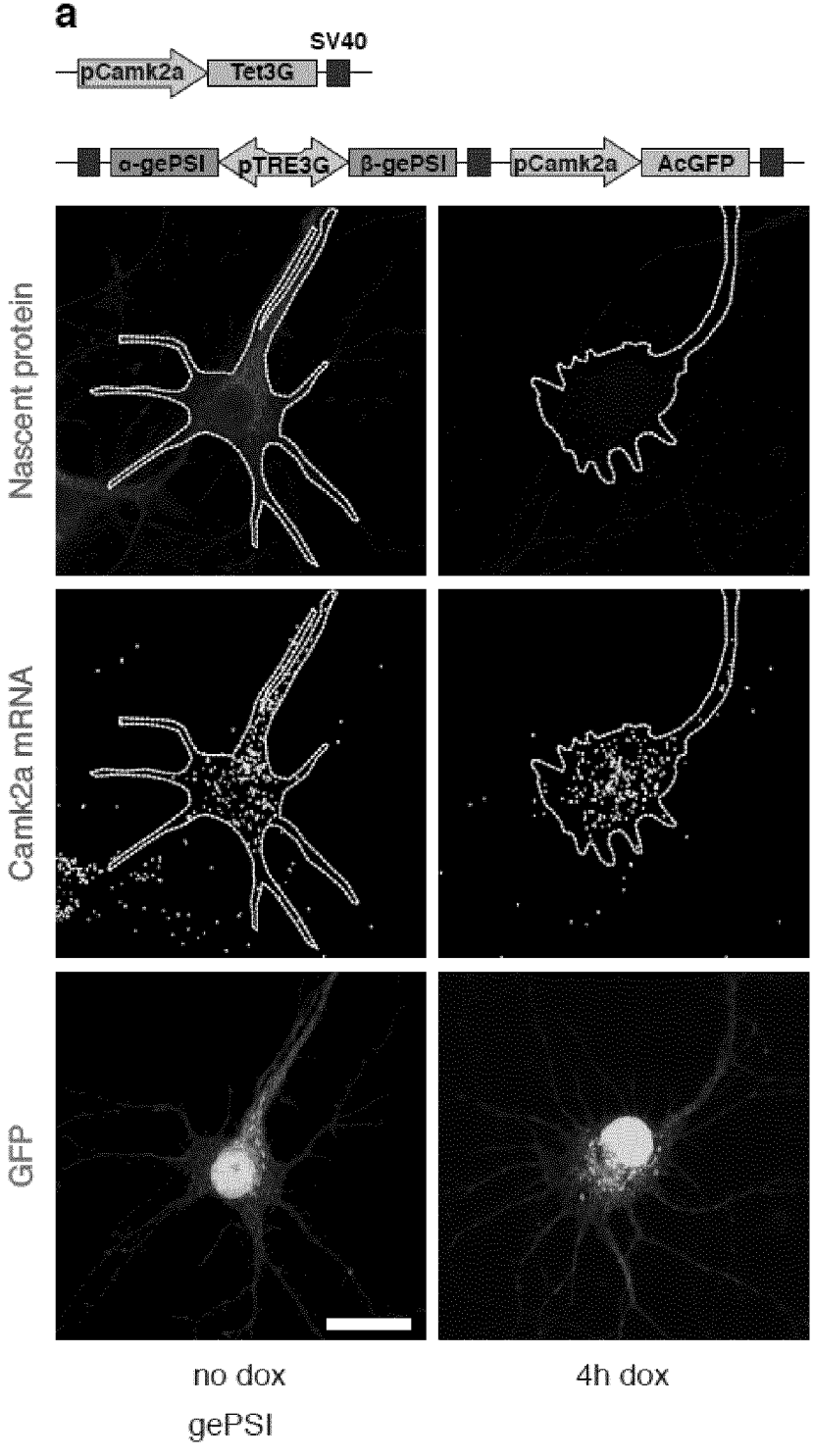

Figure 7 – Cell type-specific protein synthesis inhibition
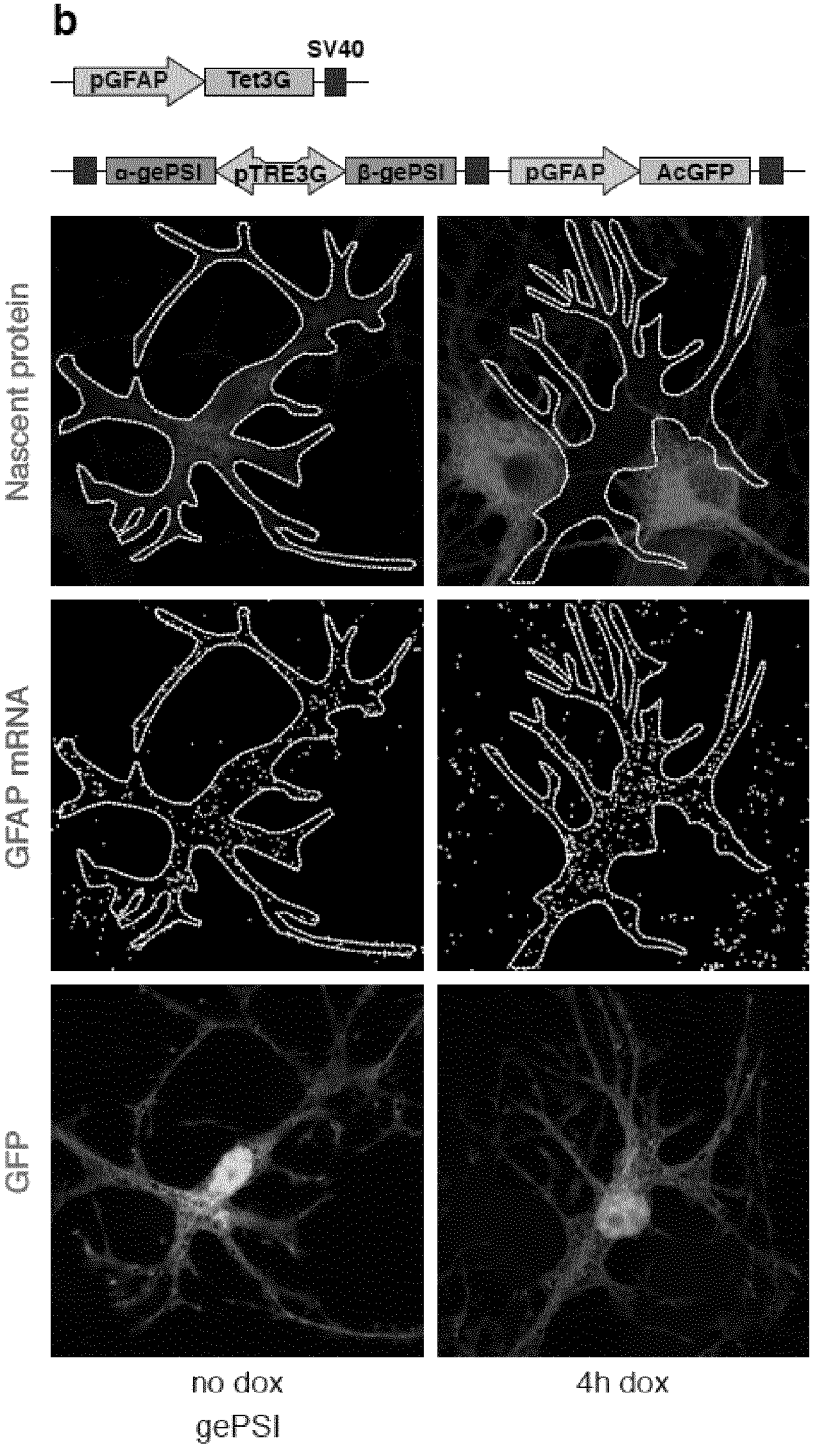

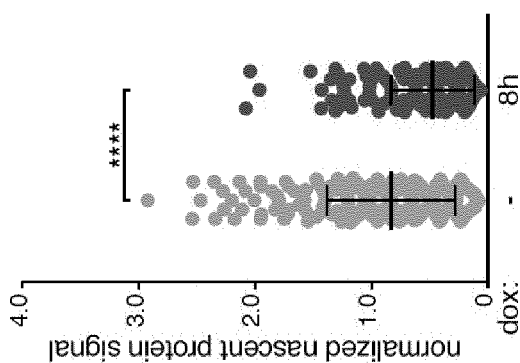
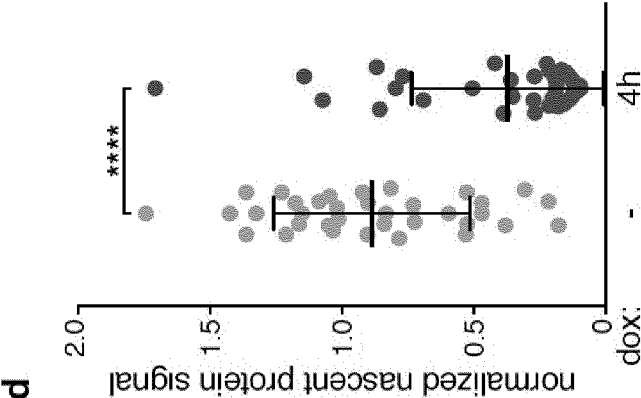
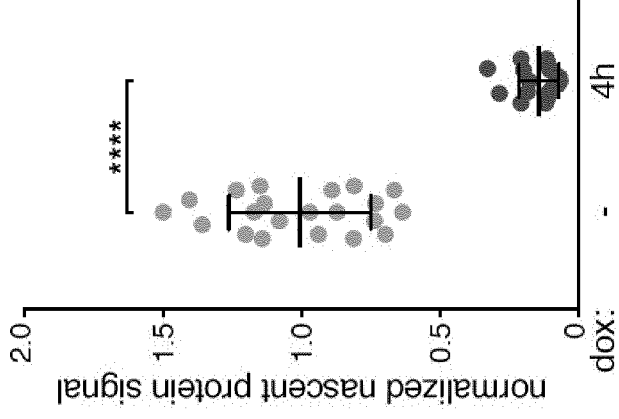
Figure 7 (continued) - Cell type-specific protein synthesis inhibition Figure 7 – Cell type-specific protein synthesis inhibition
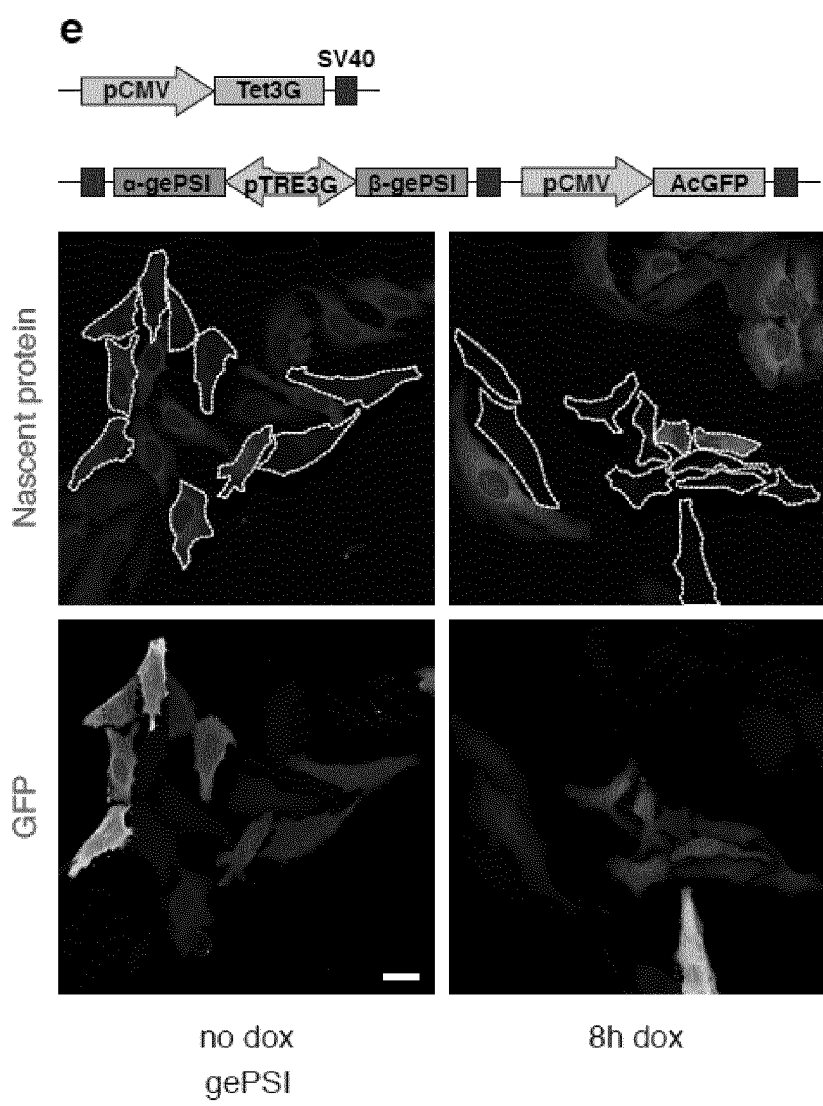

Figure 8 – Cre-dependent expression of the gePSI
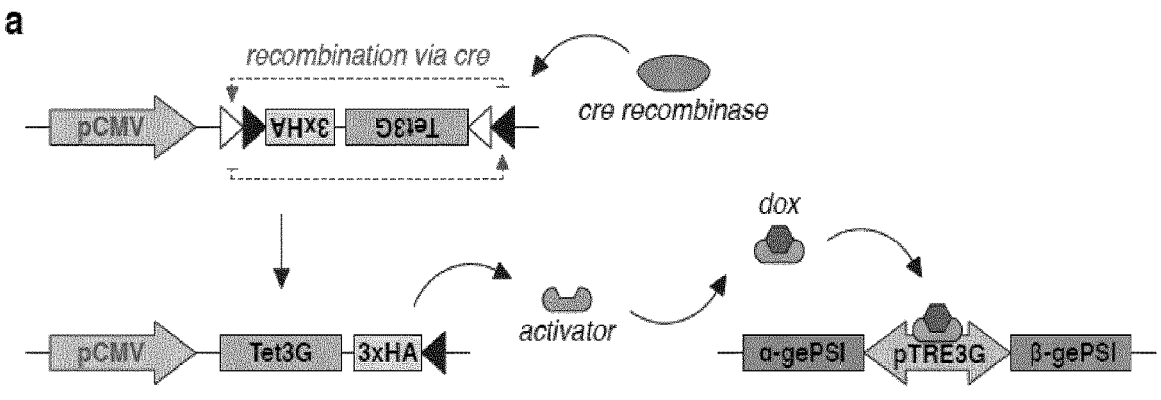
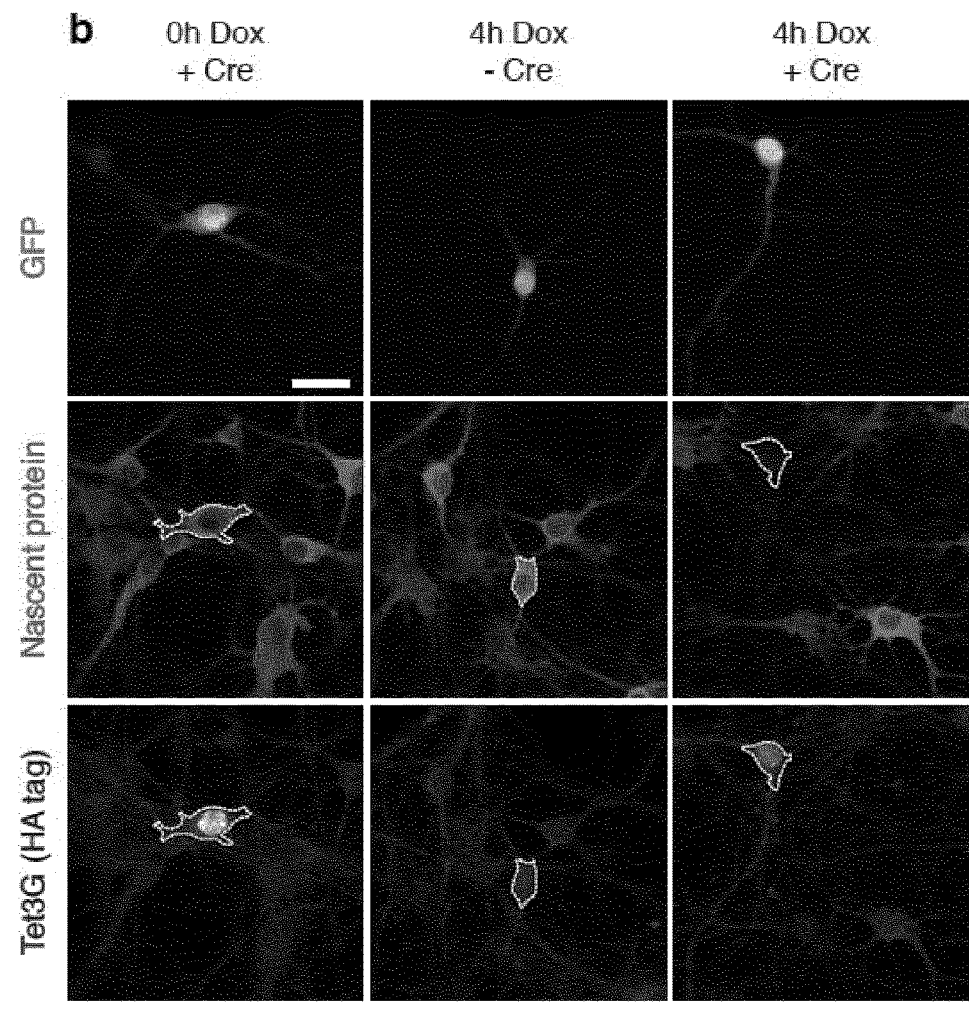

Figure 8 (continued) - Cre-dependent expression of the gePSI
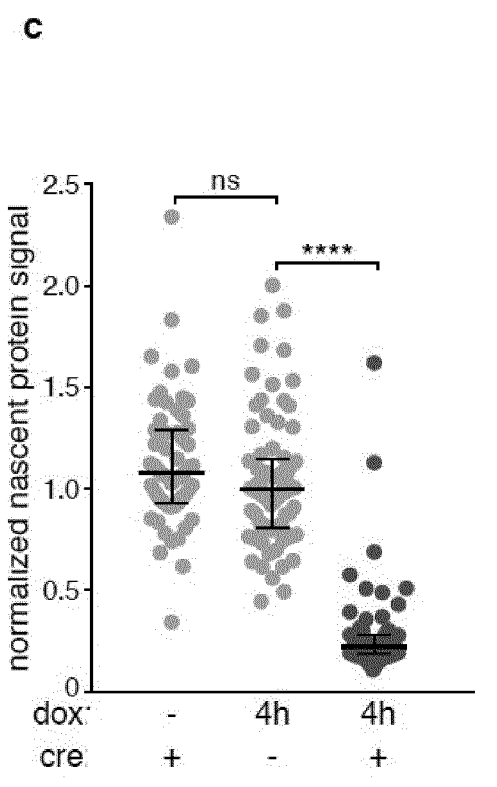
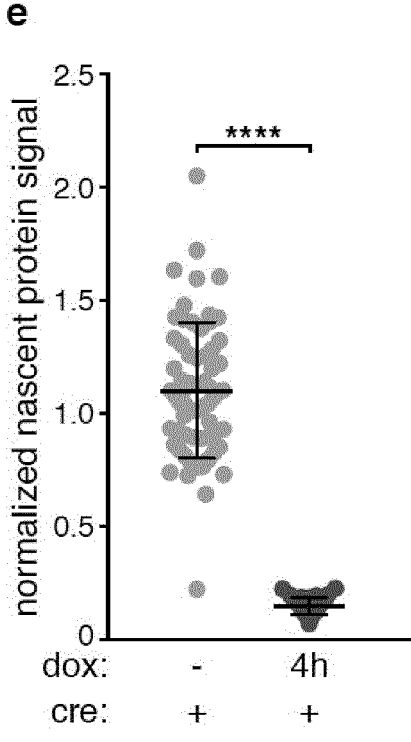

Figure 8 (continued) – Cre-dependent expression of the gePSI
d
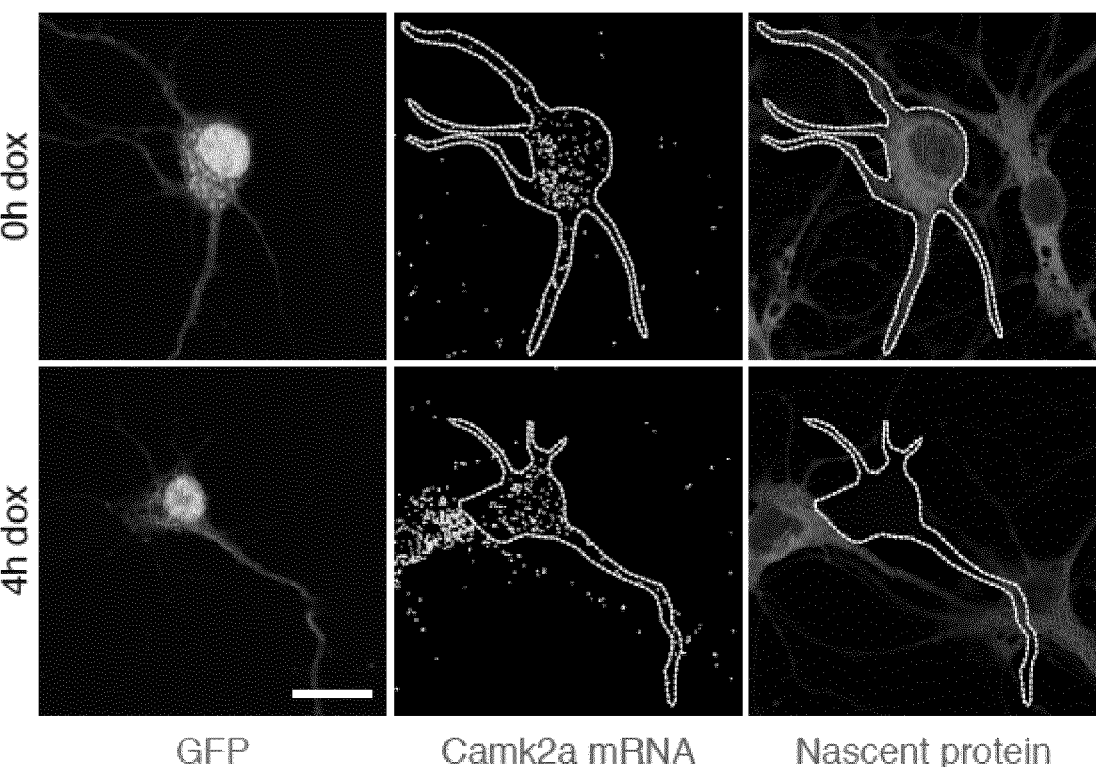
GFP          Camk2a mRNA          Nascent protein Figure 9 – gePSI induction does not perturb neuronal response but prevents spine structural plasticity
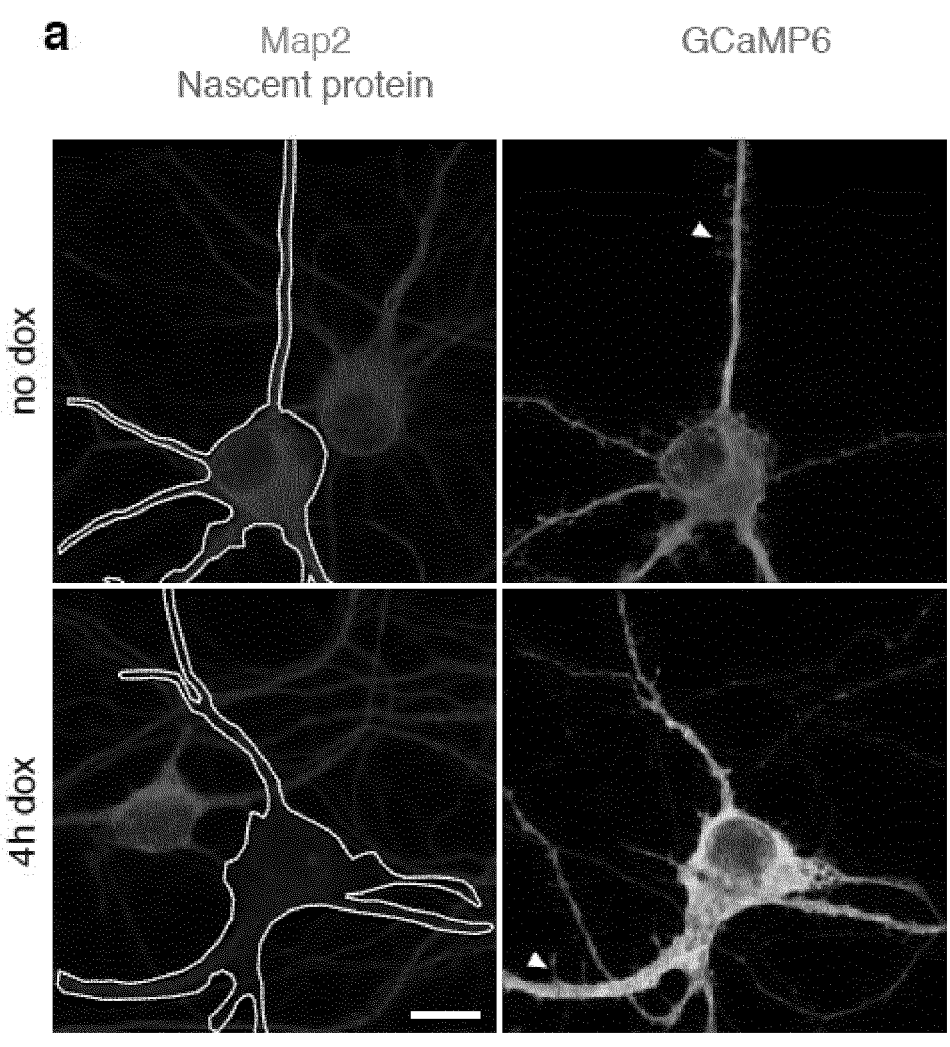

Figure 9 (continued) - gePSI induction does not perturb neuronal responses but prevents spine structural plasticity
b
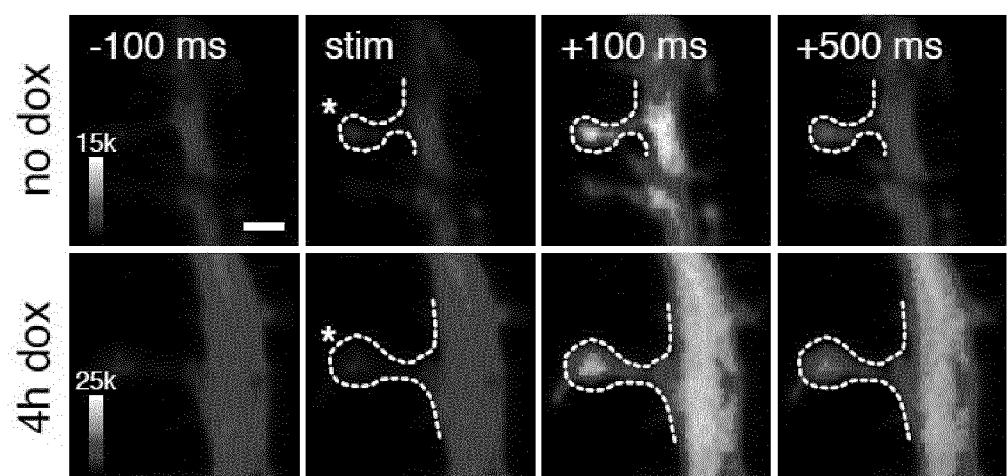
c
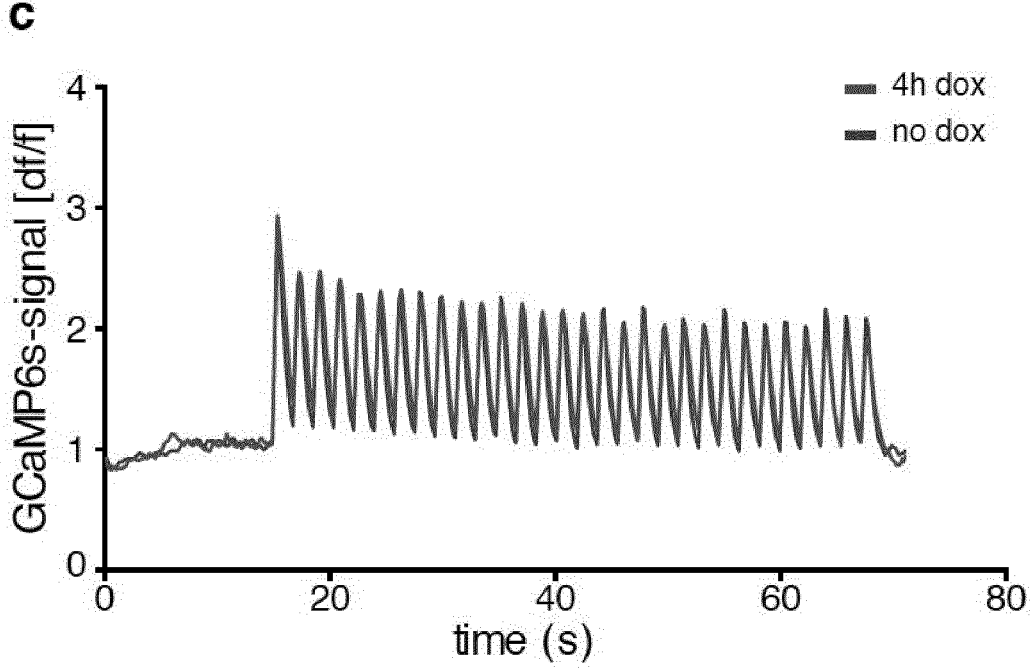

Figure 9 (continued) - gePSI induction does not perturb neuronal responses but prevents spine structural plasticity
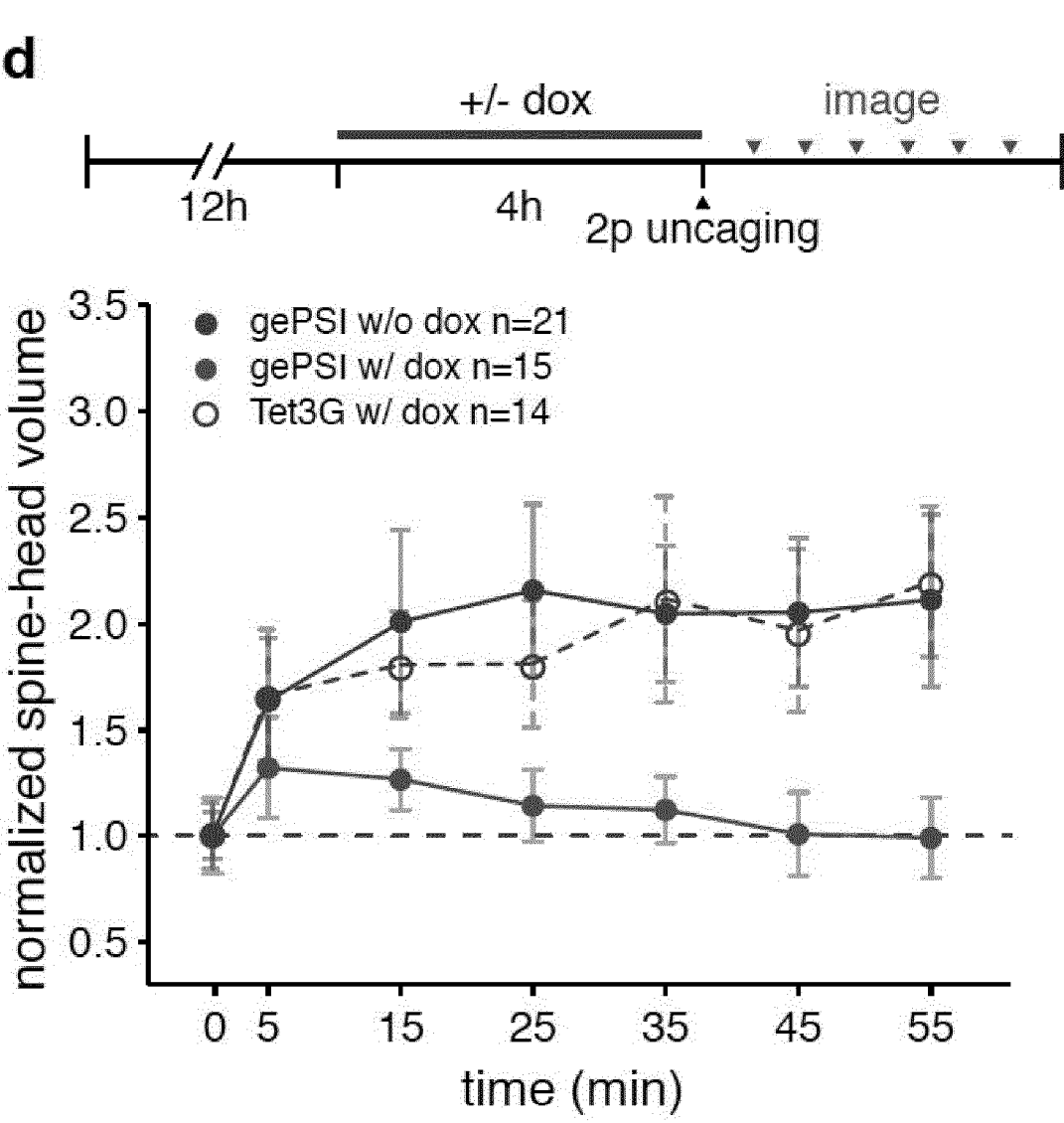

Figure 9 (continued) - gePSI induction does not perturb neuronal responses but prevents spine structural plasticity
e
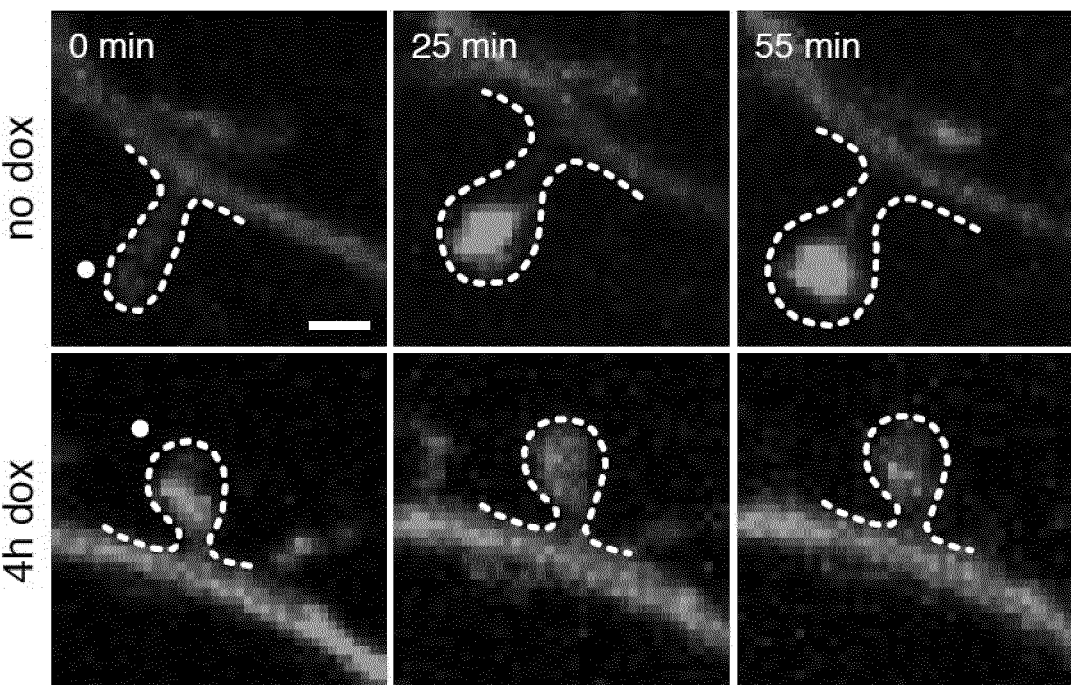

Figure 12 - First part of the ProRIP-sequence from maize.

Figure 13 - Second part of the ProRIP-sequence from maize.

Figure 14:
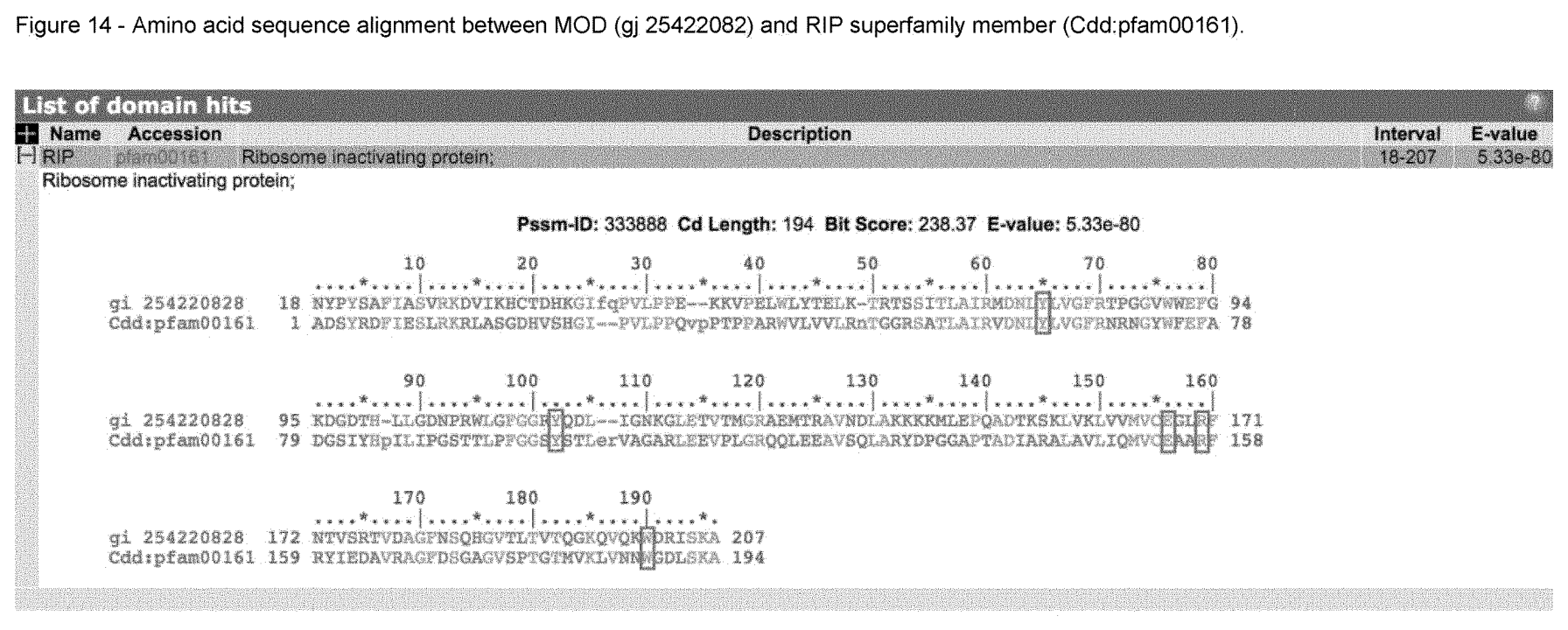

Figure 14 - Amino acid sequence alignment between MOD (gi 254220082) and RIP superfamily member (Cdd:pfam00161).

Figure 15 - Amino acid sequence alignment between MOD and different RIP family members (upper: ricin-like, middle: trichosanthin, lower: gelonin).

```
Range 1: 55 to 217 GenPept  Graphics                    ▼ Next Match  ▲ Previous Match
Score          Expect  Method                     Identities    Positives      Gaps
38.5 bits(88)  0.007   Compositional matrix adjust. 42/166(25%)  69/166(41%)  15/166(9%)

Query   21   YSAFIASVRKDVIKHCTDHKGIFQPVLPPEKKVP--ELWLYTELKTRTS-SITLAIRMDN   77
             Y AFI ++R+ ++       I  PVL     P + ++  +L  +   SITLA+ + N
Sbjct   55   YRAFINAMRRQLLTGDDVRHQI--PVLRNRVGFPINQRFVLVQLTNQAELSITLAVDVTN   112

Query   78   LYLVGFRTPGGVWWEFGKDGD------THLLGD--NPRWLGFGGRYQDLIGNKGL-ETVT   128
             Y+VG+R     ++ F D        THL  D    +   FGG Y  L    GL E +
Sbjct  113   AYVVGYRAGNNAYF-FQPDNPEDAEAITHLFTDAQTRQTFAFGGNYDRLEQLGGLRENIE   171

Query  129   MGRAEMTRAVNDLAKKKKMLEPQADTKSKLVKLVVMVCEGLRFNTV   174
             +G   +  A++ L              +  + M+ E +RF +
Sbjct  172   LGNGPLEDAISALYYYSTGGTQLPALARSFMVCIQMISEAVRFQYI   217

Query: MOD / Sbjct: ricin-like [Ricinus communis] Sequence ID: XP_002532189.1
```

```
Range 1: 37 to 194 Graphics                              ▼ Next Match  ▲ Previous Match
Score          Expect  Method                     Identities    Positives      Gaps
23.5 bits(49)  0.003   Compositional matrix adjust. 35/167(21%)  69/167(41%)  18/167(10%)

Query   21   YSAFIASVRKDVIKHCTDHK-GIFQPVLPPEKKVPELWLYTELKTRTSSITLAIRMDNLY   79
             Y  FI+++RK +      +     + +  + LP ++   + L T    T  I++AI + ++Y
Sbjct   37   YGVFISNLRKALPNERKLYDIPLLRSSLPGSQRYALVHL-TNYADET--ISVAIDVTSVY   93

Query   80   LVGFRTPGGVWWEFGKDGDT----HLLGDNPR--WLGFGGRYQDL--IGNKGLETVTMGR   131
             ++G+R  G   + F +   T     ++  D R    L +G Y+ L     K  E + +G
Sbjct   94   IMGYRA-GDTSYFFNEASATEAAKYVFKDAMRKVTLPYSGNYERLQTAAGKIRENIPLGL   152

Query  132   AEMTRAVNDLAKKKKMLEPQADTKSKLVKLVVMVCEGLRFNTVSRTV   178
             +   A+  L             S L+ L+    E  R+ + + +
Sbjct  153   PALDSAITTL-----FYYNANSAASALMVLIQSTSEAARYKFIEQQI   194

Query: MOD / Sbjct: trichosanthin [Trichosanthes kirilowii] GenBank: AA31048.1
```

```
Range 1: 112 to 230 Graphics                             ▼ Next Match  ▲ Previous Match
Score          Expect  Method                     Identities    Positives      Gaps
30.0 bits(66)  3e-05   Compositional matrix adjust. 28/119(24%)  49/119(41%)  4/119(3%)

Query   71   LAIRMDNLYLVGFRTPG-GVWWEFGKDGDTHLLGDNP--RWLGFGGRYQDLIGNKGL-ET   126
             +AI + ++Y+VG++      +++     D   L  N    L FGG Y  L G K    ET
Sbjct  112   IAIDVTSVYVVGYQVRNSYFFKDAPDAAYEGLFKNTIKTRLHFGGSYPSLEGEKAYRET   171

Query  127   VTMGRAEMTRAVNDLAKKKKMLEPQADTKSKLVKLVVMVCEGLRFNTVSRTVDAGFNSQ   185
             +G   +  + L +         + S L+ ++ MV E RF +   + F +
Sbjct  172   TDLGIEPLRIGIKKLDENAIDNYKPTEIASSLLVVIQMVSEAARFTFIENQIRNNFQQR   230

Query: MOD / Sbjct: gelonin [] UniProtKB/Swiss-Prot: P33186.2
```

GENETICALLY ENCODED PROTEIN SYNTHESIS INHIBITOR

CROSS REFERENCE TO RELATED APPLICATION

This application is a 35 U.S.C. 371 National Phase Entry Application from PCT/EP2020/064801, filed May 28, 2020, which claims the benefit of European Patent Application No. 19177622.8 filed on May 31, 2019, the disclosures of which are incorporated herein in their entirety by reference.

The instant application contains a Sequence Listing which has been submitted via EFS-Web and is hereby incorporated by reference in its entirety. Said Sequence Listing, created on May 25, 2020, is named D00-25.05.2020_Sequence_Listing.TXT and is 29 kilobytes in size.

The present invention relates to an expression system for a genetically encoded protein synthesis inhibitor containing RNA N-glycosidase activity split into two components. The expression system can be combined with genetic targeting systems to achieve cell- and/or tissue-type-specific and/or temporally-specific control of protein synthesis in a host, particularly in a mammalian host.

BACKGROUND

Proteins are the main functional unit within cells that control biological processes. In all cells, protein synthesis is used to respond to extra- and/or intracellular cues to remodel cellular function. In the brain protein synthesis is crucial for some forms and specific temporal phases of synaptic plasticity[1]. Previous studies probing the role of protein synthesis have used chemical inhibitors, often common antibiotics, which are effective but lack functional and cell type specificity.

Ribosome-inactivating proteins (RIPs) are known genetically encoded protein synthesis inhibitors[2,3]. They form a family of well-characterized toxins, which specifically and irreversibly inhibit protein synthesis in eukaryotic cells by enzymatically altering the 28S rRNA of the large 60S ribosomal subunit leading to the abolition of the interaction between the large 60S ribosomal subunit and translation elongation factor 2. RIPs act at low doses because their catalytic activities allow complete inactivation of ribosomes and protein synthesis at a less-than-equimolar ratio to their substrate. RIPs display rRNA N-glycosidase activity (EC 3.2.2.22) and depurinate 28S rRNA by cleaving the bond between adenine and ribose in the sarcin-ricin loop of the molecule, thus preventing regroupment of translation elongation factors in subsequent protein synthesis.

A large number of RIPs have been isolated from various species of plants and bacteria with varying degrees of toxicity. These RIPs have been subdivided into several categories. Class 1 RIPs are monomeric proteins of approximately 30 kDa which possess RNA N-glycosidase enzymatic activity. In contrast, class 2 RIPs are composed of an A-chain with RNA N-glycosidase activity wherein said A-chain is associated to one or several B-chains of approximately 35 kDa. The B-chain is a lectin-like peptide that has strong affinity for sugar moieties displayed in the surface of cells and helps promote translocation through the plasma membrane. Class 3 RIPs (or sometimes called atypical class 1 RIPs) are monomeric proteins and synthesized as an inactive precursor (ProRIP) that is proteolytically converted into a functional toxin which is a complex of two subunits each of which alone lacks RNA N-glycosidase activity.

The use of RIPs as protein synthesis inhibitors for molecular-biological, physiological or pharmaceutical studies, however, has been hampered, since their administration to eukaryotic cells leads to an irreversible inhibition of protein synthesis.

Thus, it is an object of the present invention to overcome these disadvantages and provide a genetically encoded protein synthesis inhibitor which allows temporal and/or spatial control of protein synthesis in a eukaryotic host.

SUMMARY OF THE INVENTION

The present inventors have developed an expression system for a genetically encoded protein synthesis inhibitor, which is a modified RIP. The experiments were carried out using an atypical class 1 RIP from maize (*Zea mays*). Direct expression of the inactive precursor (ProRIP) encoded by a single nucleic acid sequence in cultured hippocampal neurons resulted in a complete shutdown of protein synthesis in a majority of the cells. Expression of the RIP α-chain and the RIP β-chain encoded by separate nucleic acid sequences, however, provided spatial and temporal control of protein synthesis inhibition. Surprisingly, the cells even exhibited functional recovery of protein synthesis capabilities.

A first aspect of the present invention relates to an expression system for a genetically encoded protein synthesis inhibitor having RNA N-glycosidase activity, comprising (a) a first nucleic acid sequence encoding a first component of the protein synthesis inhibitor in operative linkage with a first expression control sequence, and (b) a second nucleic acid sequence encoding a second component of the protein synthesis inhibitor in operative linkage with a second expression control sequence, wherein the expression system is adapted for expressing the first nucleic acid sequence and the second nucleic acid sequence separate from each other, wherein the first component and the second component together form a complex having RNA N-glycosidase activity, and wherein the first component alone and the second component alone lack RNA N-glycosidase activity.

A further aspect of the present invention relates to a host, e.g. a cell or a non-human organism, comprising an expression system as described above.

Still a further aspect of the present invention is a method of inhibiting protein synthesis in a host, comprising the steps:

(i) introducing an expression system as described above into the host, and (ii) expressing in the host a functional protein synthesis inhibitor encoded by the expression system whereby protein synthesis is inhibited in the host or in a part thereof.

Still a further aspect of the present invention is a kit for providing expression of a genetically encoded protein synthesis inhibitor having N-glycosidase activity in a host, comprising:

(a) a first nucleic acid sequence encoding a first component of the protein synthesis inhibitor in operative linkage with a first inducible expression control sequence, (b) a second nucleic acid molecule encoding a second component of the protein synthesis inhibitor in operative linkage with a second inducible expression control sequence,

3 wherein the first nucleic acid sequence and the second nucleic acid sequence are provided for expression separate from each other, wherein the first component and the second component together form a complex having RNA N-glycosidase activity, and wherein the first component alone and the second component alone lack RNA N-glycosidase activity, (c) optionally a cell- and/or tissue-type specific expression control sequence in operative linkage with a third nucleic acid sequence responsible for restricting expression of (a) and (b) to a targeted cell and/or tissue, and (d) optionally means for inducing expression of the first nucleic acid sequence (a) and expression of the second nucleic acid sequence (b).

The expression system or host as described above can be used in basic research, e.g. for the cell- and/or tissue-type specific inhibition of protein synthesis and/or for reversible inhibition of protein synthesis in a eukaryotic host, particularly in a mammalian host. Further, the expression system and the host can be used in screening procedures or in medicine, e.g. in the treatment of cancer or in the treatment of neurological disorders.

DETAILED DESCRIPTION

The present invention particularly relates to the following items, which are part of the description:

1. An expression system for a genetically encoded protein synthesis inhibitor having RNA N-glycosidase activity, comprising (a) a first nucleic acid sequence encoding a first component of the protein synthesis inhibitor in operative linkage with a first expression control sequence, and (b) a second nucleic acid sequence encoding a second component of the protein synthesis inhibitor in operative linkage with a second expression control sequence, wherein the expression system is adapted for expressing the first nucleic acid sequence and the second nucleic acid sequence separate from each other, wherein the first component and the second component together form a complex having RNA N-glycosidase activity, and wherein the first component alone and the second component alone lack RNA N-glycosidase activity.

2. The system of item 1 wherein the first component and the second component form a functional enzyme or a part thereof wherein the functional enzyme exerts its RNA N-glycosidase activity by depurinating an adenine on the sarcin-ricin loop of the 28S rRNA located on the large 60S subunit of a eukaryotic ribosome.

3. The system of item 1 or 2, wherein the first component comprises an α-chain from a class 3 ribosome-inactivating protein (RIP), particularly an α-chain from a Panicoideae RIP, more particularly a maize RIP α-chain, or a functional variant thereof, and/or wherein the second component comprises a β-chain from a class 3 ribosome-inactivating protein (RIP), particularly a β-chain from a Panicoideae RIP, more particularly a maize RIP β-chain, or a functional variant thereof.

4. The system of any one of items 1-3, wherein the first nucleic acid sequence and the second nucleic acid sequence have different transcriptional starting points.

5. The system of any one of items 1-4, wherein (i) the first expression control sequence and the second expression control sequence are separate from each other, or wherein (ii) the first expression control sequence and the second expression control sequence are combined in a single bi-directional expression control sequence.

6. The system of any one of items 1-5, wherein the first component comprises an amino acid sequence selected from:

(a) the amino acid sequence shown in SEQ ID NO. 1;

(b) an amino acid sequence having an identity of at least 50%, 60%, 75%, 80%, 85%, 90%, 95%, 96%, 97%, 98% or 99% to the amino acid sequence of (a); and (c) an amino acid sequence which is a functional variant of the amino acid sequence of (a) and/or (b).

7. The system of any one of items 1-6, wherein the second component comprises an amino acid sequence selected from:

(a) the amino acid sequence shown in SEQ ID NO. 2;

(b) an amino acid sequence having an identity of at least 50%, 60%, 75%, 80%, 85%, 90%, 95%, 96%, 97%, 98% or 99% to the amino acid sequence of (a); and (c) an amino acid sequence which is a functional variant of the amino acid sequence of (a) and/or (b).

8. The system of any one of items 1-7, wherein the first expression control sequence and/or the second expression control sequence are inducible expression control sequences.

9. The system of item 8, wherein the first and/or second expression control sequences are inducible by temperature shift, by light, by addition or removal of one or more chemical substances (e.g. of synthetic or biological origin) or by any combination thereof.

10. The system of item 8 or 9, wherein the inducible expression control sequences are chosen from tetracycline-controlled expression control sequences, hormone-controlled expression control sequences, light-controlled expression control sequences, and/or heat-shock expression control sequences.

11. The system of any one of items 1-10, further comprising:

(c) a third nucleic acid sequence encoding a regulator, e.g. an activator for the first and/or second expression control sequence in operative linkage with a third expression control sequence.

12. The system of item 11, wherein the third expression control sequence is a cell- and/or tissue-type specific expression control sequence, in particular a cell- and/or tissue-type specific expression control sequence inducible by an external stimulus.

13. The system of any one of items 11-12,
  wherein the third expression control sequence is an expression control sequence specific for cells from brain tissue or specific for cells forming pre-cancerous or cancerous tissue.
14. The system of any one of items 1-13,
  which is inducible by a site-specific recombinase, e.g. a Cre recombinase.
15. The system of any one of items 1-14,
  which is a viral expression system.
16. The system of any one of items 1-14,
  which is a non-viral expression system, e.g. encoded on at least one plasmid vector.
17. The system of item 15 or 16,
  which is adapted for direct extrachromosomal expression and/or for chromosomal integration and expression.
18. The system of any one of items 1-17,
  which provides spatial and/or temporal expression control, particularly spatial and temporal expression control for the protein synthesis inhibitor.
19. A host comprising an expression system of any one of items 1-18.
20. The host of item 19,
  which is transfected, transformed or transduced with the expression system.
21. The host of item 19 or 20,
  which is an isolated cell, a cell preparation, a cell culture, an organoid, a tissue or an organ, particularly of mammalian origin, and more particularly of human origin.
22. The host of item 19 or 20,
  which is a non-human organism, particularly of mammalian origin.
23. The host of any one of items 19-22,
  wherein the expression system provides spatial and/or temporal expression control, particularly spatial and temporal expression control for the protein synthesis inhibitor in the host.
24. The host of any one of items 19-23,
  wherein the expression system provides a reversible inhibition of protein synthesis in the host.
25. A method of inhibiting protein synthesis in a host, comprising the steps:
  (i) introducing an expression system of any one of items 1-17 into the host, and
  (ii) expressing in the host a functional protein synthesis inhibitor encoded by the expression system whereby protein synthesis is inhibited in the host or in a part thereof.
26. The method of item 25,
  wherein expression of the functional protein synthesis inhibitor is under spatial and/or temporal control, particularly under spatial and temporal control.
27. The method of item 25 or 26,
  wherein expression of the functional protein synthesis inhibitor is a cell- and/or tissue-specific expression.
28. The method of any one of items 25-27,
  wherein expression of the functional protein synthesis inhibitor is reversible.
29. The method of any one of items 25-28,
  wherein expression of the functional protein synthesis inhibitor is under conditions providing a subsequent recovery of protein synthesis in the host.
30. An expression system of any one of items 1-18 for use in medicine.
31. A host of any one of items 19-24 for use in medicine.

32. The expression system of item 30 or the host of item 31 for the use in the treatment of cancer or in the treatment of neurological disorders, e.g. for the treatment of Fragile X syndrome.
33. Use of an expression system of any one of items 1-18, or a host of any one of items 18-23 for a cell- and/or tissue-type specific inhibition of protein synthesis and/or for a reversible inhibition of protein synthesis in a eukaryotic host, particularly in a mammalian host.
34. Use of an expression system of any one of items 1-18, or a host of any one of items 18-23 for a screening procedure.
35. The use of item 31 for drug screening, e.g. for screening for agents against neurological disorders or for agents against cancer.
36. A kit for providing expression of a genetically encoded protein synthesis inhibitor having N-glycosidase activity in a host, comprising:
  (a) a first nucleic acid sequence encoding a first component of the protein synthesis inhibitor in operative linkage with a first inducible expression control sequence,
  (b) a second nucleic acid molecule encoding a second component of the protein synthesis inhibitor in operative linkage with a second inducible expression control sequence,
    wherein the first nucleic acid sequence and the second nucleic acid sequence are provided for expression separate from each other,
    wherein the first component and the second component together form a complex having RNA N-glycosidase activity, and
    wherein the first component alone and the second component alone lack RNA N-glycosidase activity,
  (c) optionally a cell- and/or tissue-type specific expression control sequence in operative linkage with a third nucleic acid sequence responsible for restricting expression of (a) and (b) to a targeted cell and/or tissue, and
  (d) optionally means for inducing expression of the first nucleic acid sequence (a) and expression of the second nucleic acid sequence (b).

The present invention relates to a system for expressing a genetically encoded protein synthesis inhibitor (gePSI) having RNA N-glycosidase activity in a host, particularly in a eukaryotic host. The expression system can be any suitable type of eukaryotic expression system, e.g. a viral expression system or a non-viral expression system, e.g. a plasmid-based expression system. The expression system may be adapted for direct extrachromosomal expression and/or for chromosomal integration and chromosomal expression. The expression system may be suitable for providing expression in any type of eukaryotic host, e.g. an animal host such as a vertebrate host, particularly a mammalian host, or an insect host, a plant host or a fungal host, preferably a mammalian host.

The expression system comprises a plurality of nucleic acid sequences, which may be single- or double stranded nucleic acid, e.g. DNA and/or RNA sequences. In particular, the expression system comprises a first nucleic acid sequence encoding a first component of a protein synthesis inhibitor in operative linkage with a first expression control sequence, a second nucleic acid sequence encoding a second component of a protein synthesis inhibitor in operative linkage with a second expression control sequence, and optionally a third nucleic acid sequence encoding a regulator, e.g. an activator, for the first and/or second expression control sequence, particularly an activator for both the first and second expression control sequence in operative linkage with a third expression control sequence. The codon usage in the protein-coding sequences may be adapted, e.g. optimized for expression in the respective host. The expression control sequences typically are adapted for expression in the respective host and may comprise promoter and transcription regulation sequence elements, particularly inducible transcription regulation elements and/or cell- and/or tissue-type-specific transcription regulation elements. In addition to the above sequences, the expression system may comprise further sequences, e.g. propagation, replication and/or integration sequences and/or selection marker sequences.

The nucleic acid sequences constituting the expression system may be present on a single expression vehicle, e.g. a viral or non-viral vector, or on a plurality of two or more expression vehicles, e.g. viral or non-viral vectors. For example, the expression system may comprise at least two separate expression vehicles, wherein the first nucleic acid sequence and the second nucleic acid sequence are located on a first vehicle, e.g. a first plasmid, and the third nucleic acid sequence is located on a second vehicle, e.g. a second plasmid.

The expression system is adapted for separate expression of the first nucleic acid sequence and the second nucleic acid sequence. This results in the direct production of two separate expression products, i.e. without any previous proteolytic cleavage. Thus, the direct expression products, i.e. the polypeptides encoded by the first or second nucleic acid sequence, respectively, are not covalently linked to each other. The first polypeptide is a first component of a protein synthesis inhibitor and the second polypeptide is a second component of a protein synthesis inhibitor, wherein the first component and the second component together form a complex, in particular a dimeric complex having RNA N-glycosidase activity. The first component alone and the second component alone, however, are devoid of RNA N-glycosidase activity, e.g. assessed by measuring the translational activity of transfected cells. Neuronal cells transfected with either the first or second component show normal levels of translation as shown by metabolic labeling (see Example 1, FIG. 2*b-e*).

In certain embodiments, the first nucleic acid sequence and/or the second nucleic acid sequence may comprise sequence portions encoding heterologous protein domains resulting in the expression of a fusion polypeptide comprising the first component of the protein synthesis inhibitor fused to a heterologous polypeptide domain and/or the second component of the protein synthesis inhibitor fused to a heterologous polypeptide domain. Heterologous polypeptide domains, if present, may be fused to the N- and/or C-terminus of the first component or the second component, respectively.

In certain embodiments, the first nucleic acid sequence and the second nucleic acid sequence have different transcriptional starting points. In certain embodiments, the first expression control sequence and the second expression control sequence are separate from each other, i.e. the first expression control sequence does not control the expression of the second nucleic acid molecule and the second expression control sequence does not control the expression of the first nucleic acid sequence. In certain embodiments, the first expression control sequence and the second expression control sequence may be combined in a single bi-directional expression control sequence.

The first component and the second component of the protein synthesis inhibitor may form a functional enzyme or a functional part thereof, wherein the functional enzyme or functional part thereof has RNA N-glycosidase activity resulting in an inhibition of eukaryotic protein synthesis. In certain embodiments, the functional enzyme exerts its RNA N-glycosidase activity by depurinating an adenine in the sarcin-ricin loop of the 28S rRNA located on the large 60S subunit of a eukaryotic ribosome. In certain embodiments, the inhibition of the protein synthesis is reversible, i.e. the protein synthesis is only inhibited for a certain period of time, and subsequently starts again.

In certain embodiments, the protein synthesis inhibitor of the present invention is a polypeptide complex comprising a first component and a second component non-covalently bound to each other wherein the first and second component together have RNA N-glycosidase activity and wherein the individual components lack RNA N-glycosidase activity. In particular, some of the amino acids constituting the catalytically active center of the protein synthesis inhibitor are present on the first component and some of the amino acids constituting the catalytically active center of the protein synthesis inhibitor are present on the second component.

The first component and the second component may be derived from class 1 RIPs, class 2 RIPs or class 3 RIPs. In certain embodiments, the protein synthesis inhibitor is a modified class 1 RIP. Native class 1 RIPs are monomeric proteins. According to the present invention, a class 1 RIP is split into two components wherein the first component alone and the second component alone lack activity, and wherein the first component and the second component together form a non-covalent complex having RNA N-glycosidase activity. In certain embodiments, the protein synthesis inhibitor of the present invention is a modified class 2 RIP. Native class 2 RIPs can consist of multiple subunits, wherein one subunit (referred to as chain A) is the subunit with RNA N-glycosidase activity (similar to a class 1 RIP), and the other chain(s) (referred to as chain(s) B) are subunit(s) that are associated with chain A and promote translocation through the plasma membrane. According to the present invention, the chain A of a class 2 RIP is split into two components wherein the first component alone and the second component alone lack RNA N-glycosidase activity and wherein the first component and the second component together form a non-covalent complex having RNA N-glycosidase activity.

In particular embodiments, the protein synthesis inhibitor of the present invention is a modified class 3 RIP. Native class 3 RIPs (or sometimes called atypical class 1 RIPs) are monomeric proteins encoded by a single nucleic acid sequence. They are synthesized as an inactive precursor that is proteolytically converted into a functional toxin which is a complex of two subunits (referred to as α-chain and β-chain) each of which alone lacks RNA N-glycosidase activity. According to the present invention, the nucleic acid sequence encoding the class 3 RIP is split into two separate sequences which are separately expressed, e.g. by operative linkage to separate expression control sequences. Examples of such class 3 RIPs are, e.g., maize (*Zea mays*) or other members of the subfamily Panicoideae such as *Z. mays parviglumis, Z. luxurians, Z. mays mexicana, T. dactyloides*, or *S. bicolor* as described in the literature[5]. Thus, in certain embodiments, the first component comprises an α-chain from a Panicoideae RIP, particularly a maize RIP α-chain, or a functional variant thereof, and/or the second component comprises a β-chain from a Panicoideae RIP, particularly a maize RIP β-chain, or a functional variant thereof. The term "functional variant" in this context relates to modified α- and β-chains which have RNA N-glycosidase activity (e.g. assessed by measuring the translational activity of transfected cells with metabolic labeling) wherein non-essential amino acids, i.e. amino acids or amino acid stretches which are not essential for the catalytic activity are deleted and/or substituted, and/or wherein heterologous amino acids or amino acid stretches are inserted. In certain embodiments, a functional variant has at least 10%, 20%, 30%, 40%, 50%, 60%, 70%, 80% or 90% RNA N-glycosidase activity of a protein synthesis inhibitor which is a complex of the α-chain shown in SEQ ID. NO. 1 and of the β-chain shown in SEQ ID. NO. 2.

In certain embodiments, the first component comprises an amino acid sequence selected from:

(a) the amino acid sequence shown in SEQ ID NO. 1;

(b) an amino acid sequence having an identity of at least 50%, 60%, 75%, 80%, 85%, 90%, 95%, 96%, 97%, 98% or 99% to the amino acid sequence of (a); and (c) an amino acid sequence which is a functional variant of the amino acid sequence of (a) and/or (b).

In certain embodiments, the second component comprises an amino acid sequence selected from:

(d) the amino acid sequence shown in SEQ ID NO. 2;

(e) an amino acid sequence having an identity of at least 50%, 60%, 75%, 80%, 85%, 90%, 95%, 96%, 97%, 98% or 99% to the amino acid sequence of (d); and (f) an amino acid sequence which is a functional variant of the amino acid sequence of (d) and/or (e).

SEQ ID NO. 1 shows the amino acid sequence of a maize RIP α-chain as used by the present inventors. SEQ ID NO. 2 shows the amino acid sequence of a maize RIP β-chain as used by the present inventors.

Amino acid identity may be determined by standard methods, e.g. the BLAST algorithm as described in the literature (Altschul et al., J. Mol. Biol. 215, 1990, 403-410).

The expression system of the invention provides expression of a protein synthesis inhibitor in a host, particularly in a eukaryotic host, e.g. an animal host such as a vertebrate, particularly mammalian, or insect host, a plant host or a fungal host. Thus, a further aspect of the invention relates to a host comprising the expression system as described above. Introduction of the expression system into the host may be carried out by conventional methods of nucleic acid transfer. For example, the host may be transfected, transformed or transduced with the expression system which may comprise a single expression vehicle or a plurality of different expression vehicles. The nucleic acid sequences containing the constituents of the expression system may be present as extrachromosomal elements and/or may be integrated into the host chromosome.

In certain embodiments, the host may be an isolated cell, a cell preparation, a cell culture, an organoid, a tissue or an organ, particularly of mammalian origin, and more particularly of human origin. In certain embodiments, the host may be a non-human organism, particularly a mammalian organism, e.g. a rodent such as a mouse, rat, hamster etc., an insect such as *Drosophila*, a fish such as zebrafish.

In certain embodiments, the expression system provides spatial and/or temporal expression control, particularly spatial and temporal expression control for the genetically encoded protein synthesis inhibitor in a host. The term "spatial control" means that expression of the protein synthesis inhibitor takes place in specific parts, e.g. cell types, tissue types and/or organs of the host, whereas in other parts of the host substantially no expression takes place. Spatial control can particularly be achieved by a cell- or tissue-type specific expression control sequence, e.g. promotor. Preferably, at least one of the expression control sequences contained in an expression system according to the invention is cell-type specific. Most preferably, the third expression control sequence is a cell-type specific expression control sequence, e.g. promoter. Alternatively or additionally, the first and/or second expression control sequence may be cell-type specific. The term "temporal control" means that expression of the protein synthesis inhibitor in the host takes place during a certain, e.g. predetermined time interval, whereas outside this time interval substantially no expression takes place. Temporal control can particularly be achieved by an expression control sequence inducible with a chemical substance that is applied externally. Preferably, at least one of the expression control sequences contained in an expression system according to the invention is inducible. For example, the first and/or second expression control sequence may be inducible. Preferably, both types of expression control, spatial and temporal, are combined.

Spatial and temporal specificity can be provided, for example, by means of a first expression control sequence (e.g. promoter) which is cell-type specific in combination with a second expression control sequence (e.g. promoter) which is inducible.

According to a preferred embodiment, spatial and temporal specificity is provided by means of first and second expression control sequences (e.g. promotors) which are inducible, for example by external stimuli (e.g. doxycycline) and the product of a third cell-type specific expression element (i.e. a third nucleic acid sequence encoding a regulator, e.g. an activator protein). The third expression element consists of a cell-type specific expression control sequence (e.g. promoter) driving the production of the activator protein.

The separation of the protein synthesis inhibitor into several individually inactive components and the subdivision of the expression system by using separate expression control sequences, each of which can be cell type-specific and preferably inducible, minimizes the probability of an undesired activity of the protein synthesis inhibitor occurring. Especially when using inducible expression control sequences, the split approach counters the intrinsic leakiness common to inducible expression systems.

A functional protein synthesis inhibitor can only be formed if the first and second nucleic acid sequences and, if present, the third nucleic acid sequence are actually expressed. This can be precisely regulated by spatial and temporal control of the different expression control sequences involved.

In certain embodiments, a host is selected which comprises at least two different types of cells or tissues, thereby allowing a spatial expression control of the protein synthesis inhibitor.

In certain embodiments, the first expression control sequence and/or the second expression control sequence are inducible expression control sequences. The term "inducible expression control sequence" particularly means an expression control sequence, which can be induced or activated by external stimuli. For example, this term includes expression control sequences which are inducible by a temperature shift, e.g. increase of temperature, by light, e.g. by radiating the host with light of a specific wavelength, by addition or removal of one or more chemical substances, e.g. of synthetic or biological origin, or by any combination thereof. Inducible expression control sequences are well known in the art. For example, the inducible expression control sequences may be chosen from tetracycline-controlled expression control sequences, hormone-controlled expression control sequences, e.g. an estrogen-receptor fusion system[21], light-controlled expression control sequences, and/or heat-shock expression control sequences[22]. A specific embodiment is the commercially available tetracycline-controlled expression system TetOn3G or any variant thereof, e.g. a light-controlled system such as PA-TetOn[23].

In certain embodiments, the expression system comprises a further genetic element, i.e. a third nucleic acid sequence encoding a regulator, e.g. an activator, for the first and/or second expression control sequence in operative linkage with a third expression control sequence. In these embodiments, the third expression control sequence may be a cell- and/or tissue-type specific expression control sequence, e.g. an expression control sequence specific for cells from brain, or for cells from organs or glands such as heart, liver, lung, kidney, stomach, duodenum, colon, pancreas, thyroid, ovary, or cervix or an expression control sequence specific for cells forming pre-cancerous or cancerous tissue.

In still further embodiments, the expression system is inducible by a site-specific recombinase, e.g. a Cre recombinase, and comprises recognition sites for said recombinase providing an induction of gene expression for the first, second and/or third nucleic acid sequence in the presence of a suitable recombinase. For example, the expression system may be provided with FLEX-switches[24] to make it compatible with a Cre recombinase containing host.

In certain embodiments, the expression system provides a reversible inhibition of protein synthesis in the host, i.e. the expression system may be controlled in a way that expression of the first and the second nucleic acid sequence encoding the first and the second component of the protein synthesis inhibitor, respectively, may be turned on and off again when providing appropriate external stimuli to the first and/or second expression control sequence. External stimuli can include a chemical substance (e.g. doxycycline) that is applied externally to provide temporal control. In certain embodiments, the expression in the host is turned off and then turned on for a predetermined period of time, e.g. about at least about 1 h to about 1 week, e.g. about 2 h to about 48 h, depending from the effect which should be achieved. In certain embodiments, the inhibition of protein synthesis occurs under conditions providing a subsequent recovery of protein synthesis in the host, i.e. after turning off the expression system the host can recover and resume protein synthesis.

In a particularly preferred embodiment, the expression system is regulated by two components: a further genetic element encoding a regulator for the first and/or second expression control sequence under control of a cell- and/or tissue-type specific expression control sequence (to provide spatial control) and a chemical substance (e.g. doxycycline) that is applied externally (to provide temporal control). The combination of a split-inhibitor with this particular inducible setup has the following advantages:

i) The cell-type specific expression control sequence, e.g. promoter, (spatial control) is only required to be specific for the targeted cell-type. Strong expression or inducibility are not required.

ii) The system allows for a strong inducibility and expression of the inhibitor, regardless of the targeted cell-type.

iii) A basal activity of the inducible promoter in the non-induced state can lead to unwanted intoxication, which can become problematic for highly effective/ toxic proteins (e.g. RIPs). The separate expression of the RIP chains ($\alpha$- & $\beta$-chains) in the present system solves this issue. Leakage will now produce an inactive part of the RIP ($\alpha$- or $\beta$-chain), that needs to find a suitable (also leaked) counterpart. This ensures a tightly regulated expression, where the protein synthesis in the target cell-population is completely unaffected until the external stimulus (e.g. doxycycline) is added.

Still a further aspect of the present invention relates to a method of inhibiting protein synthesis in a host, wherein the expression system as described above is introduced into the host, e.g. by transfection, transformation or transduction and the functional protein synthesis inhibitor encoded by the expression system, i.e. the non-covalent polypeptide complex comprising the first component and the second component as described above is expressed, whereby protein synthesis is inhibited in the host or in a part thereof. As indicated above, expression of the functional protein synthesis inhibitor is particularly under spatial and/or temporal control, or particularly under spatial and temporal control. Further, expression of the functional protein synthesis inhibitor may be a cell- and/or tissue-specific expression, i.e. expression of the functional protein synthesis inhibitor takes place only in a part, i.e. specific cells and/or tissues of the host. In certain embodiments, expression of the functional protein synthesis inhibitor is under conditions providing a recovery of protein synthesis after turning off expression of the protein synthesis inhibitor.

The expression system and the host of the present invention can be used in several fields, e.g. in medicine, basic research, medicine or in drug screening.

The expression system of the invention is useful for applications in basic research allowing cell- and/or tissue-type-specific inhibition of protein synthesis and providing targeted insight into function control and maintenance in complex tissues, organelles, or cell organoid cultures. This can be readily achieved with the expression system of the present invention, but is impossible with known chemical inhibitors (e.g. anisomycin, cycloheximide). They are potent and work fast, but are unspecific to the cell-types they inhibit and also have off-target effects[25]. This poses limitations for their use in tissue/organelles that comprise many different cell-types. For example, new cellular subtypes have been identified in brain regions[26-28] and other regions of the body[29], highlighting the heterogeneity of the cellular network. Inhibiting protein synthesis in one specific cell-type, leaving the remaining network intact allows targeted insight into the necessity of proteome remodeling in a particular cell type. This can be readily achieved with the use of the invention, but is impossible with universal chemical inhibitors that cannot be spatially controlled.

The expression system of the invention is also useful for applications in medicine. A hallmark of cancer cells is a dysregulation of the transcriptional machinery evoked by an overexpression of transcription factors and their constitutive activity[30]. This characteristic can be exploited to specifically target the protein synthesis inhibitor of the invention to cancer cells by making its expression dependent on these cancer-specific and/or cancer-enriched genes[31] and/or transcription factors (e.g. promoters for survivin[32], probasin[33, 34], or hTERT[35]). The inhibitor can then be used to either 'kill' these cells via a prolonged protein synthesis blockade and/or weaken their metastatic activity and work in synergy with available drug treatments. A key to the success of these genetic methods is the precise targeting of the therapeutic gene to cancer cells with no/minor impact on the surrounding healthy tissue. Due to its small size and broad compatibility with genetic targeting tools, the expression system of the invention provides great potential in this regard. The delivery mechanism (e.g. virus) can be tailored to the specific cancer/tissue type and advanced controlled induction systems, e.g. light-controlled induction systems, can further increase specificity not only to the targeted cancer cells but to the region where the inhibitor is synthesized. This is in particular interesting for the treatment of cancer types where cancer cells can be irradiated, e.g. skin cancer. Another way to restrict expression of the inhibitor to cancerous cells, which can be applied in synergy with the above mentioned methods, is the use of specific codons in the sequence that are favored by cancer cells[36].

In addition, a common drug-design principle is to distinguish normal and cancer cells via the presence of cancer specific proteins (e.g. receptors) on the cell surface. Using an inhibitor-mediated approach works, in contrast, from inside the cell as the specificity of the system is conferred by the specific expression profile of the cancer cells. This makes this tool more flexible/dynamic (resistant to mutations) compared to systems that only probe the surface, by detecting extracellular cues.

Further fields of application are neurological disorders, e.g. Fragile X syndrome (FXS) which is a prominent inherited form of intellectual disability (ID) and autism spectrum disorder (ASD), and has a strong behavioral impact on patients[37]. Due to its frequency and severity there is a great need for therapeutic approaches to help alleviate the accompanying symptoms. The FXS itself is caused by a mutation in the FMR1 gene. The trinucleotide CGG is repeated >200 times within the 5'UTR (untranslated region) of the gene, silencing its expression[38]. As a result the gene product fragile X mental retardation 1 protein (FMRP) is not produced anymore. FMRP is an mRNA binding protein and plays a key role in gene expression regulating (usually repressing) the translation of many mRNAs involved in the development and maintenance of synaptic structures[38]. As a regulator FMRP has been shown to repress the translation of synaptic mRNAs (e.g. Shank1, Arc or PSD-95)[40-42], but its absence also leads to a general increase in translation[43]. Without FMRP present an uncontrolled over-production of proteins brings along an imbalance that needs to be countered by therapeutic means.

There are different therapeutic strategies aiming at targets that are upstream of translational regulation[44-45], but also efforts using chemical protein synthesis inhibitors to shift translation back into the physiological range[46]. Here the expression system of the invention poses a promising alternative/basis for the development of a genetic therapy. The chemical inhibitors lack cell-type specificity and as such our genetic approach would potentially allow for a more specific targeting to affected cells (e.g. neurons) with less side effects. The present invention provides another advantage as the protein-sequence can be modified to modulate the toxicity to dial in the level of inhibition that is needed to return to a normal translational homeostasis. In addition to FXS there is also emerging data about other ASDs that involve dysregulated, increased translation[47,48].

Finally, the present invention provides a kit for providing expression of a genetically encoded protein synthesis inhibitor in a suitable host.

In the following, the invention is explained in more detail by the figures and examples as described below.

FIGURE LEGENDS

FIG. 1. Design and function of a genetically encoded protein inhibitor (gePSI)

a-c, The working principle. a, the gePSI renders ribosomes inoperative by depurinating adenine-4324 on the sarcin/ricin loop of the 28s rRNA. b, The inducible expression control system TetOn enables the temporal and cell type-specific expression of gePSI upon doxycycline (dox) administration. In the presence of dox the cell type-specific expression of the gePSI is enabled, shutting off protein synthesis. c, Schematic depiction of the transfected plasmids: (i) ProRIP and (ii) the gePSI (see also FIG. 2a). Addition of dox together with expression of the Tet-On 3G protein leads to expression of either construct.

d-e, Representative fluorescence images of hippocampal neurons transfected with the ProRIP (d) or the gePSI (e). Nascent protein signal is shown in red, anti-MAP2 immunostaining to visualize neuronal morphology is shown in blue. GFP (green) or dashed white outlines indicate transfected neurons. The following plasmids were co-transfected in these experiments: pCMV-Tet3G+pTRE3G-ProRIP+pCMV-AcGFP or pCMV-Tet3G+pTRE3G-Bi-gePSI-pCMV-AcGFP. Scale bar=20 μm.

f-g, Analysis of (d-e). Each dot represents the nascent protein signal intensity from one neuron normalized to the mean nascent protein signal of neighboring, untransfected neurons. From left to right: n=239, 46, 65; mean=1, 0.34, 0.19; sd=0.31, 0.29, 0.06; ** p<0.0001; Kruskal-Wallis test followed by Dunn's multiple comparison test (f). From left to right: n=369, 82, 86; mean=1, 1.1, 0.21; sd=0.34, 0.39, 0.1; ** p<0.0001; Kruskal-Wallis test followed by Dunn's multiple comparison test (g).

FIG. 2. gePSI expression element controls a, Scheme of plasmids used in this study. A plasmid carrying the Tet3G transactivator was co-transfected with plasmids driving the expression of the synthetic ProRIP (1), the gePSI (2) or the separate gePSI chains (3-4) under the control of an inducible pTRE3G or pTRE3G-Bi promoter.

b-c, Representative fluorescent images show hippocampal neurons co-transfected with pCMV-Tet3G+pCMV-AcGFP+pTRE3G-Bi-α-Chain (b) or pTRE3G-Bi-β-Chain (c). Nascent protein signal in red, anti-MAP2 immunostaining in blue and GFP in green (white outlines). Scale bar=20 μm.

d-e, Quantification of gePSI—alpha-Chain (b) and—beta-Chain (c) with (4 h) and without induction of their expression via dox. Each dot represents the nascent protein signal intensity from one neuron normalized to the mean nascent protein signal of neighboring, untransfected neurons. From left to right: n=66, 93; mean=1.11, 0.96; sd=0.37, 0.48; ns p>0.05; Mann-Whitney U test (d). From left to right: n=95, 84; mean=1.13, 0.98; sd=0.38, 0.46; ns p>0.05; Mann-Whitney U test (e).

FIG. 3. Detection of gePSI action using FUNCAT and comparison with pharmacological protein synthesis inhibition a, Representative fluorescent images of neurons 4 h after induction (4 h dox) or mock-induction (no dox) of gePSI expression in culture. The translational state of cells was assessed by an alternative metabolic labeling approach using fluorescent non-canonical amino acid tagging (FUNCAT) with the methionine analogue L-azido homoalanine (AHA/4 mM for 1.5 h). AHA incorporation was visualized via ClickChemistry (AHA, red), neuron shape is represented with MAP2 (blue) and gePSI-construct bearing neurons additionally express GFP constitutively (green/white outlines). Scale bar=20 μm. b, Quantification of (a). Each dot represents the nascent protein signal intensity from one neuron normalized to the mean nascent protein signal of neighboring, untransfected neurons. From left to right: n=39, 44; mean=1, 0.15; sd=0.39, 0.07; p ****<0.0001; Mann-Whitney U test.

c-d, Comparison of gePSI induction effect to anisomycin treatment. c, Representative fluorescent images of hippocampal neurons 4 h after induction (4 h dox), mock-induction (no dox) or 1 h anisomycin treatment. Nascent protein (Puro) in red, anti-MAP2 immunostaining in blue and GFP in green to indicate transfected neurons (white outlines). Scale bar=20 μm. d, Quantification of (c). Each dot represents the nascent protein signal intensity from one neuron normalized to the mean intensity of the dox minus control. From left to right: n=23, 32, 31; mean=1, 0.14, 0.11; sd=0.28, 0.05, 0.03; p ****<0.0001, ns p>0.05; Kruskal-Wallis test followed by Dunn's multiple comparison test. The following plasmids were co-transfected in these experiments: pCMV-Tet3G+pTRE3G-Bi-gePSI-pCMV-AcGFP.

FIG. 4. gePSI expressing cells do not exhibit compromised cell health relative to control cells a, Representative images of hippocampal neuron cultures treated without (0 h) or with 10 mM $H_2O_2$ for 1 h or 24 h. Cell death was visualized using the propidium iodide (PI) exclusion assay (red) and nucleoli were stained with the Hoechst dye (blue). Scale bar=20 μm.

b, Quantification of (a). Each dot represents the PI signal from one neuron normalized to the mean PI intensity of untreated neurons. From left to right: n=83, 107, 96; mean=1, 29.80, 67.32; sd=6.81, 35.43, 19.83; **** p<0.0001; Kruskal-Wallis test followed by Dunn's multiple comparison test.

c, Scheme (top) and representative images (bottom) of gePSI- or GFP- (ctrl) transfected primary hippocampal neurons (white outlines) that were continuously induced with 100 ng/ml dox for 1,2,4 or 6 d (dox was refreshed after 3 d). PI signal in red and Hoechst stain in blue. The following plasmids were co-transfected in these experiments: pCMV-Tet3G+pTRE3G-Bi-gePSI-pCMV-AcGFP or pCMV-AcGFP. Scale bar=20 μm.

d, Analysis of (c). Each dot represents the PI signal intensity from one transfected neuron normalized to the mean intensity of the dox minus control. From left to right: n=46, 38, 36, 39, 32, 46; mean=1, 1.58, 1.03, 2.32, 5.03, 1.22; sd=0.56, 1.64, 0.43, 4.23, 12.54, 0.63; ** p<0.01, ns p>0.05; Kruskal-Wallis test followed by Dunn's multiple comparison test.

FIG. 5. Temporally—resolved protein synthesis inhibition a-b, On-kinetics of gePSI in neurons. a, Schematic (top) and analysis (bottom) of nascent protein signal after 0, 0.5, 1, 2 and 4 h of dox incubation; protein synthesis was measured for the last 10 min of each dox incubation period. Each dot represents the nascent protein signal intensity from one neuron normalized to the mean nascent protein signal of neighboring, untransfected neurons. From left to right: n=19, 20, 18, 20, 19; mean=1.03, 0.97, 0.9, 0.2, 0.18; sd=0.27, 0.27, 0.39, 0.17, 0.04; ** p<0.0001; Kruskal-Wallis test followed by Dunn's multiple comparison test. In these experiments and those shown below (b-d), the following plasmids were cotransfected: pCMV-Tet3G+pTRE3G-Bi-gePSI-pCMV-AcGFP. b, Schematic (top) and analysis (bottom) of nascent protein signal after 0, 0.5, 1 and 2 h of dox incubation, followed by a chase without dox up to 4 h. Each dot represents the nascent protein signal intensity from one neuron normalized to the mean nascent protein signal of neighboring, untransfected neurons. From left to right: n=59, 50, 41, 45; mean=1.1, 0.34, 0.3, 0.23; sd=0.3, 0.28, 0.25, 0.15; ** p<0.0001; Kruskal-Wallis test followed by Dunn's multiple comparison test.

c-d, Reversibility of gePSI-mediated protein synthesis inhibition. c, Schematic (top) and representative images of hippocampal neurons transfected with gePSI (bottom). Nascent protein signal is shown in red. GFP (green) or dashed white outlines indicate transfected neurons. Images represent the time points indicated in the schematic. Scale bar=20 μm. d, Analysis of (c). Each dot represents the nascent protein signal intensity from one neuron normalized to the mean nascent protein signal of neighboring, untransfected neurons. From left to right: n=115, 121, 115, 115, 100; mean=1.1, 0.26, 0.57, 0.86, 1; sd=0.32, 0.23, 0.48, 0.54, 0.43; ns p>0.05,  p<0.01, * p<0.001, **** p<0.0001; Kruskal-Wallis test followed by Dunn's multiple comparison test.

FIG. 6. Extended or enhanced gePSI expression in neurons that exhibit retarded protein synthesis recovery a, Quantification of nascent protein signal after induction of gePSI transfected hippocampal neurons for 4 h using dox concentrations ranging from 1 to 1000 ng/ml. Each dot represents the nascent protein signal intensity from one neuron normalized to the mean nascent protein signal of neighboring, untransfected neurons. In these experiments and those shown below (b-e), the following plasmids were co-transfected: pCMV-Tet3G+pTRE3G-Bi-gePSI-pCMV-AcGFP. From left to right: n=32, 35, 38, 47, 34; mean=1.11, 1, 0.27, 0.23, 0.2; sd=0.3, 0.4, 0.2, 0.11, 0.06; p ****<0.0001, ns p>0.05; Kruskal-Wallis test followed by Dunn's multiple comparison test. The following plasmids were co-transfected: pCMV-Tet3G+pTRE3G-Bi-gePSI-pCMV-AcGFP.

b, Representative images of hippocampal neurons transfected with gePSI prior to the addition of dox (no dox) or after a 4 h incubation with dox (4 h dox), as well as examples of neurons that exhibited recovered protein synthesis levels (recovery-yes) or not (recovery-no) 24 h after the dox washout. Nascent protein signal is shown in red, anti-MAP2 immunostaining to visualize neuronal morphology is shown in blue and gePSI mRNA in white. Dashed white outlines indicate transfected neurons. Scale bar=20 μm.

c, Quantification of (b). Each dot represents the mRNA signal from one neuron normalized to the mean mRNA signal of all neurons in the no dox control. From left to right: n=40, 34, 48, 26; mean=1, 11.3, 3.4, 0.95; sd=0.38, 4.56. 1.55, 0.54; ** p<0.0001, * p<0.001, ns p>0.05; Kruskal-Wallis test followed by Dunn's multiple comparison test.

d, Representative images showing TUNEL staining in neurons before the induction of gePSI, 4 h post induction (4 h dox), 24 h (4 h dox+24 h chase) and 48 h (4 h dox+48 h chase) after dox washout and positive control. Arrowhead highlights background signal caused by lipofectamine transfection. Scale bar=5 μm.

e, Analysis of (d). TUNEL intensities were normalized to the mean TUNEL intensity of the positive control. From left to right: n=60, 67, 58, 49, 92; mean=0.4, 0.32, 0.27, 0.31, 1; sd=0.12, 0.12, 0.16, 0.13, 0.59; **** p<0.0001; Kruskal-Wallis test followed by Dunn's multiple comparison test.

FIG. 7. Cell type-specific protein synthesis inhibition a-f, Cell type-specific expression of gePSI in hippocampal cell cultures (containing both neurons and glial cells) or HeLa cells. Specificity was achieved using a Camk2a (a) or a GFAP (b) promoter to restrict transactivator expression in excitatory hippocampal neurons or astrocytes, respectively. The universal mammalian cytomegalovirus (CMV) promoter was used in HeLa cultures (e). Nascent protein signal in red and GFP in green. White outlines indicate transfected cells. The correct cell type for the heterogonous neuronal cultures is verified via FISH (cyan). HeLa cultures were homogenous and representative transfected HeLa cells are visualized with outlines (white dotted line) in the nascent-protein-channel. Scale bars=20 μm. c, d, f, The nascent protein signal in transfected cells was normalized to the respective signal from neighboring, untransfected cells. Each dot represents the mean intensity from one cell. HeLa cells treated with dox are shown relative to the dox minus control. From left to right: n=21, 20; mean=1.01, 0.14; sd=0.26, 0.07; ** p<0.0001; Mann-Whitney U test (c). n=35, 38; mean=0.89, 0.37; sd=0.37, 0.36;  p<0.0001; Mann-Whitney U test (d). From left to right: n=288, 270; mean=0.84, 0.47; sd=0.55, 0.36; ** p<0.0001; Mann-Whitney U test (f). The following plasmids were co-transfected: pCamk2a-Tet3G or pGFAP-Tet3G or pCMV-Tet3G+ pTRE3G-Bi-gePSI-pCamk2a-AcGFP or pTRE3G-Bi-gePSI-pGFAP-AcGFP or pTRE3G-Bi-gePSI-pCMV-AcGFP.

FIG. 8. Cre-dependent expression of the gePSI a, Scheme of the Cre-dependent gePSI-plasmid using the Cre recombinase for the cell type-specific expression of the gePSI.

b, Representative fluorescence images of hippocampal neurons transfected with the floxed Tet3G, and the gePSI with or without Cre recombinase. Nascent protein signal in red, anti-HA immunostaining in "fire" look-up to visualize Cre expression and GFP in green (white outlines) to indicate transfected neurons. Scale bar=20 μm.

c, Quantification of (b). Each dot represents the nascent protein signal intensity from one neuron normalized to the mean nascent protein signal of neighboring, untransfected neurons. From left to right: n=57, 77, 65; mean=1.13, 1.04, 0.29; sd=0.32, 0.32, 0.23; **** p<0.0001; Kruskal-Wallis test followed by Dunn's multiple comparison test.

d, Representative fluorescence images of hippocampal neurons transfected with the floxed Tet3G, gePSI and Cre recombinase under the Camk2a promoter. Nascent protein signal in red, FISH against Camk2a mRNA in cyan and GFP in green. Scale bar=20 μm.

e, Quantification of (d). Each dot represents the nascent protein signal intensity from one neuron normalized to the mean nascent protein signal of neighboring, untransfected neurons. From left to right: n=65, 42, 31; mean=1.1, 0.15; sd=0.3, 0.04; p ****<0.0001; two-tailed, unpaired t-test. The following plasmids were cotransfected: pCAG-Cre-IRES2-eGFP+pCMV-FLEX (inverted)-Tet3g-3xHA-FLEX (inverted)+pTRE3G-Bi-gePSI; pCamk2a-Cre+pCMV-FLEX (inverted)-Tet3g-3xHA-FLEX (inverted)+pTRE3G-Bi-gePSI+pCamk2a-AcGFP.

FIG. 9. gePSI induction does not perturb neuronal responses but prevents spine structural plasticity.

a, Representative images of stimulated neurons without (no dox) and with (4 h dox) gePSI induction. Nascent protein signal in red, anti-MAP2 in blue and GCaMP6 in green. The arrowheads indicate the 2p glutamate uncaging spots. The following plasmids were co-transfected in these experiments: pCMV-Tet3G+pTRE3G-BigePSI+pCMV-GCaMP6s (a-c). Scale bar=20 μm.

b, Magnification of the uncaging spots in (a). Images show calcium signal 100 ms before, during (stim), and 100/500 ms after 2P glutamate uncaging. Scale bar=2 μm.

c, Analysis of calcium signal after gePSI induction (4 h dox, red) and without gePSI induction (no dox, blue). Plotted is the mean change in calcium signal to 30× 2P uncaging events (delivered at 1 Hz) compared to the baseline calcium signal before stimulation. For analysis, the 5 frames following each uncaging event were averaged and the mean of the 30 events were compared between treatments. n=10, 12; ns p>0.05; Mann-Whitney U test.

d, Schematic (top) of experiment and group analysis (bottom) of spine-head volumes after local glutamate uncaging. gePSI expression without dox induction (blue, solid line, n=21 spines from 6 cells), dox administration with the isolated expression of Tet3G (blue, dashed line, n=14 spines from 4 cells) or gePSI induction (red, solid line, n=15 spines from 4 cells). Depicted are means±SEM. gePSI w/dox compared to gePSI w/o dox: p<0.0005; gePSI w/o dox compared to Tet3G w/dox: p=0.5; One way ANOVA, Tukey test for mean comparisons. The following plasmids were co-transfected in these experiments: pCMV-Tet3G+ pTRE3G-Bi-gePSI+pCMVGCaMP6s+pCMV-PSD-95-mCherry (d-e). e, Representative images of stimulated spines (dashed white outline) with (4 h dox) and without (no dox) gePSI induction; directly before (0 min) and 25/55 min after spine stimulation. The dot indicates the 2p glutamate uncaging spot. Scale bar=2 μm.

FIG. 10. Schematic depiction of plasmid pTRE3G-Bi-gePSI-pCMV-AcGFP.

The α-chain and the β-chain of maize RIP are encoded by separate nucleic acid molecules in operative linkage with the tetracycline-inducible bi-directional TREG3 BI promoter. The vector backbone is derived from pAAV-cDNA6-V5His (Vector Biolabs).

Figure 11:
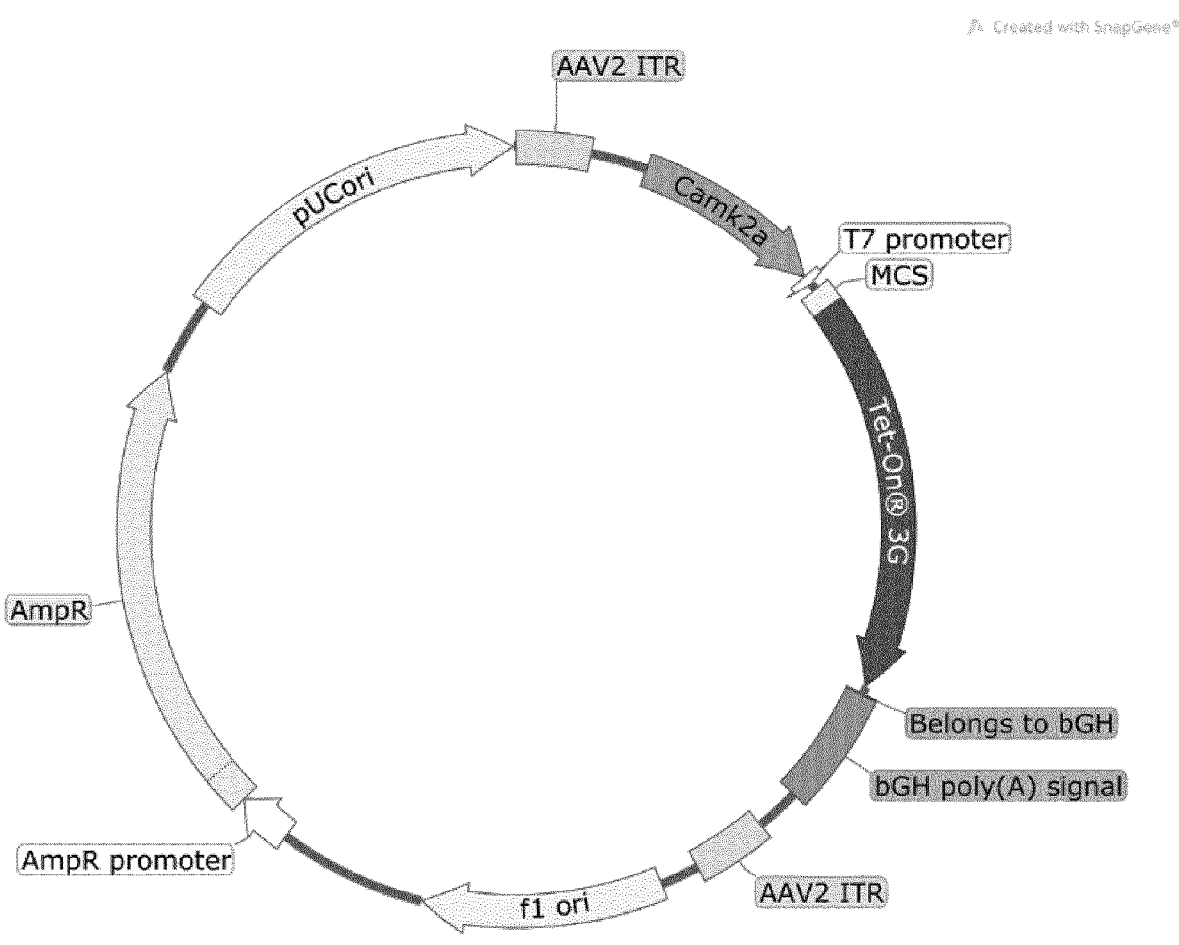

FIG. 11. Schematic depiction of plasmid pCamK2a-TetOn3G.

The nucleic acid sequence encoding the transactivator TetOn3G is in operative linkage with the tissue-specific CamKa2 promoter. The vector backbone is derived from pAAV-cDNA6-V5His (Vector Biolabs).

Figure 12:
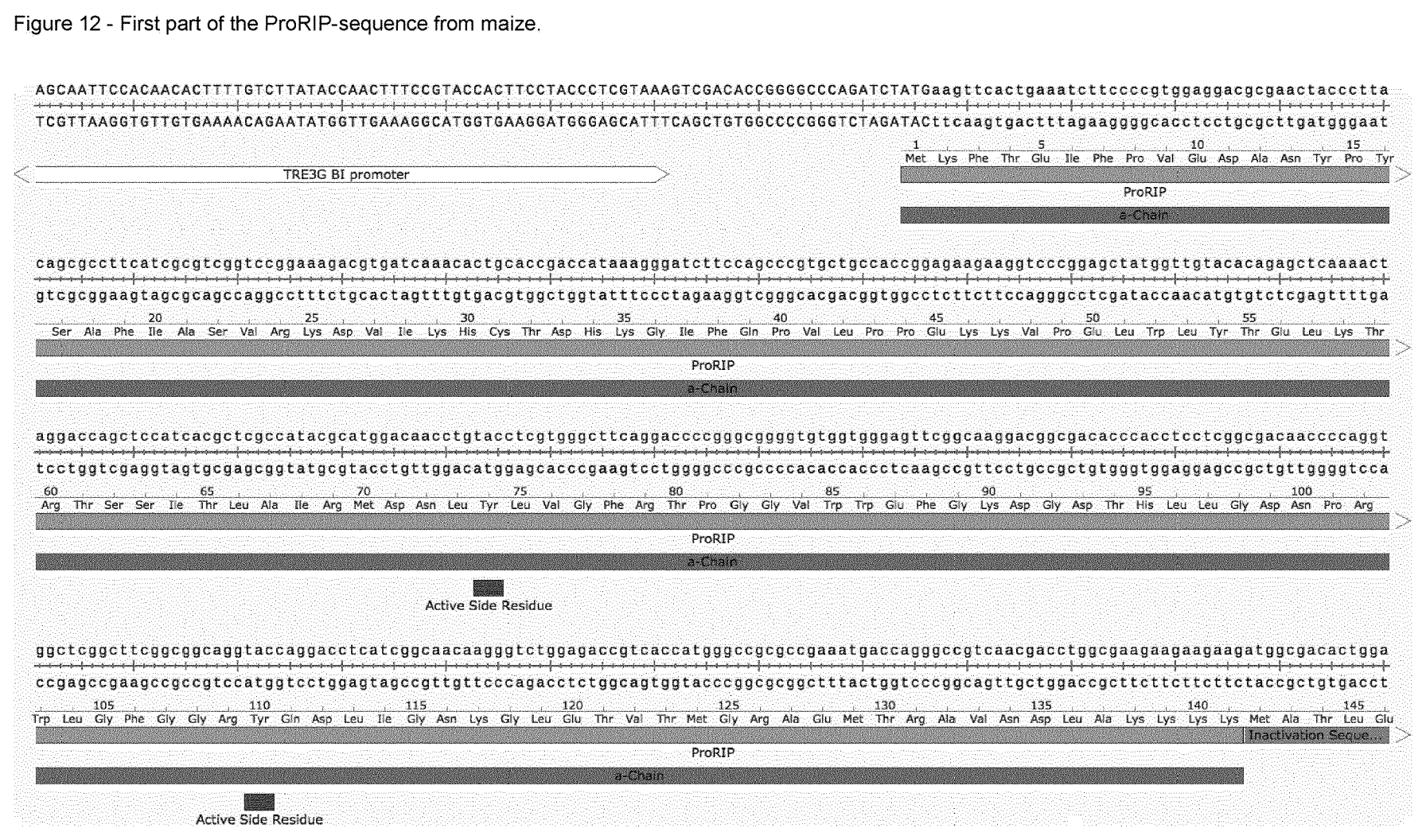

FIG. 12. First part of the sequence of ProRIP from maize.

Nucleic acid sequence and amino acid sequence (triple letter code; SEQ ID NO: 3, amino acids 1-146) are shown. ProRIP is indicated in blue/light blue, the α-chain is indicated in light green, active site residues are indicated in dark green.

Figure 13:
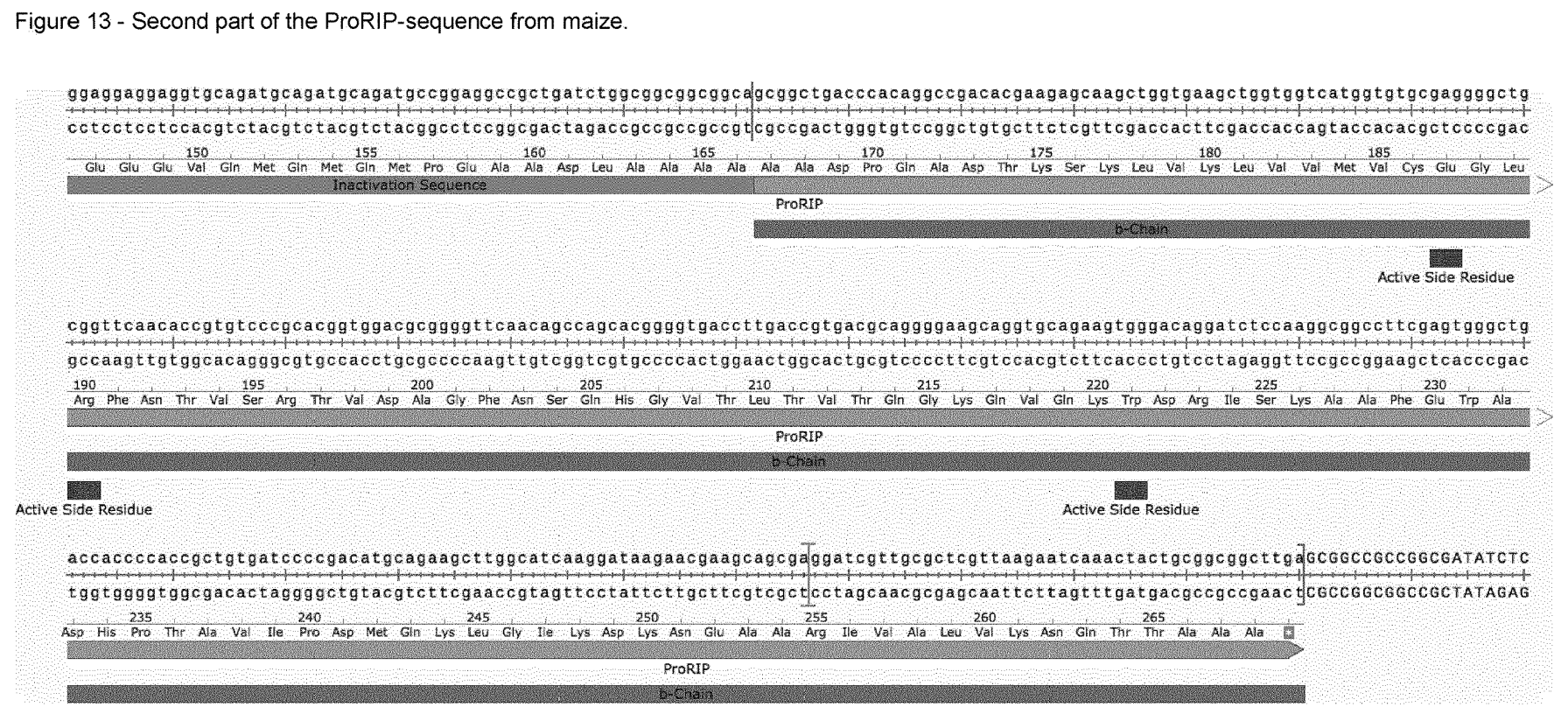

FIG. 13. Second part of the sequence of ProRIP from maize.

Nucleic acid sequence and amino acid sequence (triple letter code; SEQ ID NO: 3, amino acids 147-268) are shown. ProRIP is indicated in blue/light blue, the β-chain is indicated in light green, active site residues are indicated in dark green.

FIG. 14. Amino acid sequence alignment.

Amino acid sequence alignment (single letter code) between MOD (gj 25422082; SEQ ID NO: 4) and RIP superfamily member (Cdd:pfam00161; SEQ ID NO: 5). Blue indicates different sequence, red indicates same sequence, active site residues are shown by green rectangles.

FIG. 15. Amino acid sequence alignment.

Amino acid sequence alignment (single letter code) between MOD (Query; SEQ ID NOs: 9, 11 and 13, respectively) and different RIP family members (upper: ricin-like, SEQ ID NO: 10; middle: trichosanthin, SEQ ID NO: 12; lower: gelonin, SEQ ID NO: 14). Blue box indicates sequence similarity, red box indicates conserved active site residues.

EXAMPLE 1

Development of a Genetically Encoded Protein Synthesis Inhibitor (gePSI) Based on a Ribosome Inactivating Protein (RIP) from Maize Example 1 and FIGS. 1-9 are taken from a manuscript submitted and accepted by nature Methods for publication as a 'Brief Communication' in 2019. It is scheduled for pub-lication under the title 'A genetically encodable cell type specific protein synthesis inhibitor' by the authors 'Maxi-milian Heumüller, Caspar Glock, Vidhya Rangaraju, Anne Biever, and Erin M. Schuman'.

1. Results

We developed a fully genetically encoded protein synthe-sis inhibitor (gePSI) that allows one to control protein synthesis in a temporal and spatial manner.

To develop a gePSI we considered the class of bacterial and plant toxins from the Shiga and Ricin families that are known as "ribosome inactivating proteins" (RIPs)[2,3]; most RIPs effect a complete shutdown of protein synthesis by depurinating adenine-4324 on the sarcin/ricin-loop of the 28S rRNA4 (FIG. 1a).

Specifically, we used an atypical class-1 RIP from maize (Zea mays)[5,6]. The full-length maize RIP contains two catalytically active chains as well as inactivation regions, which are proteolytically eliminated during RIP activation to increase enzyme potency. In order to induce the expression of various gePSI candidates in hippocampal cultures we used the TetOn3G system in which doxycycline (dox) intro-duction enables expression (FIG. 1b, c and 2a).

We measured the efficacy of different candidate gePSIs by metabolic labeling of transfected cultured hippocampal neu-rons with a brief pulse of puromycin, followed by detection of nascent protein in situ[7]. The synthetic ProRIP molecule contains the active chains as well as a single internal inactivation region (FIG. 1c, (i)). The mere co-transfection of ProRIP (pCMV-Tet3G+pTRE3G-ProRIP+pCMVAcGFP) into neurons in the absence of dox induction resulted in complete shutdown of protein synthesis in a majority of the cells (FIG. 1d, f).

Thus, we physically separated the two chains (labelled "alpha and beta", FIG. 1c) of the ProRIP. We co-transfected neurons with a plasmid containing both chains driven by a bi-directional dox-inducible promoter as well as the activa-tor plasmid (FIG. 1c, (ii); FIG. 2a). Using this strategy, protein synthesis levels in transfected but uninduced neurons ("no dox") were indistinguishable from control, untrans-fected neurons (FIG. 1e, g). In contrast, a 4 h induction resulted in a dramatic and uniform reduction of protein synthesis in transfected, but not in neighboring untrans-fected, neurons (FIG. 1e, g).

The inhibition of protein synthesis required the combined expression of the alpha and beta chains, as expression of either chain alone did not inhibit protein synthesis (FIG. 2b-e). The gePSI-induced inhibition of protein synthesis was also detected with an alternative metabolic labeling approach that uses non-canonical amino acids[8,9] (FIG. 3a, b) and was indistinguishable from that observed following treatment with the chemical protein synthesis inhibitor ani-somycin (FIG. 3c, d). Moreover, expression of the gePSI did not promote cell death even when continuously expressed for 6 days (FIG. 4a-d), indicating that it can be used to perturb protein synthesis without obvious adverse effects on cellular health.

The time scales over which protein synthesis influences cellular and neuronal plasticity range from minutes to days[1, 10] To determine the temporal precision of the protein syn-thesis inhibition driven by the gePSI, we varied the duration of the expression induction by dox from 0.5 to 4 h (FIG. 5a). In the last 10 min of the dox induction we measured protein synthesis, as before. Inducing the expression of the gePSI for less than 1 h did not result in a consistent inhibition of protein synthesis in hippocampal neurons (FIG. 5a). Induc-ing for 2 or 4 h, however, resulted in a consistent and complete inhibition of neuronal protein synthesis (FIG. 5a). The observed requirement for at least 2 h of induction could represent the time needed to achieve adequate levels of the gePSI mRNA or the time needed for the gePSI protein to express. To distinguish between these possibilities, we induced with dox for variable durations but then delayed the measurement of protein synthesis to a uniform end point of 4 h following the initiation of induction (FIG. 5b). This experiment revealed that even a 30 min induction of the gePSI transcription was sufficient to significantly reduce protein synthesis measured 3.5 h later (FIG. 5b) although the inhibition of protein synthesis exhibited even greater reli-ability with longer induction periods (FIG. 5b).

In many in vitro and in vivo experiments, plasticity is induced by a brief external event that results in a defined period of protein synthesis that is required for the plasticity expression[11,12] To determine whether we could effect a temporally discrete period of protein synthesis inhibition that later exhibits recovery, we first optimized the dox concentration (FIG. 6a), induced the gePSI and then exam-ined protein synthesis in neurons at 4, 24, 48 and 72 h (FIG. 5c, d). As before, protein synthesis was inhibited following 4 h of gePSI induction (FIG. 5c, d). Probing 24 h later, however, revealed a significant recovery of protein synthesis levels in a large proportion of neurons, which increased over time to almost 90% recovery after 72 h. In order to address why some neurons did not recover we quantified gePSI expression using fluorescence in situ hybridization, reason-ing that enhanced persistence or levels of gePSI expression might lead to prolonged recovery times (FIG. 6b, c). Indeed, we found that neurons, which did not show recovery after 24 h exhibited higher gePSI mRNA levels when compared to fully recovered neurons. We noted that those neurons that exhibited retarded recovery within the time-course mea-sured, however, did not exhibit enhanced apoptosis when probed 24/48 h after a 4 h gePSI induction (FIG. 6d, e). These data indicate that the gePSI can transiently inhibit protein synthesis in cells for a defined period of time; these cells then exhibit functional recovery of their protein syn-thesis capabilities.

The ideal gePSI should exhibit spatial (e.g. tissue- and/or cell-type-specific) as well as temporal control. An exem-plary implementation of a cell type-specific gePSI involves the use of a cell type-specific promoter to drive gePSI expression (FIG. 1b), for example in Camk2a-positive (FIG. 7a, c), GFAP-positive (FIG. 7b, d) cells or other cell lines (FIG. 7e-f). To maximize flexibility, we combined the plat-form with a Cre-inducible system (FIG. 8a). To include temporal control, we floxed an HA (epitope)-tagged Tet3G (activator) element to enable Cre-induction, either via an external construct, or via introduction to a transgenic animal line. The Cre-dependent expression of Tet3G together with the addition of dox provides cell type-specificity and tem-poral control, respectively. We transfected neurons with the floxed Tet3G, the gePSI and a Cre recombinase plasmid. Only those cells that expressed Cre and were treated with dox exhibited significantly reduced protein synthesis (FIG. 8b, c). These data indicate that the gePSI can be used to bring about a temporally discrete episode of protein synthe-sis inhibition in an identified cell type (FIG. 8d, e).

Although some short-term forms of synaptic plasticity rely exclusively on covalent modifications of pre-existing proteins, many forms of plasticity, both synaptic and behav-ioral, require protein synthesis[1,13]. To test the function of the gePSI during plasticity we first examined the compatibility of gePSI expression with synaptic transmission. We expressed the $Ca^{2+}$-indicator GCaMP6s in cultured hippocampal neurons and determined their ability to respond to extracellular stimulation, using two-photon (2P) uncaging of caged glutamate (FIG. 9a-c). gePSI-expressing neurons were competent to respond to single stimuli of individual dendritic spines as well as trains of stimulation (FIG. 9a-c). Using 2P glutamate uncaging, we induced a form of plasticity that is known to require protein synthesis[12] (FIG. 9d). This plasticity results in an enlargement of the stimulated spine, which is associated with enhanced synaptic responsiveness. Single spine stimulation (0.5 Hz) in neurons transfected with the gePSI in the absence of dox exhibited a rapid and persistent (~ for up to 55 min) increase in spine-head volume (FIG. 9d, e). Similarly, neurons that expressed Tet3G but not the gePSI also exhibited the stimulation-induced plasticity. However, neurons that expressed the gePSI in the presence of dox exhibited only a small increase in spine-head volume immediately after stimulation that decayed back to baseline values within 10 min or so, indicating a requirement for protein synthesis in the stimulated neuron.

Here we have developed a genetically encoded protein synthesis inhibitor that can be induced to effectively, rapidly (e.g. within a few hours), and reversibly shutdown protein synthesis in targeted cells; neighboring cells are unaffected. By judicious use of both Cre-targeting and temporal induction, neurons that project to specific areas could be targeted for inhibition in vivo to probe the importance of different cell populations in learning and memory. In addition, the cell type-specific inhibition we achieve suggests that the gePSI can be used clinically to target identifiable cell populations, e.g. rapidly proliferating cells, to abbreviate cancer states.

2. Material and Methods

Cell Culture

Dissociated rat hippocampal neurons were prepared from P0-1 day-old rat pups as previously described[14]. Neurons were plated onto poly-d-lysine coated glass-bottom Petri dishes (MatTek) and cultured in neuronal growth medium (NGM, Neurobasal-A supplemented with B27 and Gluta-MAX). The cultures were maintained in a humidified incubator at 37° C. and 5% $CO_2$. HeLa cells were maintained in Dulbecco's modified Eagle's medium (DMEM, Invitrogen) supplemented with 10% FCS at 37° C. in a 5% $CO_2$ atmosphere. Once cells reached a confluency of 70% they were passaged. Only cells that were passaged less than 10 times were used for experiments.

Transient Transfection of Hippocampal Neurons or HeLa Cells

Primary hippocampal neurons were transfected at DIV 11 using CombiMag following the manufacturer's recommendations. Experiments were performed at least 12 h post-transfection to guarantee sufficient expression of the constructs. HeLa cells, at 50% confluency, were transfected with Lipofectamin 2000 according to the manufacturer's guidelines. The inducible expression system TetOn3G was purchased from Takara Bio—Clontech (#631337). Additional plasmids used in this study were gifted by P. C. Shaw, C. Hanus, S. Sternson[15] (Addgene #18925), J. M. Wilson (Addgene #105558) and A. Chenn[16] (Addgene #26646). Cloning was performed using Gibson Cloning.

Dual, triple or quadruple transfections were performed with the following plasmids:

pCMV-TetOn3G+pTRE3G-Bi-ProRIP/α-Chain/β-Chain+pCMV-AcGFP-N1 pCMV-TetOn3G+pTRE3G-BigePSI-pCMV-AcGFP+pCamK2a-TetOn3G+pTRE3G-Bi-gePSI-pCamK2a-AcGFP pGFAP-TetOn3G+pTRE3G-Bi-gePSI-pGFAP-AcGFP pCMV-FLEX (inverted)-TetOn3G-3xHA-FLEX (inverted)+pTRE3G-Bi-gePSI-pCMV-AcGFP+pCAG-Cre-IRES2-eGFP (Addgene #26646) pCMV-FLEX (inverted)-TetOn3G-3xHA-FLEX (inverted)+pTRE3G-Bi-gePSI+pCamK2a-Cre (Addgene #105558)+pCamKa2-AcGFP In each of the transfections, a 1:4 ratio between the activator plasmid (TetOn3G) and the responder plasmid (pTRE3G-Bi) was used. The β-chain of gePSI is C-terminally fused to a murine ornithine decarboxylase (ODC36) degron.

A schematic depiction of plasmid pTRE3G-Bi-gePSI-pCMV-AcGFP is shown in FIG. 10. A schematic depiction of plasmid pCamK2a-TetOn3G is shown in FIG. 11.

Doxycycline Hyclate (Dox) Treatment

Doxycycline hyclate (Sigma-Aldrich/Merck, D9891) was dissolved in $H_2O$ to yield a 1 mg/ml stock solution. Dox was added to the growth medium of transfected cells to a final working concentration of 1 µg/ml to induce gePSI expression (unless otherwise stated). For the protein synthesis recovery experiments 10 ng/ml was used, neurons were washed three times with NGM and replaced with their growth medium that had been saved prior to dox treatment.

Fluorescent Non-Canonical Amino Acid Tagging (FUN-CAT)

FUNCAT was performed as previously described[8,9] with the following modification: a biotin-alkyne (Acetylene-PEG4-Biotin, Jena Bioscience) was used as a tag in the copper-catalyzed [3+2] azide-alkyne cycloaddition (CuAAC) click reaction. Hippocampal neurons were incubated in methionine-free Neurobasal-A medium (custom-made by Life Technologies) supplemented with 4 mM AHA (prepared as described in[17]) for 1.5 h. Cells were washed two times with PBS-MC (1×PBS, pH 7.4, 1 mM $MgCl_2$, 0.1 mM $CaCl_2$) and fixed for 20 min in PFA-sucrose (4% paraformaldehyde, 4% sucrose in PBS-MC) at room temperature. Cells were washed with 1×PBS, permeabilized with 0.5% Triton X-100 in 1×PBS, pH 7.4, for 15 min and blocked with blocking buffer (4% goat serum in 1×PBS) for 1 h. Cells were equilibrated to optimal click conditions by washes with 1×PBS, pH 7.8. After the click reaction, cells were incubated with primary antibodies (anti-MAP2 (SySy, 188004, 1:1000), anti-biotin (Cell Signaling, 5597, 1:2000) in blocking buffer overnight at 4° C. Secondary antibodies were incubated in blocking buffer for 45 min at room temperature.

Immunocytochemistry and Puromycylation

Nascent proteins were labeled by incubating cells with puromycin (stock solution 50 mg/ml in $H_2O$; Sigma-Aldrich/Merck, P8833) at a final concentration of 3 µM for 10 min in full medium at 37° C. in a humidified atmosphere with 5% $CO_2$. Cells were then rinsed in 1×PBS and fixed for 20 min in PFA (4% paraformaldehyde in 1×PBS), permeabilized with 0.5% Triton X-100 in 1×PBS supplemented with 4% goat serum, for 15 min and blocked with blocking buffer (4% goat serum in 1×PBS) for 1 h. Primary antibodies (anti-MAP2 (SySy, 188004, 1:1000), anti-puromycin (Kerafast, EQ0001, 1:2000)) were incubated in blocking buffer overnight at 4° C. Secondary antibodies (ThermoFisher, A11030, 1:1000; Jackson I R, 106-475-003, DyLight 405, 1:500) were incubated in blocking buffer for 45 min at room temperature.

High-Resolution In Situ Hybridization

In situ hybridization was performed using the Quantigene ViewRNA ISH Cell Assay for Fluorescence with probes targeting the coding sequence of Camk2a (VC6-11639), GFAP (VC6-11478) or gePSI (α-Chain: VPWCWCK (type 6); β-Chain: VPXGPWH (type 1)). The manufacturer's protocol was applied with the following modifications: Cells were fixed for 20 min at room temperature using a 4% paraformaldehyde solution (4% paraformaldehyde, 5.4% glucose, 0.01 M sodium meta-periodate, in lysine-phosphate buffer). The Proteinase K treatment was omitted in order to preserve the integrity of the cells. After completing the in situ hybridization, cells were washed with 1×PBS and incubated in blocking buffer (4% goat serum in 1×PBS) for 1 hr. Nascent proteins and neuronal morphology was stained as described above.

Cell Health Assays

To assess cell health two assays were used:

The propidium iodide (PI) exclusion assay was performed by incubating cells in full medium with 1 μl/ml PI (stock solution 1 mg/ml in $H_2O$; invitrogen/Thermo Fisher Scientific, P1304MP) and 20 μM Hoechst 33342 (stock solution 20 mg/ml in $H_2O$; Sigma-Aldrich/Merck, B2261) for 10 min at 37° C. in a humidified atmosphere with 5% $CO_2$. Cells where then transferred microscope (pre-heated chamber at 37° C.) for live imaging. For the positive control, cells were treated with a final concentration of 10 mM $H_2O_2$ (stock solution 27% $H_2O_2$; Alfa Aesar, L13235) for 1 h or 24 h in full medium prior to PI/Hoechst staining.

The apoptosis assay 'Click-iT™ TUNEL Alexa Fluor™ 647 Imaging Assay' from ThermoFisher Scientific was used according to the manufacturer's protocol. For the positive control, cells were treated with DNAse I solution for 30 min after fixation as indicated in the protocol.

Imaging and Image Analysis

Fluorescence imaging was performed with a LSM780 or LSM880 laser scanning confocal microscope (Zeiss) with ×20 air objective (Plan Apochromat 20×/0.8 M27) or ×40 oil objective (Plan Apochromat 40×/1.4 oil DIC M27) with appropriate excitation laser lines and spectral detection windows. Images were acquired in 16-bit mode as z-stacks, covering the entire thickness of the cell, with 1024×1024- or 2048×2048-pixel image resolution. Laser power and detector gain were adjusted to ensure a good dynamic range, without saturating pixels. Imaging conditions were held constant within an experiment. For image analysis the raw images were split into single-channel images and maximum-intensity projections were created (Zeiss-Zen Black). To quantify the nascent protein signal for individual cells the cell body (soma for neurons) was manually traced to create a mask using the MAP2- and GFPchannel, the traced masks were then used in the 'metabolic labeling'-channel and the mean intensity within the mask was measured (NIH-ImageJ). In order to correct for technical deviations (e.g. small differences in puro incubation times), the puro-signal of transfected cells was normalized to the mean puro-signal of a maximum of 10 untransfected, neighboring cells.

All live imaging experiments were performed at a temperature of 37° C. in modified E4 imaging buffer containing (in mM) 120 NaCl, 3 KCl, 10 HEPES (buffered to pH 7.4), 4 $CaCl_2$ (lacking $MgCl_2$) and 10 Glucose. Live cell imaging was performed using an inverted spinning disk confocal microscope (3i imaging systems; model CSU-X1) using the Slidebook 5.5 software. For glutamate uncaging experiments, images were acquired with a Plan-Apochromat 63×/1.4 Oil DIC objective at laser powers 1.1 mW (488 nm) and 0.8 mW (561 nm) using an Evolve 512 camera (Photometrics). 488 nm excitation and 525/30 nm emission filters were used for GCaMP6s; 561 nm excitation and 617/73 nm emission filters were used for PSD95-mCherry fluorescence.

Images were analyzed using ImageJ, unless specified otherwise. OriginPro 2017 was used for data analysis, statistical testing and plotting graphs.

Uncaging and Spine-Head Volume Measurements

Neurons were transfected with GCaMP6s, PSD95-mCherry, pCMV Tet3G and pTRE3G-Bi-gePSI plasmid constructs. The absence of the pTRE3G-Bi-gePSI construct was used as control. Neurons were either treated with dox for 4 hours (for gePSI-induction) prior to the imaging, or untreated (control). Both gePSI-induced and untreated control neurons were identified by changes in GCaMP6s fluorescence corresponding to calcium transients in dendrites and spines. PSD95-mCherry fluorescence was used to identify spines for glutamate uncaging. Before glutamate uncaging, neuronal media was replaced with 1 μM TTX (Citrate salt, 2 mM stock made in water), 50 μM Forskolin (Tocris Bioscience, 100 mM stock made in DMSO), 2 mM 4-Methoxy-7-nitroindolinyl-caged-L-glutamate (MNI caged glutamate) (Tocris Bioscience, 100 mM stock made in E4 buffer) in modified E4 buffer. Glutamate uncaging was performed using a multiphoton-laser 720 nm (Chameleon, Coherent) and a Pockels cell (Conoptics) for controlling the uncaging pulses. Spines that were at least 50 μm away from the cell body were chosen for uncaging experiments. To test a spine's response to an uncaging pulse, an uncaging spot (~2 μm²) close to a spine head was selected and two to three uncaging pulses at 10 ms pulse duration per pixel and 2.5 mW power were given and the spine was checked for spine-specific calcium transients. For synaptic transmission experiments, an uncaging protocol of 30 uncaging pulses at 1 Hz with 10 ms pulse duration per pixel was used. For plasticity experiments, an uncaging protocol of 60 uncaging pulses at 0.5 Hz with 10 ms pulse duration per pixel, at 2.5 mW power was used. Images were acquired every 10 min for up to 55 min. For analysis of spine morphology, we used a custom-written Matlab script. Ten images from each time point were averaged and a line crossing the center of the spine-head was drawn. The fluorescence intensity measured along the line was fit to a Gaussian to obtain the full width at half maximum—defined as the spinehead diameter[18]. Spine-head diameter was converted to spine-head volume, under the assumption that the spine-head is spherical. The uncertainty of the spine-head diameter measurement was determined from standard error of the mean and was converted to the uncertainty of the spine-head volume by standard error propagation[19].

Sample Size Choice and Statistics

Sample size choice was determined as follows: within one replicate the maximum number of culture dishes was limited to 12 to ensure consistent experimental procedure for all dishes. The experimenter selected the transfected cells in the GFPchannel blind to the 'metabolic-labeling'-channel (not blind to the condition) and all or at least 20 transfected cells in a dish were imaged. Unless otherwise stated, all experiments were repeated with dishes originating from two independent cell preparations. Within one experiment at least 2 dishes were used per condition. The experiments in supplementary FIG. 2-4 were performed with multiple dishes originating from a single neuronal preparation (prepared from ~10 P0-1 rat pups). The "n" in the figure legends depict the number of cells imaged per condition. For quantification and testing of statistical significance, data are displayed as combined graphs from multiple experiments. For all data sets, the Pearson omnibus normality test was applied to test for normal distribution. If normality was proven, Student's, unpaired t-test (for two groups) was applied. For non-normally distributed data sets, the Mann- Whitney U test (for two groups) or Kruskal-Wallis test was applied (for three or more groups). An F-test was applied to compare variances before Student's t-test. For multiple-comparison analysis, Dunn's test of multiple comparisons was applied.

EXAMPLE 2

General Concept of gePSI Development Based on Active Conservation in Ribosome-Inactivating Proteins We examined the structure of the maize RIP used in Example 1 to evaluate the similarity to other members of the RIP family. In a structure-function study on maize RIP in 2007[6], certain similarities between the active sites of members of the RIP family were found. The active site residues are substantially conserved throughout the RIP family and spread over the entire sequence of the protein.

Thus, based on the results obtained in Example 1, it is likely to develop an expression system for other members of the RIP family, e.g. class 1 and class 2 RIPs by splitting the nucleic acid sequence encoding a monomeric RIP protein with N-glycosidase activity or a monomeric RIP subunit with N-glycosidase activity into two separate nucleic acid sequences such that some of the active site residues are encoded by each of the two separate nucleic acid sequences.

FIGS. 12 and 13 show the sequence of the maize RIP precursor ProRIP (blue & light blue) with α-/β-chain regions highlighted (light green). The amino acid sequence of the ProRIP is shown in SEQ ID NO: 3. The amino acids that make up the catalytically active site in the final toxin are highlighted in dark green (Tyr74, Tyr110, Glu187, Arg190 and Trp221; taken from Mak et al. (2007)[6]).

These active site residues are at least partially conserved throughout most or all RIPs and thus can be identified by amino acid sequence alignments although their positions within the individual family members may be slightly different.

We carried out a BLAST (Basic Local Alignment Search Tool) alignment of the amino acid sequence designated "MOD" shown in SEQ ID NO: 4 (that is an α-chain and β-chain of maize RIP depicted as single chain) to identify regions of local similarity between sequences. Doing so we can determine the sequence similarity between different RIP family members but we can also compare the maize RIP sequence against a 'superfamily' member (FIG. 14) that can be seen as a consensus sequence from many RIP proteins[20] shown in SEQ ID NO: 5. The sequence of MOD (both chains) shares ~40% identity with the averaged 'superfamily RIP'.

A further BLAST search of portions of the MOD sequence (SEQ ID NO: 9, 11 and 13) against portions of specific RIPs ricin-like (SEQ ID NO: 6/SEQ ID NO: 10), trichosanthin (SEQ ID NO: 7/SEQ ID NO: 12) or gelonin (SEQ ID NO: 8/SEQ ID NO: 14) provides lower overall similarities of ~25%, ~21% and ~24% (FIG. 15). The active site residues however are conserved and may be identified although their positions within the different proteins can vary.

Despite being variable in their amino acid sequences, all RIPs have N-glycosidase activity on a common target. They target the 28S rRNA on the large 60S ribosomal subunit and cleave off (depurinate) the adenine located on sarcin-ricin loop of that particular rRNA[2]. Without this functional loop, ribosomes cannot bind specific elongation factors anymore and thus are functionally inactive. By splitting a nucleic acid sequence encoding a RIP such that active site residues are present on each of the two parts, represents a general concept of an expression system for a gePSI (analogous to the expression system of Example 1).

REFERENCES

1. Sutton, M. A. & Schuman, E. M. Dendritic protein synthesis, synaptic plasticity, and memory. *Cell* 127, 49-58 (2006).
2. Walsh, M. J., Dodd, J. E. & Hautbergue, G. M. Ribosome-inactivating proteins: potent poisons and molecular tools. *Virulence* 4, 774-784 (2013).
3. Puri, M., Kaur, I., Perugini, M. A. & Gupta, R. C. Ribosome-inactivating proteins: current status and bio-medical applications. *Drug Discov. Today* 17, 774-783 (2012).
4. Endo, Y. & Tsurugi, K. The RNA N-glycosidase activity of ricin A-chain. *Nucleic Acids* Symp. Ser. 139-142 (1988).
5. Hey, T. D., Hartley, M. & Walsh, T. A. Maize ribosome-inactivating protein (b-32). Homologs in related species, effects on maize ribosomes, and modulation of activity by pro-peptide deletions. *Plant Physiol.* 107, 1323-1332 (1995).
6. Mak, A. N.-S. et al. Structure-function study of maize ribosome-inactivating protein: implications for the internal inactivation region and the sole glutamate in the active site. *Nucleic Acids Research* 35, 6259-6267 (2007).
7. Schmidt, E. K., Clavarino, G., Ceppi, M. & Pierre, P. SUnSET, a nonradioactive method to monitor protein synthesis. *Nat. Methods* 6, 275-277 (2009).
8. Dieterich, D. C. et al. In situ visualization and dynamics of newly synthesized proteins in rat hippocampal neurons. *Nat. Neurosci.* 13, 897-905 (2010).
9. Tom Dieck, S. et al. Metabolic labeling with noncanonical amino acids and visualization by chemoselective fluorescent tagging. *Curr Protoc Cell Biol* Chapter 7, Unit7.11 (2012).
10. Davis, H. P. & Squire, L. R. Protein synthesis and memory: a review. *Psychol Bull* 96, 518-559 (1984).
11. Ho, V. M., Lee, J.-A. & Martin, K. C. The cell biology of synaptic plasticity. *Science* 334, 623-628 (2011).
12. Govindarajan, A., Israely, I., Huang, S.-Y. & Tonegawa, S. The dendritic branch is the preferred integrative unit for protein synthesis-dependent LTP. *Neuron* 69, 132-146 (2011).
13. Cajigas, I. J., Will, T. & Schuman, E. M. Protein homeostasis and synaptic plasticity. *EMBO J.* 29, 2746-2752 (2010).
14. Aakalu, G., Smith, W. B., Nguyen, N., Jiang, C. & Schuman, E. M. Dynamic visualization of local protein synthesis in hippocampal neurons. *Neuron* 30, 489-502 (2001).
15. Atasoy, D., Aponte, Y., Su, H. H. & Sternson, S. M. A FLEX switch targets Channelrhodopsin-2 to multiple cell types for imaging and long-range circuit mapping. *J Neurosci* 28, 7025-7030 (2008).
16. Woodhead, G. J., Mutch, C. A., Olson, E. C. & Chenn, A. Cell-autonomous beta-catenin signaling regulates cortical precursor proliferation. *J Neurosci* 26, 12620-12630 (2006).
17. Link, A. J., Vink, M. K. S. & Tirrell, D. A. Preparation of the functionalizable methionine surrogate azidohomo-alanine via copper-catalyzed diazo transfer. *Nat Protoc* 2, 1879-1883 (2007).
18. Matsuzaki, M., Honkura, N., Ellis-Davies, G. C. R. & Kasai, H. Structural basis of long-term potentiation in single dendritic spines. *Nature* 429, 761-766 (2004).

27

28

19. Taylor, J. R. *An Introduction to Error Analysis*. (Sterling Publishing Company, 1997).

20. Marchler-Bauer, A. et al. CDD/SPARCLE: functional classification of proteins via subfamily domain architectures. *Nucleic Acids Research* 45, D200-D203 (2017).

21. Whitfield, J., Littlewood, T., Evan, G. I. & Soucek, L. The estrogen receptor fusion system in mouse models: a reversible switch. Cold Spring Harb Protoc 2015, 227-234 (2015).

22. Shoji, W. & Sato-Maeda, M. Application of heat shock promoter in transgenic zebrafish. Dev. Growth Differ. 50, 401-406 (2008).

23. Yamada, M., Suzuki, Y., Nagasaki, S. C., Okuno, H. & Imayoshi, I. Light Control of the Tet Gene Expression System in Mammalian Cells. Cell Rep 25, 487-500. e6 (2018).

24. Schnütgen, F. et al. A directional strategy for monitoring Cre-mediated recombination at the cellular level in the mouse. Nat Biotechnol 21, 562-565 (2003).

25. Flexner, L. B. & Goodman, R. H. Studies on memory: inhibitors of protein synthesis also inhibit catecholamine synthesis. Proc Natl Acad Sci USA 72, 4660-4663 (1975).

26. Zeisel, A. et al. Brain structure. Cell types in the mouse cortex and hippocampus revealed by single-cell RNA-seq. Science 347, 1138-1142 (2015).

27. Lake, B. B. et al. Neuronal subtypes and diversity revealed by single-nucleus RNA sequencing of the human brain. Science 352, 1586-1590 (2016).

28. Rosenberg, A. B. et al. Single-cell profiling of the developing mouse brain and spinal cord with split-pool barcoding. Science 360, 176-182 (2018).

29. He, L. et al. Single-cell RNA sequencing of mouse brain and lung vascular and vessel-associated cell types. Sci Data 5, 180160 (2018).

30. Lo, H.-W., Day, C.-P. & Hung, M.-C. Cancer-specific gene therapy. Adv. Genet. 54, 235-255 (2005).

31. Axelsen, J. B., Bock-Axelsen, J., Lotem, J., Sachs, L. & Domany, E. Genes overexpressed in different human solid cancers exhibit different tissue-specific expression profiles. Proc Natl Acad Sci USA 104, 13122-13127 (2007).

32. Garg, H., Suri, P., Gupta, J. C., Talwar, G. P. & Dubey, S. Survivin: a unique target for tumor therapy. Cancer Cell Int. 16, 49 (2016).

33. Kakinuma, H. et al. Probasin promoter (ARR(2)PB)-driven, prostate-specific expression of the human sodium iodide symporter (h-NIS) for targeted radioiodine therapy of prostate cancer. Cancer Res. 63, 7840-7844 (2003).

34. Yu, D., Jia, W. W., Gleave, M. E., Nelson, C. C. & Rennie, P. S. Prostate-tumor targeting of gene expression by lentiviral vectors containing elements of the probasin promoter. Prostate 59, 370-382 (2004).

35. Liu, T., Yuan, X. & Xu, D. Cancer-Specific Telomerase Reverse Transcriptase (TERT) Promoter Mutations: Biological and Clinical Implications. Genes (Basel) 7, 38 (2016).

36. Goodarzi, H. et al. Modulated Expression of Specific tRNAs Drives Gene Expression and Cancer Progression. Cell 165, 1416-1427 (2016).

37. Hagerman, R. J. et al. Fragile X syndrome. Nat Rev Dis Primers 3, 17065 (2017).

38. Ciaccio, C. et al. Fragile X syndrome: a review of clinical and molecular diagnoses. Ital J Pediatr 43, 39 (2017).

39. Banerjee, A., Ifrim, M. F., Valdez, A. N., Raj, N. & Bassell, G. J. Aberrant RNA translation in fragile X syndrome: From FMRP mechanisms to emerging therapeutic strategies. Brain Res. 1693, 24-36 (2018).

40. Darnell, J. C. et al. FMRP stalls ribosomal translocation on mRNAs linked to synaptic function and autism. Cell 146, 247-261 (2011).

41. Ascano, M. et al. FMRP targets distinct mRNA sequence elements to regulate protein expression. *Nature* 492, 382-386 (2012).

42. Pasciuto, E. & Bagni, C. SnapShot: FMRP mRNA targets and diseases. Cell 158, 1446-1446. e1 (2014).

43. Laggerbauer, B., Ostareck, D., Keidel, E. M., Ostareck-Lederer, A. & Fischer, U. Evidence that fragile X mental retardation protein is a negative regulator of translation. Hum. Mol. Genet. 10, 329-338 (2001).

44. Eyre, T. A., Collins, G. P., Goldstone, A. H. & Cwynarski, K. Time now to TORC the TORC? New developments in mTOR pathway inhibition in lymphoid malignancies. Br. J. Haematol. 166, 336-351 (2014).

45. Lipton, J. O. & Sahin, M. The neurology of mTOR. Neuron 84, 275-291 (2014).

46. Bhattacharya, A. et al. Targeting Translation Control with p70 S6 Kinase 1 Inhibitors to Reverse Phenotypes in Fragile X Syndrome Mice. Neuropsychopharmacology 41, 1991-2000 (2016).

47. Kelleher, R. J. & Bear, M. F. The autistic neuron: troubled translation? Cell 135, 401-406 (2008).

48. Hoeffer, C. A. & Klann, E. mTOR signaling: at the crossroads of plasticity, memory and disease. Trends in Neurosciences 33, 67-75 (2010).

The invention claimed is:

1. An expression system for a genetically encoded protein synthesis inhibitor having RNA N-glycosidase activity comprising:

(a) a first nucleic acid sequence encoding a first component of the protein synthesis inhibitor in operative linkage with a first expression control sequence, wherein the first component comprises an amino acid sequence as shown in SEQ ID NO:1 or an amino acid sequence having an identity of at least 95% thereto; and (b) a second nucleic acid sequence encoding a second component of the protein synthesis inhibitor in operative linkage with a second expression control sequence, wherein the second component comprises an amino acid sequence as shown in SEQ ID NO:2 or an amino acid sequence having an identity of at least 95% thereto; and (c) a third nucleic acid sequence encoding a trans-acting activator for the first and second expression control sequences in operative linkage with a third expression control sequence, wherein the first expression control sequence or the second expression control sequence comprise an inducible expression control sequence responsive to an external stimulus, wherein the external stimulus is external to the expression system, thereby providing the expression system with reversible inhibition of protein synthesis and temporal control, wherein the third expression control sequence is a cell-and/or tissue-type specific expression control sequence, wherein the expression system is adapted for expressing the first nucleic acid sequence and the second nucleic acid sequence separate from each other, wherein the first component and the second component together form a complex having RNA N-glycosidase activity, and wherein the first component alone and the second component alone lack RNA N-glycosidase activity.

2. A host comprising an expression system of claim 1, wherein the host is selected from the group consisting of an isolated cell, a cell preparation, a cell culture, an organoid, an isolated tissue and an isolated organ.

3. The host of claim 2, wherein the expression system provides spatial and temporal expression control.

4. A method of inhibiting protein synthesis in a host, comprising the steps:

(i) introducing an expression system of claim 1 into the host, and (ii) expressing in the host a protein synthesis inhibitor encoded by the expression system, wherein the protein synthesis inhibitor has RNA-glycosidase activity, whereby protein synthesis is inhibited in the host or in a part thereof.

5. The method of claim 4, wherein (i) expression of the protein synthesis inhibitor is under spatial and/or temporal control.

6. The expression system of claim 1 or a host comprising said expression system, wherein the host is selected from the group consisting of an isolated cell, a cell preparation, a cell culture, an organoid, a tissue and an organ; in combination with a buffer suitable for use in medicine, or for use in a screening procedure.

7. A kit for providing expression of a genetically encoded protein synthesis inhibitor having RNA N-glycosidase activity in a host, comprising:

(a) a first nucleic acid sequence encoding a first component of the protein synthesis inhibitor in operative linkage with a first inducible expression control sequence, wherein the first component comprises an amino acid sequence as shown in SEQ ID NO: 1 or an amino acid sequence having an identity of at least 95% thereto; and (b) a second nucleic acid sequence encoding a second component of the protein synthesis inhibitor in operative linkage with a second inducible expression control sequence, wherein the second component comprises an amino acid sequence as shown in SEQ ID NO:2 or an amino acid sequence having an identity of at least 95% thereto;

wherein the first nucleic acid sequence and the second nucleic acid sequence are provided for expression separate from each other, wherein the first inducible expression control sequence or the second inducible expression control sequence is responsive to an external stimulus, wherein the external stimulus is external to the host, thereby providing the host with reversible inhibition of protein synthesis, wherein the first component and the second component together form a complex having RNA N-glycosidase activity, and wherein the first component alone and the second component alone lack RNA N-glycosidase activity, and (c) a cell- and/or tissue-type specific expression control sequence in operative linkage with a third nucleic acid sequence encoding a trans-acting activator responsible for restricting expression of (a) and (b) to a targeted cell and/or tissue.

8. The host of claim 2, wherein the host is of human origin, or a non-human organism of mammalian origin.

9. The method of claim 4, wherein expression of the protein synthesis inhibitor is a cell- and/or tissue-specific expression.

10. The method of claim 4, wherein expression of the protein synthesis inhibitor is reversible.

11. The method of claim 4, wherein expression of the protein synthesis inhibitor is under conditions providing a recovery of protein synthesis in the host.

12. The method of claim 5, wherein (i) expression of the protein synthesis inhibitor is under spatial and temporal control.

13. A host comprising an expression system of claim 1, wherein the host is selected from the group consisting of an isolated cell, a cell preparation, a cell culture, an organoid, a non-human tissue, and a non-human organ.

14. The expression system of claim 1, wherein the external stimulus comprises a chemical substance.

15. The expression system of claim 14, wherein the chemical substance is doxycycline.

16. The kit of claim 7, wherein the external stimulus comprises a chemical substance.

17. The kit of claim 16, wherein the chemical substance is doxycycline.

* * * * *

SEQUENCE LISTING

```
<160> NUMBER OF SEQ ID NOS: 16

<210> SEQ ID NO 1
<211> LENGTH: 141
<212> TYPE: PRT
<213> ORGANISM: Zea mays

<400> SEQUENCE: 1

Met Lys Phe Thr Glu Ile Phe Pro Val Glu Asp Ala Asn Tyr Pro Tyr
1               5                   10                  15

Ser Ala Phe Ile Ala Ser Val Arg Lys Asp Val Ile Lys His Cys Thr
            20                  25                  30

Asp His Lys Gly Ile Phe Gln Pro Val Leu Pro Pro Glu Lys Lys Val
        35                  40                  45
```

-continued

```
Pro Glu Leu Trp Leu Tyr Thr Glu Leu Lys Thr Arg Thr Ser Ser Ile
    50                  55                  60

Thr Leu Ala Ile Arg Met Asp Asn Leu Tyr Leu Val Gly Phe Arg Thr
65                  70                  75                  80

Pro Gly Gly Val Trp Trp Glu Phe Gly Lys Asp Gly Asp Thr His Leu
                85                  90                  95

Leu Gly Asp Asn Pro Arg Trp Leu Gly Phe Gly Gly Arg Tyr Gln Asp
                100                 105                 110

Leu Ile Gly Asn Lys Gly Leu Glu Thr Val Thr Met Gly Arg Ala Glu
                115                 120                 125

Met Thr Arg Ala Val Asn Asp Leu Ala Lys Lys Lys Lys
    130                 135                 140

<210> SEQ ID NO 2
<211> LENGTH: 103
<212> TYPE: PRT
<213> ORGANISM: Zea mays

<400> SEQUENCE: 2

Met Ala Ala Asp Pro Gln Ala Asp Thr Lys Ser Lys Leu Val Lys Leu
1               5                   10                  15

Val Val Met Val Cys Glu Gly Leu Arg Phe Asn Thr Val Ser Arg Thr
                20                  25                  30

Val Asp Ala Gly Phe Asn Ser Gln His Gly Val Thr Leu Thr Val Thr
            35                  40                  45

Gln Gly Lys Gln Val Gln Lys Trp Asp Arg Ile Ser Lys Ala Ala Phe
    50                  55                  60

Glu Trp Ala Asp His Pro Thr Ala Val Ile Pro Asp Met Gln Lys Leu
65                  70                  75                  80

Gly Ile Lys Asp Lys Asn Glu Ala Ala Arg Ile Val Ala Leu Val Lys
                85                  90                  95

Asn Gln Thr Thr Ala Ala Ala
                100

<210> SEQ ID NO 3
<211> LENGTH: 268
<212> TYPE: PRT
<213> ORGANISM: Zea mays

<400> SEQUENCE: 3

Met Lys Phe Thr Glu Ile Phe Pro Val Glu Asp Ala Asn Tyr Pro Tyr
1               5                   10                  15

Ser Ala Phe Ile Ala Ser Val Arg Lys Asp Val Ile Lys His Cys Thr
                20                  25                  30

Asp His Lys Gly Ile Phe Gln Pro Val Leu Pro Pro Glu Lys Lys Val
            35                  40                  45

Pro Glu Leu Trp Leu Tyr Thr Glu Leu Lys Thr Arg Thr Ser Ser Ile
    50                  55                  60

Thr Leu Ala Ile Arg Met Asp Asn Leu Tyr Leu Val Gly Phe Arg Thr
65                  70                  75                  80

Pro Gly Gly Val Trp Trp Glu Phe Gly Lys Asp Gly Asp Thr His Leu
                85                  90                  95

Leu Gly Asp Asn Pro Arg Trp Leu Gly Phe Gly Gly Arg Tyr Gln Asp
                100                 105                 110

Leu Ile Gly Asn Lys Gly Leu Glu Thr Val Thr Met Gly Arg Ala Glu
                115                 120                 125
```

-continued

```
Met Thr Arg Ala Val Asn Asp Leu Ala Lys Lys Lys Met Ala Thr
    130                 135                 140

Leu Glu Glu Glu Glu Val Gln Met Gln Met Gln Met Pro Glu Ala Ala
145                 150                 155

Asp Leu Ala Ala Ala Ala Ala Ala Asp Pro Gln Ala Asp Thr Lys Ser
                165                 170                 175

Lys Leu Val Lys Leu Val Val Met Val Cys Glu Gly Leu Arg Phe Asn
            180                 185                 190

Thr Val Ser Arg Thr Val Asp Ala Gly Phe Asn Ser Gln His Gly Val
            195                 200                 205

Thr Leu Thr Val Thr Gln Gly Lys Gln Val Gln Lys Trp Asp Arg Ile
    210                 215                 220

Ser Lys Ala Ala Phe Glu Trp Ala Asp His Pro Thr Ala Val Ile Pro
225                 230                 235                 240

Asp Met Gln Lys Leu Gly Ile Lys Asp Lys Asn Glu Ala Ala Arg Ile
                245                 250                 255

Val Ala Leu Val Lys Asn Gln Thr Thr Ala Ala Ala
            260                 265
```

<210> SEQ ID NO 4
<211> LENGTH: 190
<212> TYPE: PRT
<213> ORGANISM: Zea mays

<400> SEQUENCE: 4

```
Asn Tyr Pro Tyr Ser Ala Phe Ile Ala Ser Val Arg Lys Asp Val Ile
1               5                   10                  15

Lys His Cys Thr Asp His Lys Gly Ile Phe Gln Pro Val Leu Pro Pro
                20                  25                  30

Glu Lys Lys Val Pro Glu Leu Trp Leu Tyr Thr Glu Leu Lys Thr Arg
            35                  40                  45

Thr Ser Ser Ile Thr Leu Ala Ile Arg Met Asp Asn Leu Tyr Leu Val
    50                  55                  60

Gly Phe Arg Thr Pro Gly Gly Val Trp Trp Glu Phe Gly Lys Asp Gly
65                  70                  75                  80

Asp Thr His Leu Leu Gly Asp Asn Pro Arg Trp Leu Gly Phe Gly Gly
                85                  90                  95

Arg Tyr Gln Asp Leu Ile Gly Asn Lys Gly Leu Glu Thr Val Thr Met
                100                 105                 110

Gly Arg Ala Glu Met Thr Arg Ala Val Asn Asp Leu Ala Lys Lys Lys
            115                 120                 125

Lys Met Leu Glu Pro Gln Ala Asp Thr Lys Ser Lys Leu Val Lys Leu
    130                 135                 140

Val Val Met Val Cys Glu Gly Leu Arg Phe Asn Thr Val Ser Arg Thr
145                 150                 155                 160

Val Asp Ala Gly Phe Asn Ser Gln His Gly Val Thr Leu Thr Val Thr
                165                 170                 175

Gln Gly Lys Gln Val Gln Lys Trp Asp Arg Ile Ser Lys Ala
            180                 185                 190
```

<210> SEQ ID NO 5
<211> LENGTH: 194
<212> TYPE: PRT
<213> ORGANISM: Artificial Sequence
<220> FEATURE:
<223> OTHER INFORMATION: consensus sequence -continued

```
<400> SEQUENCE: 5

Ala Asp Ser Tyr Arg Asp Phe Ile Glu Ser Leu Arg Lys Arg Leu Ala
1               5                   10                  15

Ser Gly Asp His Val Ser His Gly Ile Pro Val Leu Pro Pro Gln Val
                20                  25                  30

Pro Pro Thr Pro Pro Ala Arg Trp Val Leu Val Val Leu Arg Asn Thr
            35                  40                  45

Gly Gly Arg Ser Ala Thr Leu Ala Ile Arg Val Asp Asn Leu Tyr Leu
    50                  55                  60

Val Gly Phe Arg Asn Arg Asn Gly Tyr Trp Phe Glu Phe Ala Asp Gly
65                  70                  75                  80

Ser Ile Tyr His Pro Ile Leu Ile Pro Gly Ser Thr Thr Leu Pro Phe
                85                  90                  95

Gly Gly Ser Tyr Ser Thr Leu Glu Arg Val Ala Gly Ala Arg Leu Glu
                100                 105                 110

Glu Val Pro Leu Gly Arg Gln Gln Leu Glu Glu Ala Val Ser Gln Leu
            115                 120                 125

Ala Arg Tyr Asp Pro Gly Gly Ala Pro Thr Ala Asp Ile Ala Arg Ala
        130                 135                 140

Leu Ala Val Leu Ile Gln Met Val Cys Glu Ala Ala Arg Phe Arg Tyr
145                 150                 155                 160

Ile Glu Asp Ala Val Arg Ala Gly Phe Asp Ser Gly Ala Gly Val Ser
                165                 170                 175

Pro Thr Gly Thr Met Val Lys Leu Val Asn Asn Trp Gly Asp Leu Ser
                180                 185                 190

Lys Ala

<210> SEQ ID NO 6
<211> LENGTH: 574
<212> TYPE: PRT
<213> ORGANISM: Ricinus communis

<400> SEQUENCE: 6

Met Lys Leu Gln Gly Asn Phe Ile Val Trp Val Tyr Ala Val Ala Thr
1               5                   10                  15

Trp Val Trp Leu Gly Ser Ile Ser Gly Trp Ser Phe Thr Ser Gln Asp
                20                  25                  30

Asn Ile Leu Leu Leu Lys Gln Tyr Pro Thr Val Thr Phe Thr Thr Ala
            35                  40                  45

Gly Ala Thr Ala Glu Ser Tyr Arg Ala Phe Ile Asn Ala Met Arg Arg
    50                  55                  60

Gln Leu Leu Thr Gly Asp Asp Val Arg His Gln Ile Pro Val Leu Arg
65                  70                  75                  80

Asn Arg Val Gly Phe Pro Ile Asn Gln Arg Phe Val Leu Val Gln Leu
                85                  90                  95

Thr Asn Gln Ala Glu Leu Ser Ile Thr Leu Ala Val Asp Val Thr Asn
                100                 105                 110

Ala Tyr Val Val Gly Tyr Arg Ala Gly Asn Asn Ala Tyr Phe Phe Gln
        115                 120                 125

Pro Asp Asn Pro Glu Asp Ala Glu Ala Ile Thr His Leu Phe Thr Asp
        130                 135                 140

Ala Gln Thr Arg Gln Thr Phe Ala Phe Gly Gly Asn Tyr Asp Arg Leu
145                 150                 155                 160

Glu Gln Leu Gly Gly Leu Arg Glu Asn Ile Glu Leu Gly Asn Gly Pro
```

-continued

```
                   165                 170                 175

Leu Glu Asp Ala Ile Ser Ala Leu Tyr Tyr Tyr Ser Thr Gly Gly Thr
            180                 185                 190

Gln Leu Pro Ala Leu Ala Arg Ser Phe Met Val Cys Ile Gln Met Ile
            195                 200                 205

Ser Glu Ala Val Arg Phe Gln Tyr Ile Glu Gly Glu Met Arg Thr Arg
            210                 215                 220

Ile Arg Tyr Asn Arg Arg Thr Ala Pro Asp Ala Ser Val Ile Arg Leu
225                 230                 235                 240

Glu Asn Ser Trp Gly Arg Leu Ser Thr Ala Ile Gln Glu Ser Asn Gln
                245                 250                 255

Gly Ala Phe Ala Ser Pro Ile Gln Leu Gln Arg Arg Asn Gly Ser Arg
            260                 265                 270

Phe Asp Val Tyr Asp Val Ser Ile Leu Ile Pro Ile Ile Ala Leu Met
            275                 280                 285

Val Tyr Arg Cys Ala Pro Pro Pro Ser Leu Gln Leu Pro Tyr Leu Ile
            290                 295                 300

Lys Gln Val Val Pro Met Phe Asn Asp Asp Val Cys Val Asp Pro Glu
305                 310                 315                 320

Pro Thr Val Arg Ile Val Gly Arg Asn Gly Leu Cys Val Asp Val Arg
                325                 330                 335

Asp Gly Glu Phe His Asn Gly Asn Pro Ile Gln Leu Trp Pro Cys Lys
            340                 345                 350

Ser Asn Thr Asp Ala Asn Gln Leu Trp Thr Leu Lys Arg Asp Asn Thr
            355                 360                 365

Ile Arg Ser Asn Gly Lys Cys Leu Thr Thr Tyr Gly Tyr Ser Pro Gly
            370                 375                 380

Val Tyr Val Met Ile Tyr Asp Cys Asn Thr Ala Val Thr Asp Ala Thr
385                 390                 395                 400

Arg Trp Gln Ile Trp Asp Asn Gly Thr Ile Ile Asn Pro Arg Ser Ser
                405                 410                 415

Leu Val Leu Ala Ala Thr Ser Gly Asn Ser Gly Thr Thr Leu Thr Val
            420                 425                 430

Lys Thr Asn Ile Tyr Ala Thr Ser Gln Gly Trp Leu Pro Thr Asn Asn
            435                 440                 445

Thr Gln Pro Phe Val Thr Ser Ile Val Gly Leu Tyr Asp Leu Cys Leu
            450                 455                 460

Gln Ala Asn Ser Gly Asn Val Trp Leu Glu Glu Cys Ala Ser Asn Arg
465                 470                 475                 480

Ala Glu Gln Gln Trp Ala Leu Tyr Ala Asp Gly Ser Ile Arg Pro Gln
                485                 490                 495

Gln Asn Gln Asp Asn Cys Leu Thr Ser Asp Ala Ser Thr Gln Gly Thr
            500                 505                 510

Ile Val Lys Ile Leu Ser Cys Ser Pro Gly Ser Ser Gly Gln Arg Trp
            515                 520                 525

Met Trp Lys Asn Asp Gly Thr Ile Trp Asn Leu Tyr Tyr Gly Leu Val
            530                 535                 540

Leu Asp Val Arg Gln Ser Asp Pro Ser Leu Lys Gln Ile Ile Ile Trp
545                 550                 555                 560

Pro Phe Thr Gly Asn Pro Asn Gln Lys Trp Leu Pro Leu Leu
                565                 570
```

<210> SEQ ID NO 7

```
<211> LENGTH: 289
<212> TYPE: PRT
<213> ORGANISM: Trichosanthes kirilowii

<400> SEQUENCE: 7

Met Ile Arg Phe Leu Val Leu Ser Leu Leu Ile Leu Thr Leu Phe Leu
1               5                   10                  15

Thr Thr Pro Ala Val Glu Gly Asp Val Ser Phe Arg Leu Ser Gly Ala
                20                  25                  30

Thr Ser Ser Ser Tyr Gly Val Phe Ile Ser Asn Leu Arg Lys Ala Leu
            35                  40                  45

Pro Asn Glu Arg Lys Leu Tyr Asp Ile Pro Leu Leu Arg Ser Ser Leu
        50                  55                  60

Pro Gly Ser Gln Arg Tyr Ala Leu Val His Leu Thr Asn Tyr Ala Asp
65                  70                  75                  80

Glu Thr Ile Ser Val Ala Ile Asp Val Thr Ser Val Tyr Ile Met Gly
                85                  90                  95

Tyr Arg Ala Gly Asp Thr Ser Tyr Phe Phe Asn Glu Ala Ser Ala Thr
            100                 105                 110

Glu Ala Ala Lys Tyr Val Phe Lys Asp Ala Met Arg Lys Val Thr Leu
            115                 120                 125

Pro Tyr Ser Gly Asn Tyr Glu Arg Leu Gln Thr Ala Ala Gly Lys Ile
        130                 135                 140

Arg Glu Asn Ile Pro Leu Gly Leu Pro Ala Leu Asp Ser Ala Ile Thr
145                 150                 155                 160

Thr Leu Phe Tyr Tyr Asn Ala Asn Ser Ala Ala Ser Ala Leu Met Val
                165                 170                 175

Leu Ile Gln Ser Thr Ser Glu Ala Ala Arg Tyr Lys Phe Ile Glu Gln
            180                 185                 190

Gln Ile Gly Lys Arg Val Asp Lys Thr Phe Leu Pro Ser Leu Ala Ile
            195                 200                 205

Ile Ser Leu Glu Asn Ser Trp Ser Ala Leu Ser Lys Gln Ile Gln Ile
        210                 215                 220

Ala Ser Thr Asn Asn Gly Gln Phe Glu Thr Pro Val Val Leu Ile Asn
225                 230                 235                 240

Ala Gln Asn Gln Arg Val Thr Ile Thr Asn Val Asp Ala Gly Val Val
            245                 250                 255

Thr Ser Asn Ile Ala Leu Leu Leu Asn Arg Asn Asp Met Ala Ala Met
        260                 265                 270

Asp Asp Asp Val Pro Met Thr Gln Ser Phe Gly Cys Gly Ser Tyr Ala
        275                 280                 285

Ile

<210> SEQ ID NO 8
<211> LENGTH: 316
<212> TYPE: PRT
<213> ORGANISM: Gelonium multiflorum

<400> SEQUENCE: 8

Met Lys Gly Asn Met Lys Val Tyr Trp Ile Lys Ile Ala Val Ala Thr
1               5                   10                  15

Trp Phe Cys Cys Thr Thr Ile Val Leu Gly Ser Thr Ala Arg Ile Phe
                20                  25                  30

Ser Leu Pro Thr Asn Asp Glu Glu Glu Thr Ser Lys Thr Leu Gly Leu
            35                  40                  45
```

```
Asp Thr Val Ser Phe Ser Thr Lys Gly Ala Thr Tyr Ile Thr Tyr Val
    50              55              60

Asn Phe Leu Asn Glu Leu Arg Val Lys Leu Lys Pro Glu Gly Asn Ser
65              70              75              80

His Gly Ile Pro Leu Leu Arg Lys Lys Cys Asp Asp Pro Gly Lys Cys
            85              90              95

Phe Val Leu Val Ala Leu Ser Asn Asp Asn Gly Gln Leu Ala Glu Ile
            100             105             110

Ala Ile Asp Val Thr Ser Val Tyr Val Val Gly Tyr Gln Val Arg Asn
            115             120             125

Arg Ser Tyr Phe Phe Lys Asp Ala Pro Asp Ala Ala Tyr Glu Gly Leu
    130             135             140

Phe Lys Asn Thr Ile Lys Thr Arg Leu His Phe Gly Gly Ser Tyr Pro
145             150             155             160

Ser Leu Glu Gly Glu Lys Ala Tyr Arg Glu Thr Thr Asp Leu Gly Ile
            165             170             175

Glu Pro Leu Arg Ile Gly Ile Lys Lys Leu Asp Glu Asn Ala Ile Asp
            180             185             190

Asn Tyr Lys Pro Thr Glu Ile Ala Ser Ser Leu Leu Val Val Ile Gln
            195             200             205

Met Val Ser Glu Ala Ala Arg Phe Thr Phe Ile Glu Asn Gln Ile Arg
    210             215             220

Asn Asn Phe Gln Gln Arg Ile Arg Pro Ala Asn Asn Thr Ile Ser Leu
225             230             235             240

Glu Asn Lys Trp Gly Lys Leu Ser Phe Gln Ile Arg Thr Ser Gly Ala
            245             250             255

Asn Gly Met Phe Ser Glu Ala Val Glu Leu Glu Arg Ala Asn Gly Lys
            260             265             270

Lys Tyr Tyr Val Thr Ala Val Asp Gln Val Lys Pro Lys Ile Ala Leu
    275             280             285

Leu Lys Phe Val Asp Lys Asp Pro Lys Thr Ser Leu Ala Ala Glu Leu
    290             295             300

Ile Ile Gln Asn Tyr Glu Ser Leu Val Gly Phe Asp
305             310             315
```

```
<210> SEQ ID NO 9
<211> LENGTH: 154
<212> TYPE: PRT
<213> ORGANISM: Zea mays

<400> SEQUENCE: 9

Tyr Ser Ala Phe Ile Ala Ser Val Arg Lys Asp Val Ile Lys His Cys
1               5               10              15

Thr Asp His Lys Gly Ile Phe Gln Pro Val Leu Pro Pro Glu Lys Lys
            20              25              30

Val Pro Glu Leu Trp Leu Tyr Thr Glu Leu Lys Thr Arg Thr Ser Ser
        35              40              45

Ile Thr Leu Ala Ile Arg Met Asp Asn Leu Tyr Leu Val Gly Phe Arg
    50              55              60

Thr Pro Gly Gly Val Trp Trp Glu Phe Gly Lys Asp Gly Asp Thr His
65              70              75              80

Leu Leu Gly Asp Asn Pro Arg Trp Leu Gly Phe Gly Gly Arg Tyr Gln
            85              90              95

Asp Leu Ile Gly Asn Lys Gly Leu Glu Thr Val Thr Met Gly Arg Ala
            100             105             110
```

```
Glu Met Thr Arg Ala Val Asn Asp Leu Ala Lys Lys Lys Lys Met Leu
        115                 120                 125

Glu Pro Gln Ala Asp Thr Lys Ser Lys Leu Val Lys Leu Val Val Met
    130                 135                 140

Val Cys Glu Gly Leu Arg Phe Asn Thr Val
145                 150
```

```
<210> SEQ ID NO 10
<211> LENGTH: 163
<212> TYPE: PRT
<213> ORGANISM: Ricinus communis

<400> SEQUENCE: 10

Tyr Arg Ala Phe Ile Asn Ala Met Arg Arg Gln Leu Leu Thr Gly Asp
1               5                   10                  15

Asp Val Arg His Gln Ile Pro Val Leu Arg Asn Arg Val Gly Phe Pro
                20                  25                  30

Ile Asn Gln Arg Phe Val Leu Val Gln Leu Thr Asn Gln Ala Glu Leu
        35                  40                  45

Ser Ile Thr Leu Ala Val Asp Val Thr Asn Ala Tyr Val Val Gly Tyr
    50                  55                  60

Arg Ala Gly Asn Asn Ala Tyr Phe Phe Gln Pro Asp Asn Pro Glu Asp
65                  70                  75                  80

Ala Glu Ala Ile Thr His Leu Phe Thr Asp Ala Gln Thr Arg Gln Thr
                85                  90                  95

Phe Ala Phe Gly Gly Asn Tyr Asp Arg Leu Glu Gln Leu Gly Gly Leu
            100                 105                 110

Arg Glu Asn Ile Glu Leu Gly Asn Gly Pro Leu Glu Asp Ala Ile Ser
        115                 120                 125

Ala Leu Tyr Tyr Tyr Ser Thr Gly Gly Thr Gln Leu Pro Ala Leu Ala
    130                 135                 140

Arg Ser Phe Met Val Cys Ile Gln Met Ile Ser Glu Ala Val Arg Phe
145                 150                 155                 160

Gln Tyr Ile
```

```
<210> SEQ ID NO 11
<211> LENGTH: 158
<212> TYPE: PRT
<213> ORGANISM: Zea mays

<400> SEQUENCE: 11

Tyr Ser Ala Phe Ile Ala Ser Val Arg Lys Asp Val Ile Lys His Cys
1               5                   10                  15

Thr Asp His Lys Gly Ile Phe Gln Pro Val Leu Pro Pro Glu Lys Lys
                20                  25                  30

Val Pro Glu Leu Trp Leu Tyr Thr Glu Leu Lys Thr Arg Thr Ser Ser
        35                  40                  45

Ile Thr Leu Ala Ile Arg Met Asp Asn Leu Tyr Leu Val Gly Phe Arg
    50                  55                  60

Thr Pro Gly Gly Val Trp Trp Glu Phe Gly Lys Asp Gly Asp Thr His
65                  70                  75                  80

Leu Leu Gly Asp Asn Pro Arg Trp Leu Gly Phe Gly Gly Arg Tyr Gln
                85                  90                  95

Asp Leu Ile Gly Asn Lys Gly Leu Glu Thr Val Thr Met Gly Arg Ala
            100                 105                 110
```

Glu Met Thr Arg Ala Val Asn Asp Leu Ala Lys Lys Lys Lys Met Leu
      115              120                125

Glu Pro Gln Ala Asp Thr Lys Ser Lys Leu Val Lys Leu Val Val Met
   130              135               140

Val Cys Glu Gly Leu Arg Phe Asn Thr Val Ser Arg Thr Val
145              150              155

<210> SEQ ID NO 12
<211> LENGTH: 158
<212> TYPE: PRT
<213> ORGANISM: Trichosanthes kirilowii

<400> SEQUENCE: 12

Tyr Gly Val Phe Ile Ser Asn Leu Arg Lys Ala Leu Pro Asn Glu Arg
1             5               10               15

Lys Leu Tyr Asp Ile Pro Leu Leu Arg Ser Ser Leu Pro Gly Ser Gln
       20              25              30

Arg Tyr Ala Leu Val His Leu Thr Asn Tyr Ala Asp Glu Thr Ile Ser
      35              40              45

Val Ala Ile Asp Val Thr Ser Val Tyr Ile Met Gly Tyr Arg Ala Gly
     50              55             60

Asp Thr Ser Tyr Phe Phe Asn Glu Ala Ser Ala Thr Glu Ala Ala Lys
65             70             75              80

Tyr Val Phe Lys Asp Ala Met Arg Lys Val Thr Leu Pro Tyr Ser Gly
         85            90             95

Asn Tyr Glu Arg Leu Gln Thr Ala Ala Gly Lys Ile Arg Glu Asn Ile
          100            105           110

Pro Leu Gly Leu Pro Ala Leu Asp Ser Ala Ile Thr Thr Leu Phe Tyr
         115            120           125

Tyr Asn Ala Asn Ser Ala Ala Ser Ala Leu Met Val Leu Ile Gln Ser
       130              135             140

Thr Ser Glu Ala Ala Arg Tyr Lys Phe Ile Glu Gln Gln Ile
145             150             155

<210> SEQ ID NO 13
<211> LENGTH: 115
<212> TYPE: PRT
<213> ORGANISM: Zea mays

<400> SEQUENCE: 13

Leu Ala Ile Arg Met Asp Asn Leu Tyr Leu Val Gly Phe Arg Thr Pro
1             5               10               15

Gly Gly Val Trp Trp Glu Phe Gly Lys Asp Gly Asp Thr His Leu Leu
       20              25              30

Gly Asp Asn Pro Arg Trp Leu Gly Phe Gly Gly Arg Tyr Gln Asp Leu
      35              40              45

Ile Gly Asn Lys Gly Leu Glu Thr Val Thr Met Gly Arg Ala Glu Met
     50              55             60

Thr Arg Ala Val Asn Asp Leu Ala Lys Lys Lys Lys Met Leu Glu Pro
65             70             75              80

Gln Ala Asp Thr Lys Ser Lys Leu Val Lys Leu Val Val Met Val Cys
         85            90             95

Glu Gly Leu Arg Phe Asn Thr Val Ser Arg Thr Val Asp Ala Gly Phe
          100            105           110

Asn Ser Gln
         115

<210> SEQ ID NO 14
<211> LENGTH: 119
<212> TYPE: PRT
<213> ORGANISM: Gelonium multiflorum

<400> SEQUENCE: 14

Ile Ala Ile Asp Val Thr Ser Val Tyr Val Val Gly Tyr Gln Val Arg
1               5                   10                  15

Asn Arg Ser Tyr Phe Phe Lys Asp Ala Pro Asp Ala Ala Tyr Glu Gly
                20                  25                  30

Leu Phe Lys Asn Thr Ile Lys Thr Arg Leu His Phe Gly Gly Ser Tyr
            35                  40                  45

Pro Ser Leu Glu Gly Glu Lys Ala Tyr Arg Glu Thr Thr Asp Leu Gly
        50                  55                  60

Ile Glu Pro Leu Arg Ile Gly Ile Lys Lys Leu Asp Glu Asn Ala Ile
65                  70                  75                  80

Asp Asn Tyr Lys Pro Thr Glu Ile Ala Ser Ser Leu Leu Val Val Ile
                85                  90                  95

Gln Met Val Ser Glu Ala Ala Arg Phe Thr Phe Ile Glu Asn Gln Ile
            100                 105                 110

Arg Asn Asn Phe Gln Gln Arg
        115

<210> SEQ ID NO 15
<211> LENGTH: 910
<212> TYPE: DNA
<213> ORGANISM: Artificial Sequence
<220> FEATURE:
<223> OTHER INFORMATION: nucleic acid sequence

<400> SEQUENCE: 15
agcaattcca caacactttt gtcttatacc aactttccgt accacttcct accctcgtaa      60
agtcgacacc ggggcccaga tctatgaagt tcactgaaat cttccccgtg gaggacgcga     120
actaccctta cagcgccttc atcgcgtcgg tccggaaaga cgtgatcaaa cactgcaccg     180
accataaagg gatcttccag cccgtgctgc accggagaa gaaggtcccg gagctatggt     240
tgtacacaga gctcaaaact aggaccagct ccatcacgct cgccatacgc atggacaacc     300
tgtacctcgt gggcttcagg accccgggcg gggtgtggtg ggagttcggc aaggacggcg     360
acacccacct cctcggcgac aaccccaggt ggctcggctt cggcggcagg taccaggacc     420
tcatcggcaa caagggtctg gagaccgtca ccatgggccg cgccgaaatg accagggccg     480
tcaacgacct ggcgaagaag aagaagatgg cgacactgga ggaggaggag gtgcagatgc     540
agatgcagat gccggaggcc gctgatctgg cggcggcggc agcggctgac ccacaggccg     600
acacgaagag caagctggtg aagctggtgg tcatggtgtg cgagggggctg cggttcaaca     660 ccgtgtcccg cacggtggac gcggggttca acagccagca cggggtgacc ttgaccgtga     720
cgcaggggaa gcaggtgcag aagtgggaca ggatctccaa ggcggccttc gagtgggctg     780
accaccccac cgctgtgatc cccgacatgc agaagcttgg catcaaggat aagaacgaag     840
cagcgaggat cgttgcgctc gttaagaatc aaactactgc ggcggcttga gcggccgccg     900
gcgatatctc                                                          910

<210> SEQ ID NO 16
<211> LENGTH: 910
<212> TYPE: DNA
<213> ORGANISM: Artificial Sequence -continued

```
<220> FEATURE:
<223> OTHER INFORMATION: reverse complement

<400> SEQUENCE: 16
gagatatcgc cggcggccgc tcaagccgcc gcagtagttt gattcttaac gagcgcaacg      60
atcctcgctg cttcgttctt atccttgatg ccaagcttct gcatgtcggg gatcacagcg     120
gtggggtggt cagcccactc gaaggccgcc ttggagatcc tgtcccactt ctgcacctgc     180 ttccctgcg  tcacggtcaa ggtcacccg  tgctggctgt tgaaccccgc gtccaccgtg     240
cgggacacgg tgttgaaccg cagcccctcg cacaccatga ccaccagctt caccagcttg     300
ctcttcgtgt cggcctgtgg gtcagccgct gccgccgccg ccagatcagc ggcctccggc     360
atctgcatct gcatctgcac ctcctcctcc tccagtgtcg ccatcttctt cttcttcgcc     420
aggtcgttga cggccctggt catttcggcg cggcccatgg tgacggtctc cagacccttg     480
ttgccgatga ggtcctggta cctgccgccg aagccgagcc acctggggtt gtcgccgagg     540
aggtgggtgt cgccgtcctt gccgaactcc caccacaccc cgcccggggt cctgaagccc     600
acgaggtaca ggttgtccat gcgtatggcg agcgtgatgg agctggtcct agttttgagc     660
tctgtgtaca accatagctc cgggaccttc ttctccggtg gcagcacggg ctggaagatc     720
cctttatggt cggtgcagtg tttgatcacg tctttccgga ccgacgcgat gaaggcgctg     780
taagggtagt tcgcgtcctc cacgggggaag atttcagtga acttcataga tctgggcccc     840
ggtgtcgact ttacgagggt aggaagtggt acggaaagtt ggtataagac aaaagtgttg     900
tggaattgct                                                           910
```